(12) United States Patent
Fischer et al.

(10) Patent No.: US 8,518,676 B2
(45) Date of Patent: *Aug. 27, 2013

(54) POLYPEPTIDES HAVING C4 DICARBOXYLIC ACID TRANSPORTER ACTIVITY AND POLYNUCLEOTIDES ENCODING SAME

(75) Inventors: Amanda Fischer, Davis, CA (US); Debbie Yaver, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/404,258

(22) Filed: Feb. 24, 2012

(65) Prior Publication Data

US 2012/0149079 A1    Jun. 14, 2012

Related U.S. Application Data

(63) Continuation of application No. 13/165,696, filed on Jun. 21, 2011, now Pat. No. 8,158,395.

(60) Provisional application No. 61/356,868, filed on Jun. 21, 2010.

(51) Int. Cl.
*C12N 15/31* (2006.01)
*C12N 1/15* (2006.01)
*C12P 7/46* (2006.01)

(52) U.S. Cl.
USPC ........................................... 435/145

(58) Field of Classification Search
None
See application file for complete search history.

(56) References Cited

U.S. PATENT DOCUMENTS

| 3,063,910 A | 11/1962 | Abe et al. |
| 5,536,661 A | 7/1996 | Boel et al. |
| 7,504,490 B1 | 3/2009 | Weinstock et al. |

FOREIGN PATENT DOCUMENTS

| EP | 2471943 A1 | 7/2010 |
| WO | 2007061590 A1 | 5/2007 |
| WO | 2008144626 A1 | 11/2008 |
| WO | 2009011974 A1 | 1/2009 |
| WO | 2009065778 A1 | 5/2009 |
| WO | 2009155382 A1 | 12/2009 |
| WO | 2010003728 A1 | 1/2010 |
| WO | 2010111344 A2 | 9/2010 |
| WO | 2011024583 A1 | 3/2011 |
| WO | 2011028643 A1 | 3/2011 |
| WO | 2011066304 A2 | 6/2011 |

OTHER PUBLICATIONS

Ludwig et al, 1998, Plant Physiol 117 (3), 1071-1081.
Fedorova et al, 2007, UniProt Access No. A1C406.
BATTAT 1991, Biotechnol Bioeng 37, 1108-1116.
Bauer 1999, FEMS Microbiol Lett 179, 107-113.
Bercovitz 1990, Appl Environ Microbiol 56, 1594-1597.
Camarasa 2001, Appl Environ Microbiol 67(9), 4144-4151.
Fedorova 2008, PLoS Genetics 4(4), 1-13.
Grobler 1995, Yeast 11, 1485-1491.
Nierman 2005, Nature 438 (22), 1151-1156.
Peleg 1988, Appl Microbiol Biotechnol 28, 69-75.
Pines 1997, Appl Microbiol Biotechnol 48, 248-255.
Sauer 2008, Trends Biotechnol 26, 100-108.
Zelle 2008, Appl Environ Microbiol 74, 2766-2777.
Machida et al 2006, Uniprot Access No. Q2UGL1.
Machida et al 2006, Uniprot Access No. Q2USG3.
Birren et al, 2008, UniProt Access No. B6JXU3.
Elleuche et al, 2009, Curr Genet 55, 211-222.
Goldberg et al, 2006, J Chem Technol Biotechnol 81(10), 1601-1611.
Nevoigt, 2008, Microbiol Mol Biol Revs 72(3), 379-412.
Nielsen et al, 2008, FEMS Yeast Res 8, 122-131.
Geneseq, Access No. AWP70496.
Geneseq, Access No. ATT44026.
Nierman et al, 2005, UniProt Access No. Q4WCF3.
Zelle, Rintze Meindert. Metabolic engineering of *Saccharomyces cerevisiae* for C4-dicarboxylic acid production. PhD Thesis. Delft Univerisy of Technology, Delft, 2011.
Lubertozzi et al, 2008, Biotechnol Advances 27, 53-75.
Whisstock et al 2003 Qtr Rev Biophys 36(3) 307-340.

*Primary Examiner* — Rebecca Prouty
(74) *Attorney, Agent, or Firm* — Eric J. Fechter

(57) ABSTRACT

The present invention relates to isolated polypeptides having C4-dicarboxylic acid transporter activity and isolated polynucleotides encoding the polypeptides. The invention also relates to nucleic acid constructs, vectors, and host cells comprising the polynucleotides as well as methods of producing and using the polypeptides, and methods of producing C4-dicarboxylic acids, such as malic acid.

33 Claims, 13 Drawing Sheets

POLYPEPTIDES HAVING C4 DICARBOXYLIC ACID TRANSPORTER ACTIVITY AND POLYNUCLEOTIDES ENCODING SAME

CROSS REFERENCE TO RELATED APPLICATIONS

This application is a continuation of U.S. patent application Ser. No. 13/165,696, filed Jun. 21, 2011, now U.S. Pat. No. 8,158,395, which claims priority benefit of U.S. Provisional Application Ser. No. 61/356,868, filed Jun. 21, 2010. The entire content of these applications is incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which is incorporated herein by reference.

BACKGROUND OF THE INVENTION

1. Field of the Invention

The present invention relates to polypeptides having C4-dicarboxylic acid transporter activity and polynucleotides encoding the polypeptides. The invention also relates to nucleic acid constructs, vectors, and host cells comprising the polynucleotides as well as methods of producing and using the polypeptides, and methods of producing C4-dicarboxylic acids, such as malic acid.

2. Description of the Related Art

Organic acids have a long history of commercial use in a variety of industries. For example, organic acids are used in the food and feed industries (citric acid, ascorbic acid, lactic acid, acetic acid, and gluconic acid) as monomers for the production of various polymers (adipic acid, lactic acid, acrylic acid, and itaconic acid), as metal chelators (gluconic acid), and as "green" solvents (acetic acid) (Sauer et al., 2008, *Trends in Biotechnology* 26: 100-108). Organic acids may themselves be commercial products or they may be chemical building blocks used in the manufacture of other chemicals. In addition to specialty applications, it has long been recognized that C4-dicarboxylic acids can also serve as building block compounds for the production of large volume industrial chemicals, such as 1,4-butanediol, tetrahydrofuran, and gamma-butyrolactone. The cost of producing these large volume industrial chemicals by traditional petrochemical routes has increased significantly due to the high cost of petroleum derived building blocks.

Organic acids are produced commercially either by chemical synthesis from petroleum derived feedstocks (e.g., fumaric acid, malic acid, acrylic acid, and adipic acid) or by microbial fermentation (e.g., citric acid, lactic acid, gluconic acid, and itaconic acid). Some organic acids such as fumaric acid and malic acid can also be produced by microbial fermentation, but are currently produced commercially by chemical synthesis from petrochemical feedstocks due to lower production costs. However, the rising cost of petroleum derived building block chemicals, the geopolitical instability affecting crude oil prices, and the desire to implement manufacturing processes that utilize feedstocks derived from renewable resources have stimulated a renewed interest in producing organic acids and other chemicals by microbial fermentation.

While malic acid is produced commercially today by chemical synthesis from petrochemical feedstocks, it can also be produced by microbial fermentation. Malic acid has been produced at high levels in genetically engineered yeast (*Saccharomyces cerevisiae*) (Zelle et al., 2008, *Appl. Environ. Microbiol.* 74: 2766-2777) and naturally occurring filamentous fungi such as *Aspergillus* spp. (U.S. Pat. No. 3,063,910; Bercovitz et al., 1990, *Appl. Environ. Microbiol.* 56: 1594-1597). Abe et al. (U.S. Pat. No. 3,063,910) and Bercovitz et al. (1990, *Appl. Environ. Microbiol.* 56: 1594-1597) reported high levels of malic acid production in several species of *Aspergillus*. Moreover, Battat et al. (1991, *Biotechnol. Bioengineering*, 37: 1108-1116) reported malic acid production as high as 113 g/L by *Aspergillus flavus* in a stirred fermentor under optimized conditions. Dicarboxylic acid production by microbial fermentation in yeast is described in WO 2010/003728. Malic acid production by microbial fermentation is also described in WO 2009/011974 and WO 2009/155382. Improvement of malic acid production by genetic engineering of *Aspergillus* will enable economical commercial malic acid production by fermentation.

Malic acid overproduction in *Aspergillus* spp. occurs under specific culture conditions (aerobic conditions and high C:N ratio; calcium carbonate is also added as a neutralizing agent and as source of $CO_2$ for malic acid biosynthesis). Under these conditions, overflow metabolism via the cytosolic, reductive tricarboxylic acid (TCA) cycle results in increased malic acid biosynthesis and secretion into the culture medium. Increased malic acid production has been reported in *Saccharomyces cerevisiae* by increasing the level of pyruvate carboxylase (Bauer et al., 1999, *FEMS Microbiol Lett.* 179: 107-113) or malate dehydrogenase (Pines et al., 1997, *Appl. Microbiol. Biotechnol.* 48: 248-255) using genetic engineering and increasing expression of a malic acid transporter (Zelle et al., 2008, supra). It has been suggested, based on biochemical evidence, that malate dehydrogenase activity is limiting malic acid production in *Aspergillus flavus* strain ATCC 13697 (Peleg et al., 1988, *Appl. Microbiol. Biotechnol.* 28: 69-75). PCT Application No. PCT/US10/47002, entitled "Methods for Improving Malic Acid Production in Filamentous Fungi" filed Aug. 27, 2010, the content of which is hereby incorporated by reference in its entirety, describes malic acid production in filamentous fungi.

It would be advantageous in the art to improve C4-dicarboxylic acid production, such as malic acid production, in *Aspergillus* as a result of genetic engineering using recombinant DNA techniques. The present invention provides, inter alia, polypeptides having C4-dicarboxylic acid transporter activity, polynucleotides encoding the polypeptides, and methods for improving C4-dicarboxylic acid production (e.g., malic acid production).

SUMMARY OF THE INVENTION

The present invention relates to isolated polypeptides having C4-dicarboxylic acid transporter activity. In one aspect the isolated polypeptides having C4-dicarboxylic acid transporter activity are selected from: (a) a polypeptide having at least 65% sequence identity to SEQ ID NO: 2, 4, or 6, or the mature polypeptide sequence thereof; (b) a polypeptide encoded by a polynucleotide that hybridizes under low stringency conditions with SEQ ID NO: 1, 3, or 5, the mature polypeptide coding sequence thereof, or the full-length complementary strand of the foregoing; (c) a polypeptide encoded by a polynucleotide having at least 65% sequence identity to SEQ ID NO: 1, 3, or 5, or the mature polypeptide coding sequence thereof; (d) a variant comprising a substitution, deletion, and/or insertion of one or more (e.g., two, several) amino acids of SEQ ID NO: 2, 4, or 6, or the mature polypeptide sequence thereof; and (e) a fragment of a polypeptide of (a), (b), (c), or (d) that has C4-dicarboxylic acid transporter activity.

The present invention also relates to methods of producing C4-dicarboxylic acids (e.g., malic acid). In one aspect, the method comprises (a) cultivating a host cell (e.g., a filamentous fungal host cell) comprising a heterologous polynucleotide encoding a C4-dicarboxylic acid transporter described herein; and (b) recovering the C4-dicarboxylic acid (e.g., malic acid). In another aspect, the method comprises (a) transforming into host cell (e.g., a filamentous fungal host cell) a heterologous polynucleotide encoding a C4-dicarboxylic acid transporter described herein; (b) cultivating the transformed organism in a medium; and (c) recovering the C4-dicarboxylic acid (e.g., malic acid). In some aspects of the methods, the host cell further comprises a heterologous polynucleotide encoding a malate dehydrogenase and/or a pyruvate carboxylase.

The present invention also relates to a host cell (e.g., a filamentous fungal host cell, such as *Aspergillus oryzae*) comprising a heterologous polynucleotide encoding a C4-dicarboxylic acid transporter described herein wherein the host cell secretes and/or is capable of secreting increased levels of a C4-dicarboxylic acid (e.g., malic acid). In some aspects, the host cell further comprises a heterologous polynucleotide encoding a malate dehydrogenase and/or a pyruvate carboxylase.

The present invention also relates to signal peptides and polynucleotides encoding the same. In one aspect, the invention relates to a polynucleotide encoding a signal peptide comprising or consisting of amino acids 1 to 61 or 1 to 68 of SEQ ID NO: 2 operably linked to a gene encoding a protein. In another aspect, the invention relates to a polynucleotide encoding a signal peptide comprising or consisting of amino acids 1 to 17 of SEQ ID NO: 4 operably linked to a gene encoding a protein. In another aspect, the invention relates to a polynucleotide encoding a signal peptide comprising or consisting of amino acids 1 to 68 of SEQ ID NO: 6 operably linked to a gene encoding a protein.

The present invention also relates to compositions comprising the polypeptides described herein, isolated polynucleotides encoding the polypeptides, nucleic acid constructs, expression vectors, recombinant host cells comprising the polynucleotides, and methods of producing the polypeptides.

BRIEF DESCRIPTION OF THE FIGURES

FIG. 3 shows the genomic DNA sequence and the deduced amino acid sequence of an *Aspergillus aculeatus* C4-dicarboxylic acid transporter gene (c4t737) (SEQ ID NOs: 1 and 2, respectively).
FIG. 5 shows the genomic DNA sequence and the deduced amino acid sequence of an *Aspergillus aculeatus* C4-dicarboxylic acid transporter gene (c4t521) (SEQ ID NOs: 3 and 4, respectively).
FIG. 6 shows the genomic DNA sequence and the deduced amino acid sequence of an *Aspergillus oryzae* NRRL 3488 malate dehydrogenase gene (mdh3) (SEQ ID NOs: 11 and 12, respectively).
FIGS. 8A and 8B together show the genomic DNA sequence and the deduced amino acid sequence of an *Aspergillus oryzae* NRRL 3488 pyruvate carboxylase gene (pyc) (SEQ ID NOs: 15 and 16, respectively).
FIG. 12 shows the genomic DNA sequence and the deduced amino acid sequence of an *Aspergillus aculeatus* C4-dicarboxylic acid transporter gene (mat737) (SEQ ID NOs: 5 and 6, respectively).

DEFINITIONS

Figure 1:
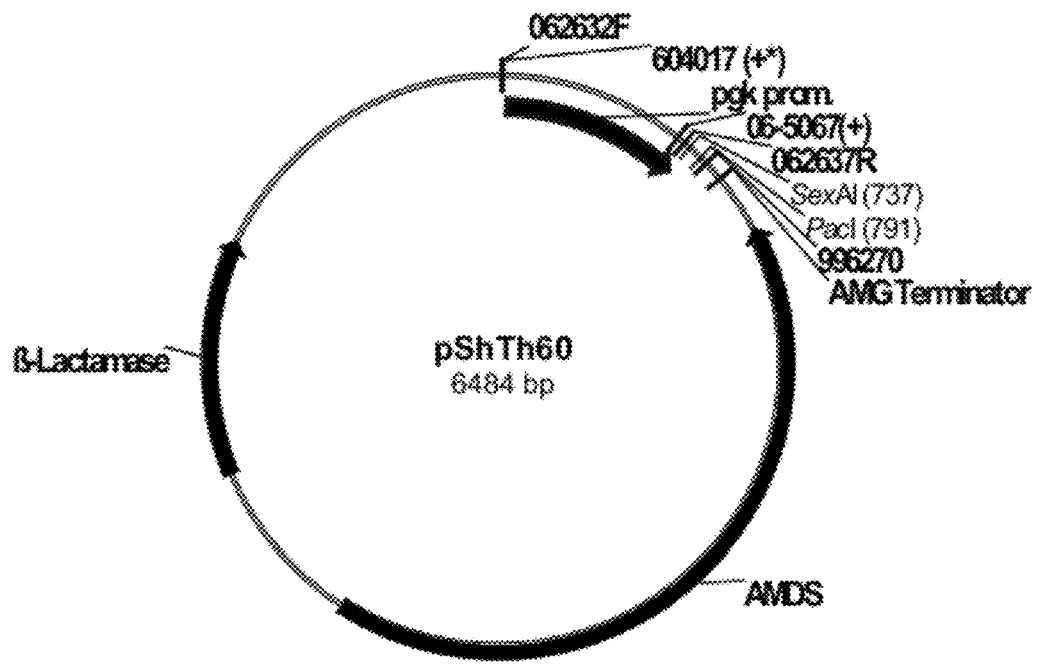
FIG. 1 shows a restriction map of pShTh60.

C4-dicarboxylic acid transporter: The term "C4-dicarboxylic acid transporter" is defined herein as a dicarboxylic acid permease that can transport malic acid, succinic acid, oxaloacetic acid, malonic acid, and/or fumaric acid outside a cell (Grobler et al., 1995, Yeast 11: 1485-1491; Camarasa et al., 2001, *Applied and Environmental Microbiology* 67: 4144-4151). A computational method to predict mitochondrially imported proteins and their targeting sequences is described by Claros and Vincens, 1996, *Eur. J. Biochem.* 241: 779-786. In some aspects, the C4-dicarboxylic acid transporters have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the C4-dicarboxylic acid transporter activity (e.g., malic acid transporter activity) of the mature polypeptide SEQ ID NO: 2, SEQ ID NO: 4, and/or SEQ ID NO: 6.

Malate dehydrogenase: The term "malate dehydrogenase" is defined herein as a malate:$NAD^+$ oxidoreductase (EC 1.1.1.37) that catalyzes the reduction of oxaloacetate in the presence of $NADH+H^+$ to malate and $NAD^+$. For purposes of the present invention, malate dehydrogenase activity is determined according to the following procedure. The assay solution consists of 1 mM oxaloacetic acid, 100 mM Tris pH 8.0, 10 mM $NaHCO_3$, 5 mM $MgCl_2$, and 0.1 mM NADH (Sigma Chemical Co., St. Louis, Mo., USA). The assay solution without oxaloacetic acid as substrate is run as a control to measure background NADH degradation rates. Dilutions of 1/100, 1/500, 1/2500, and 1/12500 of each supernatant are prepared with double-distilled water. Aliquots of 270 µl of the assay solution are dispensed into 96 well polystyrene flat bottom plates. A 30 µl sample of each diluted supernatant is added to initiate the assay. The reactions are monitored using a SPECTRAMAX® 340PC plate reader (Molecular Devices, Sunnyvale, Calif., USA) with the following settings: 340 nm, kinetic reading. A concentration series of NADH is used to construct a standard curve and a dilution series of purified malic dehydrogenase (Sigma Chemical Co., St. Louis, Mo., USA) is used as a positive control. One unit of malate dehydrogenase activity equals the amount of enzyme capable of converting 1 µmole of oxaloacetate and $NADH+H^+$ to malate and $NAD^+$ per minute at pH 8.0, 25° C.

In some aspects, the malate dehydrogenases have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the malate dehydrogenase activity of the mature polypeptide SEQ ID NO: 12.

Pyruvate carboxylase: The term "pyruvate carboxylase" is defined herein as a pyruvate:carbon-dioxide ligase (ADP-forming) (EC 6.4.1.1) that catalyzes the carboxylation of pyruvate in the presence of ATP and $HCO_3^-$ to oxaloacetate, ADP, and phosphate. For purposes of the present invention, pyruvate carboxylase activity is determined according to the procedure of the SIGMA® Quality Control Test procedure for pyruvate carboxylase (Sigma Chemical Co., St. Louis, Mo., USA) except the assay uses Tris buffer at pH 8.0. One unit of pyruvate carboxylase activity equals the amount of enzyme capable of converting 1 μmole of pyruvate and $CO_2$ to oxaloacetate per minute at pH 7.8, 30° C.

In some aspects, the pyruvate carboxylases have at least 20%, e.g., at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% of the pyruvate carboxylase activity of the mature polypeptide SEQ ID NO: 16.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide whose expression is quantitatively altered by the introduction of one or more (e.g., two, several) extra copies of the polynucleotide into the host cell.

Isolated/purified: The terms "isolated" and "purified" mean a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, at least 93% pure, at least 95% pure, at least 97% pure, at least 98% pure, or at least 99% pure, as determined by SDS-PAGE and a polynucleotide may be at least 1% pure, e.g., at least 5% pure, at least 10% pure, at least 20% pure, at least 40% pure, at least 60% pure, at least 80% pure, at least 90% pure, at least 93% pure, at least 95% pure, at least 97% pure, at least 98% pure, or at least 99% pure, as determined by agarose electrophoresis.

Coding sequence: The term "coding sequence" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

cDNA sequence: The term "cDNA sequence" means a sequence of DNA following reverse transcription from a mature, spliced, mRNA molecule obtained from a eukaryotic cell. The initial, primary RNA transcript from genomic DNA is a precursor to mRNA that is processed through a series of steps, including splicing, before appearing as mature spliced mRNA. A cDNA sequence lacks intervening intron sequences that may be present in the corresponding genomic DNA sequence. Accordingly, the phrase "the cDNA sequence of SEQ ID NO: X" intends the resulting sequence after the intervening intron sequences of SEQ ID NO: X, if present, are removed. In some instances—when a referenced genomic DNA sequence lacks intervening intron sequences—a cDNA sequence may be identical to its corresponding genomic DNA sequence.

Genomic DNA sequence: The term "genomic DNA sequence" means a DNA sequence found in the genome of a source organism (e.g., a eukaryotic or prokaryotic genome). In some instances, a genomic DNA sequence from a eukaryotic genome contains one or more intervening intron sequences that are removed from the primary RNA transcript as a result of RNA splicing. Accordingly, the phrase "the genomic DNA sequence of SEQ ID NO: Y" intends the corresponding DNA sequence from the source organism which includes intervening intron sequences, if any, that are present before RNA splicing.

Mature polypeptide sequence: The term "mature polypeptide sequence" means the portion of the referenced polypeptide sequence after any post-translational sequence modifications (such as N-terminal processing and/or C-terminal truncation). In some instances, the mature polypeptide sequence may be identical to the entire referenced polypeptide sequence. In one aspect, the mature polypeptide sequence is amino acids 69 to 397 of SEQ ID NO: 2 based on the InterProScan program (The European Bioinformatics Institute) that predicts amino acids 1 to 68 of SEQ ID NO: 2 are a signal peptide. In another aspect, the mature polypeptide sequence is amino acids 62 to 397 of SEQ ID NO: 2 based on the SignalP program (Nielsen et al., 1997, *Protein Engineering* 10:1-6) that predicts amino acids 1 to 61 of SEQ ID NO: 2 are a signal peptide. In another aspect, the mature polypeptide sequence is amino acids 18 to 418 of SEQ ID NO: 4 based on the SignalP program that predicts amino acids 1 to 17 of SEQ ID NO: 4 are a signal peptide. In another aspect, the mature polypeptide sequence is amino acids 1 to 418 of SEQ ID NO: 4 based on the InterProScan program that predicts there is no signal peptide. In another aspect, the mature polypeptide sequence is amino acids 69 to 397 of SEQ ID NO: 6 based on the InterProScan program that predicts amino acids 1 to 68 of SEQ ID NO: 6 are a signal peptide.

Mature polypeptide coding sequence: The term "mature polypeptide coding sequence" means the portion of the referenced polynucleotide sequence (e.g., genomic or cDNA sequence) that encodes a mature polypeptide sequence. In some instances, the mature polypeptide coding sequence may be identical to the entire referenced polynucleotide sequence. In one aspect, the mature polypeptide coding sequence is nucleotides 205 to 1194 of SEQ ID NO: 1 based on the InterProScan program (The European Bioinformatics Institute) that predicts nucleotides 1 to 204 of SEQ ID NO: 1 encode a signal peptide. In another aspect, the mature polypeptide coding sequence is nucleotides 184 to 1194 of SEQ ID NO: 1 based on the SignalP program (Nielsen et al., 1997, *Protein Engineering* 10:1-6) that predicts nucleotides 1 to 183 of SEQ ID NO: 1 encode a signal peptide. In another aspect, the mature polypeptide coding sequence is nucleotides 52 to 1257 of SEQ ID NO: 3 based on the SignalP program that predicts nucleotides 1 to 51 of SEQ ID NO: 3 encode a signal peptide. In another aspect, the mature polypeptide coding sequence is nucleotides 1 to 1257 of SEQ ID NO: 3 based on the InterProScan program that predicts no signal peptide. In another aspect, the mature polypeptide coding sequence is nucleotides 205 to 1194 of SEQ ID NO: 5 based on the InterProScan program that predicts nucleotides 1 to 204 of SEQ ID NO: 5 encode a signal peptide.

Fragment: The term "fragment" means a polypeptide having one or more (e.g., two, several) amino acids deleted from the amino and/or carboxyl terminus of a referenced polypeptide sequence. In one aspect, the fragment has C4-dicarboxylic acid transporter activity. In another aspect, a fragment contains at least 337 amino acid residues, e.g., at least 357 amino acid residues, or at least 377 amino acid residues of SEQ ID NO: 2. In another aspect, a fragment contains at least 355 amino acid residues, e.g., at least 375 amino acid residues or at least 395 amino acid residues of SEQ ID NO: 4. In another aspect, a fragment contains at least 337 amino acid residues, e.g., at least 357 amino acid residues or at least 377 amino acid residues of SEQ ID NO: 6.

Subsequence: The term "subsequence" means a polynucleotide having one or more (e.g., two, several) nucleotides deleted from the 5' and/or 3' end of the referenced nucleotide sequence. In one aspect, the subsequence encodes a fragment having C4-dicarboxylic acid transporter activity. In another aspect, a subsequence contains at least 1011 nucleotides, e.g., at least 1171 nucleotides, or at least 1131 nucleotides of SEQ ID NO: 1. In another aspect, a subsequence contains at least 1065 nucleotides, e.g., at least 1125 nucleotides, or at least 1185 nucleotides of SEQ ID NO: 3. In another aspect, a subsequence contains at least 1011 nucleotides, e.g., at least 1171 nucleotides or at least 1131 nucleotides of SEQ ID NO: 5.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Expression: The term "expression" includes any step involved in the production of the polypeptide including, but not limited to, transcription, post-transcriptional modification, translation, post-translational modification, and secretion.

Nucleic acid construct: The term "nucleic acid construct" means a nucleic acid molecule—single-stranded or double-stranded—which is isolated from a naturally occurring gene, modified to contain segments of nucleic acids in a manner that would not otherwise exist in nature, or synthetic, wherein the nucleic acid molecule comprises one or more (e.g., two, several) control sequences.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression vector: The term "expression vector" means a linear or circular DNA molecule that comprises a polynucleotide encoding a polypeptide and is operably linked to control sequences, wherein the control sequences provide for expression of the polynucleotide encoding the polypeptide. At a minimum, the expression vector comprises a promoter sequence, and transcriptional and translational stop signal sequences.

Host cell: The term "host cell" means any cell type that is susceptible to transformation, transfection, transduction, and the like with a nucleic acid construct or expression vector comprising a polynucleotide of the present invention (e.g., a polynucleotide encoding a C4-dicarboxylic acid transporter). The term "host cell" encompasses any progeny of a parent cell that is not identical to the parent cell due to mutations that occur during replication.

Variant: The term "variant" means a polypeptide having activity, e.g., C4-dicarboxylic acid transporter activity, comprising an alteration, i.e., a substitution, insertion, and/or deletion of one or more (e.g., two, several) amino acid residues at one or more positions. A substitution means a replacement of an amino acid occupying a position with a different amino acid; a deletion means removal of an amino acid occupying a position; and an insertion means adding one or more, e.g., 1-3 amino acids, adjacent to an amino acid occupying a position.

Volumetric productivity: The term "volumetric productivity" refers to the amount of referenced product produced (e.g., the amount of a C4-dicarboxylic acid produced) per volume of the system used (e.g., the total volume of media and contents therein) per unit of time.

Fermentable medium: The term "fermentable medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as a C4-dicarboxylic acid. In some instances, the fermentation medium is derived from a natural source, such as sugar cane, starch, or cellulose, and may be the result of pretreating the source by enzymatic hydrolysis (saccharification).

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

Polypeptides Having C4-Dicarboxylic Acid Transporter Activity

The present invention relates to isolated polypeptides having C4-dicarboxylic acid transporter activity. In one aspect the isolated polypeptides having C4-dicarboxylic acid transporter activity are selected from:

(a) a polypeptide having at least 65% sequence identity to SEQ ID NO: 2, 4, or 6, or the mature polypeptide sequence thereof;

(b) a polypeptide encoded by a polynucleotide that hybridizes under low stringency conditions with SEQ ID NO: 1, 3, or 5; the mature polypeptide coding sequence thereof, or the full-length complementary strand of the foregoing;

(c) a polypeptide encoded by a polynucleotide having at least 65% sequence identity to SEQ ID NO: 1, 3, or 5, or the mature polypeptide coding sequence thereof;

(d) a variant comprising a substitution, deletion, and/or insertion of one or more (e.g., two, several) amino acids of SEQ ID NO: 2, 4, or 6, or the mature polypeptide sequence thereof; and (e) a fragment of a polypeptide of (a), (b), (c), or (d) that has C4-dicarboxylic acid transporter activity.

In another aspect the isolated polypeptides having C4-dicarboxylic acid transporter activity are selected from:

(a) a polypeptide having at least 65% sequence identity to SEQ ID NO: 2, or the mature polypeptide sequence thereof;

(b) a polypeptide encoded by a polynucleotide that hybridizes under low stringency conditions with SEQ ID NO: 1, the mature polypeptide coding sequence thereof, or the full-length complementary strand of the foregoing;

(c) a polypeptide encoded by a polynucleotide having at least 65% sequence identity to SEQ ID NO: 1, or the mature polypeptide coding sequence thereof;

(d) a variant comprising a substitution, deletion, and/or insertion of one or more (e.g., two, several) amino acids of SEQ ID NO: 2, of the mature polypeptide sequence thereof; and (e) a fragment of a polypeptide of (a), (b), (c), or (d) that has C4-dicarboxylic acid transporter activity.

In another aspect the isolated polypeptides having C4-dicarboxylic acid transporter activity are selected from:

(a) a polypeptide having at least 65% sequence identity to SEQ ID NO: 4, or the mature polypeptide sequence thereof;

(b) a polypeptide encoded by a polynucleotide that hybridizes under low stringency conditions with SEQ ID NO: 3, the mature polypeptide coding sequence thereof, or the full-length complementary strand of the foregoing;

(c) a polypeptide encoded by a polynucleotide having at least 65% sequence identity to SEQ ID NO: 3, or the mature polypeptide coding sequence thereof;

(d) a variant comprising a substitution, deletion, and/or insertion of one or more (e.g., two, several) amino acids of SEQ ID NO: 4, of the mature polypeptide sequence thereof; and (e) a fragment of a polypeptide of (a), (b), (c), or (d) that has C4-dicarboxylic acid transporter activity.

In another aspect the isolated polypeptides having C4-dicarboxylic acid transporter activity are selected from:

(a) a polypeptide having at least 65% sequence identity to SEQ ID NO: 6, or the mature polypeptide sequence thereof;

(b) a polypeptide encoded by a polynucleotide that hybridizes under low stringency conditions with SEQ ID NO: 5, the mature polypeptide coding sequence thereof, or the full-length complementary strand of the foregoing;

(c) a polypeptide encoded by a polynucleotide having at least 65% sequence identity to SEQ ID NO: 5, or the mature polypeptide coding sequence thereof;

(d) a variant comprising a substitution, deletion, and/or insertion of one or more (e.g., two, several) amino acids of SEQ ID NO: 6, of the mature polypeptide sequence thereof; and (e) a fragment of a polypeptide of (a), (b), (c), or (d) that has C4-dicarboxylic acid transporter activity.

In some of these aspects, the isolated polypeptide has an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, sequence identity to SEQ ID NO: 2, or the mature polypeptide sequence thereof, which has C4-dicarboxylic acid transporter activity. In one aspect, the polypeptide comprises an amino acid sequence that differs by no more than ten amino acids, e.g., by five amino acids, by four amino acids, by three amino acids, by two amino acids, or by one amino acid from SEQ ID NO: 2, or the mature polypeptide sequence thereof.

In one aspect, the polypeptide comprises or consists of the amino acid sequence of SEQ ID NO: 2, the mature polypeptide sequence of SEQ ID NO: 2, an allelic variant thereof, or a fragment of the foregoing, having C4-dicarboxylic acid transporter activity. In another aspect, the polypeptide comprises or consists of the amino acid sequence of SEQ ID NO: 2. In another aspect, the polypeptide comprises or consists of the mature polypeptide sequence of SEQ ID NO: 2. In another preferred aspect, the polypeptide comprises or consists of amino acids 62 to 397 or 69 to 397 of SEQ ID NO: 2.

In some of these aspects, the isolated polypeptide has an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, sequence identity to SEQ ID NO: 4, or the mature polypeptide sequence thereof, which has C4-dicarboxylic acid transporter activity. In one aspect, the polypeptide comprises an amino acid sequence that differs by no more than ten amino acids, e.g., by five amino acids, by four amino acids, by three amino acids, by two amino acids, or by one amino acid from SEQ ID NO: 4, or the mature polypeptide sequence thereof.

In one aspect, the polypeptide comprises or consists of the amino acid sequence of SEQ ID NO: 4, the mature polypeptide sequence of SEQ ID NO: 4, an allelic variant thereof, or a fragment of the foregoing, having C4-dicarboxylic acid transporter activity. In another aspect, the polypeptide comprises or consists of the amino acid sequence of SEQ ID NO: 4. In another aspect, the polypeptide comprises or consists of the mature polypeptide sequence of SEQ ID NO: 4. In another preferred aspect, the polypeptide comprises or consists of amino acids 52 to 418 of SEQ ID NO: 4.

In some of these aspects, the isolated polypeptide has an amino acid sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, sequence identity to SEQ ID NO: 6, or the mature polypeptide sequence thereof, which has C4-dicarboxylic acid transporter activity. In one aspect, the polypeptide comprises an amino acid sequence that differs by no more than ten amino acids, e.g., by five amino acids, by four amino acids, by three amino acids, by two amino acids, or by one amino acid from SEQ ID NO: 6, or the mature polypeptide sequence thereof.

In one aspect, the polypeptide comprises or consists of the amino acid sequence of SEQ ID NO: 6, the mature polypeptide sequence of SEQ ID NO: 6, an allelic variant thereof, or a fragment of the foregoing, having C4-dicarboxylic acid transporter activity. In another aspect, the polypeptide comprises or consists of the amino acid sequence of SEQ ID NO: 6. In another aspect, the polypeptide comprises or consists of the mature polypeptide sequence of SEQ ID NO: 6. In another aspect, the polypeptide comprises or consists of amino acids 69 to 397 of SEQ ID NO: 6.

In one aspect, the isolated polypeptides having C4-dicarboxylic acid transporter activity are encoded by polynucleotides that hybridize under very low stringency conditions, low stringency conditions, medium stringency conditions, medium-high stringency conditions, high stringency conditions, or very high stringency conditions with SEQ ID NO: 1, the mature polypeptide coding sequence thereof, or the full-length complementary strand of the foregoing (J. Sambrook, E. F. Fritsch, and T. Maniatis, 1989, *Molecular Cloning, A Laboratory Manual,* 2d edition, Cold Spring Harbor, N.Y.).

In another aspect, the isolated polypeptides having C4-dicarboxylic acid transporter activity are encoded by polynucleotides that hybridize under very low stringency conditions, low stringency conditions, medium stringency conditions, medium-high stringency conditions, high stringency conditions, or very high stringency conditions with SEQ ID NO: 3, the mature polypeptide coding sequence thereof, or the full-length complementary strand of the foregoing.

In another aspect, the isolated polypeptides having C4-dicarboxylic acid transporter activity are encoded by polynucleotides that hybridize under very low stringency conditions, low stringency conditions, medium stringency conditions, medium-high stringency conditions, high stringency conditions, or very high stringency conditions with SEQ ID NO: 5, the mature polypeptide coding sequence thereof, or the full-length complementary strand of the foregoing.

In another aspect, the isolated polypeptides having C4-dicarboxylic acid transporter activity are encoded by polynucleotides having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 1, 3, or 5, the mature polypeptide coding sequence thereof, or the full-length complementary strand of the foregoing.

In one aspect, the isolated polypeptides having C4-dicarboxylic acid transporter activity is encoded by polynucleotides having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 1, the mature polypeptide coding sequence thereof, or the full-length complementary strand of the foregoing.

In one aspect, the isolated polypeptides having C4-dicarboxylic acid transporter activity is encoded by polynucleotides having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 3, the mature polypeptide coding sequence thereof, or the full-length complementary strand of the foregoing.

In one aspect, the isolated polypeptides having C4-dicarboxylic acid transporter activity is encoded by polynucleotides having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 5, the mature polypeptide coding sequence thereof, or the full-length complementary strand of the foregoing.

In one aspect, the polypeptide is encoded by SEQ ID NO: 1, 3, or 5, or the mature polypeptide coding sequence thereof. In one aspect, the polypeptide is encoded by SEQ ID NO: 1 or the mature polypeptide coding sequence thereof. In one aspect, the polypeptide is encoded by SEQ ID NO: 1. In one aspect, the polypeptide is encoded by SEQ ID NO: 3 or the mature polypeptide coding sequence thereof. In one aspect, the polypeptide is encoded by SEQ ID NO: 3. In one aspect, the polypeptide is encoded by SEQ ID NO: 5 or the mature polypeptide coding sequence thereof. In one aspect, the polypeptide is encoded by SEQ ID NO: 5. In one aspect, the polypeptide is encoded by a subsequence of SEQ ID NO: 1, 3, or 5, wherein the subsequence encodes a polypeptide having C4-dicarboxylic acid transporter activity. In one aspect, the polypeptide is encoded by a subsequence of SEQ ID NO: 1, wherein the subsequence encodes a polypeptide having C4-dicarboxylic acid transporter activity. In one aspect, the polypeptide is encoded by a subsequence of SEQ ID NO: 3, wherein the subsequence encodes a polypeptide having C4-dicarboxylic acid transporter activity. In one aspect, the polypeptide is encoded by a subsequence of SEQ ID NO: 5, wherein the subsequence encodes a polypeptide having C4-dicarboxylic acid transporter activity.

In one aspect, the isolated polypeptide is a variant comprising a substitution, deletion, and/or insertion of one or more (e.g., two, several) amino acids of SEQ ID NO: 2, 4, or 6, or the mature polypeptide sequence thereof. In one aspect, the polypeptide is a variant comprising a substitution, deletion, and/or insertion of one or more amino acids of SEQ ID NO: 2. In one aspect, the polypeptide is a variant comprising a substitution, deletion, and/or insertion of one or more amino acids of the mature polypeptide sequence of SEQ ID NO: 2. In one aspect, the polypeptide is a variant comprising a substitution, deletion, and/or insertion of one or more amino acids of SEQ ID NO: 4. In one aspect, the polypeptide is a variant comprising a substitution, deletion, and/or insertion of one or more amino acids of the mature polypeptide sequence of SEQ ID NO: 4. In one aspect, the polypeptide is a variant comprising a substitution, deletion, and/or insertion of one or more amino acids of SEQ ID NO: 6. In one aspect, the polypeptide is a variant comprising a substitution, deletion, and/or insertion of one or more amino acids of the mature polypeptide sequence of SEQ ID NO: 6.

Preferably, amino acid changes are of a minor nature, that is conservative amino acid substitutions or insertions that do not significantly affect the folding and/or activity of the protein; small deletions, typically of one to about 30 amino acids; small amino-terminal or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for C4-dicarboxylic acid transporter activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In some aspects, the total number of amino acid substitutions, deletions and/or insertions of SEQ ID NO: 2, 4, or 6, or the mature polypeptide sequence thereof, is not more than 10, e.g., not more than 1, 2, 3, 4, 5, 6, 7, 8 or 9.

In another aspect, the polypeptide is a fragment of SEQ ID NO: 2, 4, or 6, or the mature polypeptide sequence thereof, wherein the fragment has C4-dicarboxylic acid transporter activity. In one aspect, the polypeptide is a fragment of SEQ ID NO: 2 or the mature polypeptide sequence thereof, wherein the fragment has C4-dicarboxylic acid transporter activity. In one aspect, the fragment contains at least 337 amino acid residues, e.g., at least 357 amino acid residues, or at least 377 amino acid residues of SEQ ID NO: 2. In another aspect, the polypeptide is a fragment of SEQ ID NO: 4 or the mature polypeptide sequence thereof, wherein the fragment has C4-dicarboxylic acid transporter activity. In one aspect, the fragment contains at least 355 amino acid residues, e.g., at least 375 amino acid residues, or at least 395 amino acid residues of SEQ ID NO: 4. In another aspect, the polypeptide is a fragment of SEQ ID NO: 6 or the mature polypeptide sequence thereof, wherein the fragment has C4-dicarboxylic acid transporter activity. In one aspect, the fragment contains at least 337 amino acid residues, e.g., at least 357 amino acid residues, or at least 377 amino acid residues of SEQ ID NO: 6.

The polypeptide may be a hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having C4-Dicarboxylic Acid Transporter Activity

A polypeptide having C4-dicarboxylic acid transporter activity of the present invention (e.g., a polypeptide of SEQ ID NO: 2, 4, or 6, or the mature polypeptide sequence thereof) may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* polypeptide having C4-dicarboxylic acid transporter activity, or a gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide.

In another aspect, the polypeptide is a *Streptococcus equisimilis, Streptococcus pyogenes, Streptococcus uberis,* or *Streptococcus equi* subsp. *Zooepidemicus* polypeptide.

In another aspect, the polypeptide is a *Streptomyces achromogenes, Streptomyces avermitilis, Streptomyces coelicolor, Streptomyces griseus,* or *Streptomyces lividans* polypeptide.

The polypeptide may also be a fungal polypeptide. For example, the polypeptide may be a yeast polypeptide such as a *Candida, Kluyveromyces, Pichia, Saccharomyces, Schizosaccharomyces,* or *Yarrowia* polypeptide; or a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* polypeptide.

In another aspect, the polypeptide is an *Aspergillus* polypeptide, e.g., an *Aspergillus aculeatus* polypeptide, such as an *Aspergillus aculeatus* polypeptide from *E. coli* NRRL B-50400, *E. coli* NRRL B-50388, or *E. coli* NRRL B-50401.

In another aspect, the polypeptide is an *Aspergillus aculeatus* polypeptide of SEQ ID NO: 2 or SEQ ID NO: 4. In another aspect, the polypeptide is an *Aspergillus aculeatus* polypeptide of SEQ ID NO: 2. In another aspect, the polypeptide is an *Aspergillus aculeatus* polypeptide of SEQ ID NO: 4.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding a polypeptide of the present invention (e.g., an isolated polynucleotide encoding a polypeptide of any aspect related to SEQ ID NO: 2, 4, or 6).

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus* (e.g., *Aspergillus aculeatus*), or another or related organism and thus, for example, may be an allelic or species variant of the polypeptide encoding region of the nucleotide sequence.

The present invention also relates to an isolated polynucleotide comprising or consisting of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, sequence identity to SEQ ID NO: 1, 3, or 5, or the mature polypeptide coding sequence thereof, which encodes a polypeptide having C4-dicarboxylic acid transporter activity.

In one aspect, the isolated polynucleotide comprises or consists of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, sequence identity to SEQ ID NO: 1 or the mature polypeptide coding sequence thereof, which encodes a polypeptide having C4-dicarboxylic acid transporter activity.

In one aspect, the isolated polynucleotide comprises or consists of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, sequence identity to SEQ ID NO: 3 or the mature polypeptide coding sequence thereof, which encodes a polypeptide having C4-dicarboxylic acid transporter activity.

In one aspect, the isolated polynucleotide comprises or consists of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, sequence identity to SEQ ID NO: 5 or the mature polypeptide coding sequence thereof, which encodes a polypeptide having C4-dicarboxylic acid transporter activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1, 3, or 5, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under very low stringency conditions, low stringency conditions, medium stringency conditions, medium-high stringency conditions, high stringency conditions, or very high stringency conditions with SEQ ID NO: 1, 3, or 5; the mature polypeptide coding sequence of SEQ ID NO: 1, 3, or 5; the full-length complementary strand thereof; or an allelic variant or subsequence of the foregoing (Sambrook et al., 1989, supra), as defined herein.

In one aspect, the isolated polynucleotide hybridizes under very low stringency conditions, low stringency conditions, medium stringency conditions, medium-high stringency conditions, high stringency conditions, or very high stringency conditions with SEQ ID NO: 1; the mature polypeptide coding sequence of SEQ ID NO: 1; the full-length complementary strand thereof; or an allelic variant or subsequence of the foregoing (Sambrook et al., 1989, supra), as defined herein.

In one aspect, the isolated polynucleotide hybridizes under very low stringency conditions, low stringency conditions, medium stringency conditions, medium-high stringency conditions, high stringency conditions, or very high stringency conditions with SEQ ID NO: 1; the mature polypeptide coding sequence of SEQ ID NO: 3; the full-length complementary strand thereof; or an allelic variant or subsequence of the foregoing (Sambrook et al., 1989, supra), as defined herein.

In one aspect, the isolated polynucleotide hybridizes under very low stringency conditions, low stringency conditions, medium stringency conditions, medium-high stringency conditions, high stringency conditions, or very high stringency conditions with SEQ ID NO: 1; the mature polypeptide coding sequence of SEQ ID NO: 5; the full-length complementary strand thereof; or an allelic variant or subsequence of the foregoing (Sambrook et al., 1989, supra), as defined herein.

In one aspect, the polynucleotide comprises or consists of SEQ ID NO: 1, the mature polypeptide coding sequence of SEQ ID NO: 1, or the sequence contained in plasmid pAaC4T737 which is contained in *E. coli* NRRL B-50400, or a subsequence of SEQ ID NO: 1 that encodes a fragment of SEQ ID NO: 2 having C4-dicarboxylic acid transporter activity (e.g., amino acids 69-397 or 62 to 397 of SEQ ID NO: 2), such as the polynucleotide of nucleotides 205 to 1194 or 184 to 1194 of SEQ ID NO: 1.

In another aspect, the polynucleotide comprises or consists of SEQ ID NO: 3, the mature polypeptide coding sequence of SEQ ID NO: 3, or the sequence contained in plasmid pAaC4T521 which is contained in *E. coli* NRRL B-50388, or a subsequence of SEQ ID NO: 3 that encodes a fragment of SEQ ID NO: 4 having C4-dicarboxylic acid transporter activity (e.g., amino acids 18-418 of SEQ ID NO: 4), such as the polynucleotide of nucleotides 52 to 1257 of SEQ ID NO: 3.

In another aspect, the polynucleotide comprises or consists of SEQ ID NO: 5, the mature polypeptide coding sequence of SEQ ID NO: 5, or the sequence contained in plasmid pAaMAT737 which is contained in *E. coli* NRRL B-50401, or a subsequence of SEQ ID NO: 5 that encodes a fragment of SEQ ID NO: 6 having C4-dicarboxylic acid transporter activity (e.g., amino acids 69-397 of SEQ ID NO: 6), such as the polynucleotide of nucleotides 205 to 1194 of SEQ ID NO: 5.

The polynucleotide of SEQ ID NO: 1, 3, or 5, or a subsequence thereof; as well as the amino acid sequence of SEQ ID NO: 2, 4, or 6, or a fragment thereof; may be used to design nucleic acid probes to identify and clone DNA encoding polypeptides having C4-dicarboxylic acid transporter activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having C4-dicarboxylic acid transporter activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, 3, or 5, or a subsequence thereof, the carrier material is preferably used in a Southern blot.

For purposes of the present invention, hybridization indicates that the polynucleotide hybridizes to a labeled nucleic acid probe corresponding SEQ ID NO: 1, 3, or 5; the mature polypeptide coding sequence of SEQ ID NO: 1, 3, or 5; a full-length complementary strand thereof; or a subsequence of the foregoing; under very low to very high stringency conditions. Molecules to which the nucleic acid probe hybridizes under these conditions can be detected using, for example, X-ray film.

In one aspect, the nucleic acid probe is SEQ ID NO: 1, 3, or 5. In one aspect, the nucleic acid probe is the mature polypeptide coding sequence of SEQ ID NO: 1, 3, or 5. In another aspect, the nucleic acid probe is a polynucleotide that encodes the polypeptide of SEQ ID NO: 2, 4, or 6, or a fragment thereof. In another aspect, the nucleic acid probe is SEQ ID NO: 1. In another aspect, the nucleic acid probe is SEQ ID NO: 3. In another aspect, the nucleic acid probe is SEQ ID NO: 5. In another aspect, the nucleic acid probe is the polynucleotide contained in plasmid pAaC4T737 which is contained in *E. coli* NRRL B-50400, wherein the polynucleotide encodes a polypeptide having C4-dicarboxylic acid transporter activity. In another aspect, the nucleic acid probe is the mature polypeptide coding sequence contained in plasmid pAaC4T737 which is contained in *E. coli* NRRL B-50400, wherein the polypeptide has C4-dicarboxylic acid transporter activity. In another aspect, the nucleic acid probe is the polynucleotide contained in plasmid pAaC4T521 which is contained in *E. coli* NRRL B-50388, wherein the polynucleotide encodes a polypeptide having C4-dicarboxylic acid transporter activity. In another aspect, the nucleic acid probe is the mature polypeptide coding sequence contained in plasmid pAaC4T521 which is contained in *E. coli* NRRL B-50388, wherein the polypeptide has C4-dicarboxylic acid transporter activity. In another aspect, the nucleic acid probe is the polynucleotide contained in plasmid pAaMAT737 which is contained in *E. coli* NRRL B-50401, wherein the polynucleotide encodes a polypeptide having C4-dicarboxylic acid transporter activity. In another aspect, the nucleic acid probe is the mature polypeptide coding sequence contained in plasmid pAaMAT737 which is contained in *E. coli* NRRL B-50401, wherein the polypeptide has C4-dicarboxylic acid transporter activity.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

Nucleic Acid Constructs

The present invention also relates to nucleic acid constructs comprising a polynucleotide of the present invention operably linked to one or more (e.g., two, several) control sequences that direct the expression of the coding sequence in a suitable host cell under conditions compatible with the control sequences. The present invention also embraces recombinant host cells and methods utilizing nucleic acid constructs comprising a heterologous polynucleotide encoding a C4-dicarboxylic acid transporter described herein (and/or a malate dehydrogenase, or a pyruvate carboxylase described herein) linked to one or more control sequences that direct expression in a suitable host cell under conditions compatible with the control sequence(s). Such nucleic acid constructs may be used in any of the host cells and methods describe herein.

The polynucleotides described herein may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Each polynucleotide described herein may be operably linked to a promoter that is foreign to the polynucleotide. For example, in one aspect, the heterologous polynucleotide encoding a C4-dicarboxylic acid transporter is operably linked to a promoter that is foreign to the polynucleotide. In another aspect, the heterologous polynucleotide encoding a malate dehydrogenase is operably linked to promoter foreign to the polynucleotide. In another aspect, the heterologous polynucleotide encoding a pyruvate carboxylase is operably linked to promoter foreign to the polynucleotide.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in *Aspergilli* in which the untranslated leader has been replaced by an untranslated leader from a gene encoding triose phosphate isomerase in *Aspergilli*; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases).

A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The present invention also embraces recombinant host cells and methods utilizing recombinant expression vectors comprising a heterologous polynucleotide encoding a C4-dicarboxylic acid transporter (and/or a malate dehydrogenase or a pyruvate carboxylase); as well as a promoter; and transcriptional and translational stop signals. Such recombinant expression vectors may be used in any of the host cells and methods described herein.

The various nucleotide and control sequences may be joined together to produce a recombinant expression vector that may include one or more (e.g., two, several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

In one aspect, each polynucleotide encoding a C4-dicarboxylic acid transporter, a malate dehydrogenase, and/or a pyruvate carboxylase described herein is contained on an independent vector. In one aspect, at least two of the polynucleotides are contained on a single vector. In one aspect, all the polynucleotides encoding the C4-dicarboxylic acid transporter, the malate dehydrogenase, and the pyruvate carboxylase are contained on a single vector.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., two, several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Malate Dehydrogenases and Polynucleotides Encoding Malate Dehydrogenases

In some aspects of the recombinant host cells and methods of use thereof, the host cells have malate dehydrogenase activity. In some aspects, the host cells comprise a heterologous polynucleotide encoding a malate dehydrogenase. The malate dehydrogenase can be any malate dehydrogenase that is suitable for practicing the invention. In one aspect, the malate dehydrogenase is an enzyme that is present in the cytosol of the host cell.

In one aspect of the recombinant host cells and methods described herein, the malate dehydrogenase is (a) a malate dehydrogenase having at least 60% sequence identity to SEQ ID NO: 12 or the mature polypeptide sequence thereof; (b) a malate dehydrogenase encoded by a polynucleotide that hybridizes under low stringency conditions with (i) SEQ ID NO: 11 or the mature polypeptide coding sequence thereof, (ii) the cDNA sequence of SEQ ID NO: 11 or the mature polypeptide coding sequence thereof, or (iii) the full-length complementary strand of (i) or (ii); (c) a malate dehydrogenase encoded by a polynucleotide having at least 60% sequence identity to (iv) SEQ ID NO: 11 or the mature polypeptide coding sequence thereof, (v) the cDNA sequence of SEQ ID NO: 11 or the mature polypeptide coding sequence thereof, or (vi) the full-length complementary strand of (iv) or (v); (d) a malate dehydrogenase variant comprising a substitution, deletion, and/or insertion of one or more (e.g., two, several) amino acids of SEQ ID NO: 12 or the mature polypeptide sequence thereof; and (e) a fragment of a polypeptide of (a), (b), (c), or (d) that has malate dehydrogenase activity.

In one aspect, the malate dehydrogenase comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 12 or the mature polypeptide sequence thereof. In one aspect, the malate dehydrogenase comprises an amino acid sequence that differs by no more than ten amino acids, e.g., by no more than five amino acids, by no more than four amino acids, by no more than three amino acids, by no more than two amino acids, or by one amino acid from SEQ ID NO: 12 or the mature polypeptide sequence thereof.

In one aspect, the malate dehydrogenase comprises or consists of the amino acid sequence of SEQ ID NO: 12, the mature polypeptide sequence of SEQ ID NO: 12, an allelic variant thereof, or a fragment of the foregoing, having malate dehydrogenase activity. In another aspect, the malate dehydrogenase comprises or consists of the amino acid sequence of SEQ ID NO: 12. In another aspect, the malate dehydrogenase comprises or consists of the mature polypeptide sequence of SEQ ID NO: 12. In another aspect, the malate dehydrogenase comprises or consists of amino acids 1 to 330 of SEQ ID NO: 12.

In one aspect, the malate dehydrogenase is encoded by a polynucleotide that hybridizes under at least low stringency conditions, e.g., medium stringency conditions, medium-high stringency conditions, high stringency conditions, or very high stringency conditions with (i) SEQ ID NO: 11 or the mature polypeptide coding sequence thereof, (ii) the cDNA sequence of SEQ ID NO: 11 or the mature polypeptide coding sequence thereof, or (iii) the full-length complementary strand of (i) or (ii) (J. Sambrook, E. F. Fritsch, and T. Maniatis, 1989, supra).

In one aspect, the malate dehydrogenase is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 11 or the mature polypeptide coding sequence thereof, (v) the cDNA sequence of SEQ ID NO: 11 or the mature polypeptide coding sequence thereof; or (vi) the full-length complementary strand of (iv) or (v).

In one aspect, the malate dehydrogenase is encoded by SEQ ID NO: 11, or the mature polypeptide coding sequence thereof. In one aspect, the malate dehydrogenase is encoded by SEQ ID NO: 11. In one aspect, the malate dehydrogenase is encoded by the mature polypeptide coding sequence of SEQ ID NO: 11. In one aspect, the malate dehydrogenase is encoded by a subsequence of SEQ ID NO: 11, wherein the subsequence encodes a polypeptide having malate dehydrogenase activity. In one aspect, the subsequence contains at least 885 nucleotides, e.g., at least 930 nucleotides or at least 975 nucleotides of SEQ ID NO: 11.

In one aspect, the malate dehydrogenase is a variant comprising a substitution, deletion, and/or insertion of one or more (e.g., two, several) amino acids of SEQ ID NO: 12, or the mature polypeptide sequence thereof, as described supra. In one aspect, the malate dehydrogenase is a variant comprising a substitution, deletion, and/or insertion of one or more amino acids of SEQ ID NO: 12. In one aspect, the malate dehydrogenase is a variant comprising a substitution, deletion, and/or insertion of one or more amino acids of the mature polypeptide sequence of SEQ ID NO: 12. In some aspects, the total number of amino acid substitutions, deletions and/or insertions of the mature polypeptide sequence of SEQ ID NO: 12 or the mature polypeptide sequence thereof is not more than 10, e.g., not more than 1, 2, 3, 4, 5, 6, 7, 8 or 9.

In another aspect, the malate dehydrogenase is a fragment of SEQ ID NO: 12, or the mature polypeptide sequence thereof, wherein the fragment has malate dehydrogenase activity. In one aspect, the fragment contains at least 295 amino acid residues, e.g., at least 310 amino acid residues, or at least 325 amino acid residues of SEQ ID NO: 12.

The malate dehydrogenase may also be an allelic variant or artificial variant of a malate dehydrogenase.

The malate dehydrogenase can also include fused polypeptides or cleavable fusion polypeptides, as described supra.

Techniques used to isolate or clone a polynucleotide encoding a malate dehydrogenase are described supra.

The polynucleotide of SEQ ID NO: 11; or a subsequence thereof; as well as the amino acid sequence of SEQ ID NO: 12; or a fragment thereof; may be used to design nucleic acid probes to identify and clone DNA encoding malate dehydrogenases from strains of different genera or species, as described supra. Such probes are encompassed by the present invention. A genomic DNA or cDNA library prepared from such other organisms may be screened for DNA that hybridizes with the probes described above and encodes a malate dehydrogenase, as described supra.

In one aspect, the nucleic acid probe is SEQ ID NO: 11. In another aspect, the nucleic acid probe is the mature polypeptide coding sequence of SEQ ID NO: 11. In another aspect, the nucleic acid probe is a polynucleotide sequence that encodes SEQ ID NO: 12, the mature polypeptide sequence thereof, or a fragment of the foregoing.

For long probes of at least 100 nucleotides in length, very low to very high stringency and washing conditions are defined as described supra. For short probes of about 15 nucleotides to about 70 nucleotides in length, stringency and washing conditions are defined as described supra.

The malate dehydrogenase may be obtained from microorganisms of any genus. In one aspect, the malate dehydrogenase may be a bacterial, a yeast, or a filamentous fungal malate dehydrogenase obtained from the microorganisms described herein. In another aspect, the malate dehydrogenase is an *Aspergillus oryzae* malate dehydrogenase, e.g., the *Aspergillus oryzae* malate dehydrogenase of SEQ ID NO: 12.

Other malate dehydrogenases that can be used to practice the present invention include, but are not limited to, a *Aspergillus nidulans* malate dehydrogenase (AN6717.1; SIMS et al., 2004, *Mycol. Res.* 108: 853-857); *Aspergillus niger* malate dehydrogenase (An16g00120; Pel et al., 2007, *Nature Biotechnology* 25: 221-231); *Phytophthora infestans* malate dehydrogenase (PITG 13614.1; Calcagno et al., 2009, *Mycological Research* 113: 771-781); *Saccharomyces cerevisiae* malate dehydrogenase (YKL085W; McAlister-Henn and Thompson, 1987, *J Bacteria* 169: 5157-5166); *Talaromyces emersonii* malate dehydrogenase (AF439996, AF487682; Maloney et al., 2004, *Eur. J. Biochem.* 271: 3115-3126); and *Ustilago maydis* malate dehydrogenase (um00403, um11161; McCann and Snetselaar, 2008, *Fungal Genetics and Biology* 45: S77-S87), the *Aspergillus oryzae* malate dehydrogenase of SEQ ID NO: 20 (encoded by the polynucleotide sequence of SEQ ID NO: 19; see U.S. application Ser. No. 12/870,523, entitled "Methods for Improving Malic Acid Production in Filamentous Fungi" filed Aug. 27, 2010), or any aspect of the malate dehydrogenase described in the respective reference therein.

The invention embraces any aspect of sequence identity, hybridization, variants and fragments described herein as applied to the malate dehydrogenase polypeptide sequences and polynucleotide sequences described above. For example, in one aspect, the malate dehydrogenase is (a) a malate dehydrogenase having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 20, or the mature polypeptide sequence thereof; (b) a malate dehydrogenase encoded by a polynucleotide that hybridizes under low stringency conditions, e.g., medium stringency conditions, medium-high stringency conditions, high stringency conditions, or very high stringency conditions with (i) SEQ ID NO: 19 or the mature polypeptide coding sequence thereof, (ii) the cDNA sequence of SEQ ID NO: 19 or the mature polypeptide coding sequence thereof, or (iii) the full-length complementary strand of the (i) or (ii); (c) a malate dehydrogenase encoded by a polynucleotide having at least 60%, e.g., at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 19 or the mature polypeptide coding sequence thereof, (v) the cDNA sequence of SEQ ID NO: 19 or the mature polypeptide coding sequence thereof, or (vi) the full-length complementary strand of the (iv) or (v); (d) a malate dehydrogenase variant comprising a substitution, deletion, and/or insertion of one or more (e.g., two, several) amino acids of SEQ ID NO: 20 or the mature polypeptide sequence thereof; or (e) a fragment of a polypeptide of (a), (b), (c), or (d) that has malate dehydrogenase activity.

The malate dehydrogenase may also be identified and obtained from other sources including microorganisms isolated from nature (e.g., soil, composts, water, etc.) or DNA samples obtained directly from natural materials (e.g., soil, composts, water, etc,) as described supra.

Pyruvate Carboxylases and Polynucleotides Encoding Pyruvate Carboxylases

In some aspects of the recombinant host cells and methods of use thereof, the host cells have pyruvate carboxylase activity. In some aspects, the host cells comprise a heterologous polynucleotide encoding a pyruvate carboxylase. The pyruvate carboxylase can be any pyruvate carboxylase that is suitable for practicing the invention. In one aspect, the pyruvate carboxylase is an enzyme that is present in the cytosol of the host cell.

In one aspect of the recombinant host cells and methods described herein, the pyruvate carboxylase is (a) a pyruvate carboxylase having at least 60% sequence identity to SEQ ID NO: 16 or the mature polypeptide sequence thereof; (b) a pyruvate carboxylase encoded by a polynucleotide that hybridizes under low stringency conditions with (i) SEQ ID NO: 15 or the mature polypeptide coding sequence thereof, (ii) the cDNA sequence of SEQ ID NO: 15 or the mature polypeptide coding sequence thereof, or (iii) the full-length complementary strand of (i) or (ii); (c) a pyruvate carboxylase encoded by a polynucleotide having at least 60% sequence identity to (iv) SEQ ID NO: 15 or the mature polypeptide coding sequence thereof, (v) the cDNA sequence of SEQ ID NO: 15 or the mature polypeptide coding sequence thereof; or (vi) the full-length complementary strand of (iv) or (v); (d) a pyruvate carboxylase variant comprising a substitution, deletion, and/or insertion of one or more (e.g., two, several) amino acids of SEQ ID NO: 16 or the mature polypeptide sequence thereof; and (e) a fragment of a polypeptide of (a), (b), (c), or (d) that has pyruvate carboxylase activity.

In one aspect, the pyruvate carboxylase comprises or consists of an amino acid sequence having at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 16, or the mature polypeptide sequence thereof. In one aspect, the pyruvate carboxylase comprises an amino acid sequence that differs by no more than ten amino acids, e.g., by no more than five amino acids, by no more than four amino acids, by no more than three amino acids, by no more than two amino acids, or by one amino acid from SEQ ID NO: 16 or the mature polypeptide sequence thereof.

In one aspect, the pyruvate carboxylase comprises or consists of the amino acid sequence of SEQ ID NO: 16, the mature polypeptide sequence of SEQ ID NO: 16, an allelic variant thereof, or a fragment of the foregoing, having pyruvate carboxylase activity. In another aspect, the pyruvate carboxylase comprises or consists of the amino acid sequence of SEQ ID NO: 16. In another aspect, the pyruvate carboxylase comprises or consists of the mature polypeptide sequence of SEQ ID NO: 16. In another aspect, the pyruvate carboxylase comprises or consists of amino acids 1 to 1193 of SEQ ID NO: 16.

In one aspect, the pyruvate carboxylase is encoded by a polynucleotide that hybridizes under at least low stringency conditions, e.g., medium stringency conditions, medium-high stringency conditions, high stringency conditions, or very high stringency conditions with (i) SEQ ID NO: 15 or the mature polypeptide coding sequence thereof, (ii) the cDNA sequence of SEQ ID NO: 15 or the mature polypeptide coding sequence thereof, or (iii) the full-length complementary strand of (i) or (ii) (J. Sambrook, E. F. Fritsch, and T. Maniatis, 1989, supra).

In one aspect, the pyruvate carboxylase is encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to (iv) SEQ ID NO: 15 or the mature polypeptide coding sequence thereof, (v) the cDNA sequence of SEQ ID NO: 15 or the mature polypeptide coding sequence thereof; or (vi) the full-length complementary strand of (iv) or (v).

In one aspect, the pyruvate carboxylase is encoded by SEQ ID NO: 15 or the mature polypeptide coding sequence thereof. In one aspect, the pyruvate carboxylase is encoded by SEQ ID NO: 15. In one aspect, the pyruvate carboxylase is encoded by the mature polypeptide coding sequence of SEQ ID NO: 15. In one aspect, the pyruvate carboxylase is encoded by a subsequence of SEQ ID NO: 15, wherein the subsequence encodes a polypeptide having pyruvate carboxylase activity. In one aspect, the subsequence contains at least 3060 nucleotides, e.g., at least 3240 nucleotides or at least 3420 nucleotides of SEQ ID NO: 15.

In one aspect, the pyruvate carboxylase is a variant comprising a substitution, deletion, and/or insertion of one or more (e.g., two, several) amino acids of SEQ ID NO: 16, or the mature polypeptide sequence thereof, as described supra. In one aspect, the pyruvate carboxylase is a variant comprising a substitution, deletion, and/or insertion of one or more amino acids of SEQ ID NO: 16. In one aspect, the pyruvate carboxylase is a variant comprising a substitution, deletion, and/or insertion of one or more amino acids of the mature polypeptide sequence of SEQ ID NO: 16. In some aspects, the total number of amino acid substitutions, deletions and/or insertions of SEQ ID NO: 16 or the mature polypeptide sequence thereof is not more than 16, e.g., not more than 1, 2, 3, 4, 5, 6, 7, 8 or 9.

In another aspect, the pyruvate carboxylase is a fragment of SEQ ID NO: 16, or the mature polypeptide sequence thereof, wherein the fragment has pyruvate carboxylase activity. In one aspect, the fragment contains at least 1020 amino acid residues, e.g., at least 1080 amino acid residues, or at least 1140 amino acid residues of SEQ ID NO: 16.

The pyruvate carboxylase may also be an allelic variant or artificial variant of a pyruvate carboxylase.

The pyruvate carboxylase can also include fused polypeptides or cleavable fusion polypeptides, as described supra.

The pyruvate carboxylase can also be a variant of a mitochondrial pyruvate carboxylase, such that in vivo importation into the mitochondria is reduced thereby increasing the level of the pyruvate carboxylase variant in the cytosol.

Techniques used to isolate or clone a polynucleotide encoding a pyruvate carboxylase are described supra.

The polynucleotide of SEQ ID NO: 15 or a subsequence thereof, as well as the amino acid sequence of SEQ ID NO: 16 or a fragment thereof, may be used to design nucleic acid probes to identify and clone DNA encoding pyruvate carboxylases from strains of different genera or species, as described supra. Such probes are encompassed by the present invention. A genomic DNA or cDNA library prepared from such other organisms may be screened for DNA that hybridizes with the probes described above and encodes a pyruvate carboxylase, as described supra.

In one aspect, the nucleic acid probe is SEQ ID NO: 15. In another aspect, the nucleic acid probe is the mature polypeptide coding sequence of SEQ ID NO: 15. In another aspect, the nucleic acid probe is a polynucleotide sequence that encodes SEQ ID NO: 16, the mature polypeptide sequence thereof, or a fragment of the foregoing.

For long probes of at least 100 nucleotides in length, very low to very high stringency and washing conditions are defined as described supra. For short probes of about 15 nucleotides to about 70 nucleotides in length, stringency and washing conditions are defined as described supra.

The pyruvate carboxylase may be obtained from microorganisms of any genus. In one aspect, the pyruvate carboxylase may be a bacterial, a yeast, or a filamentous fungal pyruvate carboxylase obtained from the microorganisms described herein. In another aspect, the pyruvate carboxylase is an *Aspergillus oryzae* pyruvate carboxylase, e.g., the *Aspergillus oryzae* pyruvate carboxylase of SEQ ID NO: 16.

Other pyruvate carboxylases that can be used to practice the present invention include, but are not limited to, a *Aspergillus clavatus* NRRL 1 pyruvate carboxylase (XP__001271664; Direct Submission, Submitted (26 Oct. 2006), The Institute for Genomic Research, 9712 Medical Center Drive, Rockville, Md. 20850, USA); *Aspergillus fumigatus* Af293 pyruvate carboxylase (XP__752054; Nierman et al., 2005, *Nature* 438: 1151-1156); *Aspergillus nidulans* FGSC A4 pyruvate carboxylase (XP__662066; Galagan et al., 2005, *Nature* 438: 1105-1115); *Aspergillus niger* pyruvate carboxylase (An15g02820; Pel et al., 2007, *Nature Biotechnology* 25: 221-231; ASPNG 5061; Panneman et al., Submitted (JULY 1998) to the EMBL/GenBank/DDBJ databases); *Aspergillus terreus* pyruvate carboxylase (093918; Direct Submission, Submitted (OCTOBER 1998) The Institute for Genomic Research, 9712 Medical Center Drive, Rockville, Md. 20850, USA); *Magnaporthe grisea* 70-15 pyruvate carboxylase (XP__367852; Direct Submission, Submitted (26 Sep. 2005) Broad Institute of MIT and Harvard, 320 Charles Street, Cambridge, Mass. 02142, USA); *Neurospora crassa* OR74A pyruvate carboxylase (XP__965636; Galagan et al., 2003, *Nature* 422: 859-868); *Rhizopus oryzae* pyruvate carboxylase (RO3G__06931.1); *Saccharomyces cerevisiae* pyruvate carboxylase (NP__009777; Gaffeau et al., 1996, *Science* 274: 546-547); *Schizosaccharomyces pombe* pyruvate carboxylase (NP__595900; Direct Submission, Submitted (29 Jun. 2007) European *Schizosaccharomyces* genome sequencing project, Sanger Institute, The Wellcome Trust Genome Campus, Hinxton, Cambridge CB10 1SA); and *Ustilago maydis* pyruvate carboxylase (um01054; McCann and Snetselaar, 2008, *Fungal Genetics and Biology* 45: S77-S87). The invention embraces any aspect of sequence identity, hybridization, variants and fragments described herein as applied to the malate dehydrogenase polypeptide sequences and polynucleotide sequences described above.

The pyruvate carboxylase may also be identified and obtained from other sources including microorganisms isolated from nature (e.g., soil, composts, water, etc.) or DNA samples obtained directly from natural materials (e.g., soil, composts, water, etc,) as described supra.

Host Cells

The present invention also relates to recombinant host cells comprising a polynucleotide described herein operably linked to one or more (e.g., two, several) control sequences that direct the production of a polypeptides described herein. The invention also embraces recombinant host cells comprising one or more polynucleotide(s) described herein which may be operably linked to one or more control sequences that direct the expression of one or more of the described polypeptides for the recombinant production of a C4-dicarboxylic acid, as well as methods of using such host cells for the production of a C4-dicarboxylic acid. The host cell may comprise any one or combination of a plurality of the polynucleotides described. For example, in one aspect, the recombinant host cell comprises a heterologous polynucleotide encoding a C4-dicarboxylic acid transporter; and optionally comprises a heterologous polynucleotide encoding a heterologous polynucleotide encoding a malate dehydrogenase, and/or a heterologous polynucleotide encoding pyruvate decarboxylase; wherein the host cell produces (or is capable of producing) a greater amount of a C4-dicarboxylic acid compared to the host cell without the heterologous polynucleotide encoding the C4-dicarboxylic acid transporter when cultivated under the same conditions.

In one aspect, the recombinant host cell comprises:

(1) a heterologous polynucleotide encoding a C4-dicarboxylic acid transporter, such as a C4-dicarboxylic acid transporter selected from: (a) a C4-dicarboxylic acid transporter having at least 60% sequence identity to SEQ ID NO: 2, 4, or 6, or the mature polypeptide sequence thereof; (b) a C4-dicarboxylic acid transporter encoded by a polynucleotide that hybridizes under low stringency conditions with SEQ ID NO: 1, 3, or 5, the mature polypeptide coding sequence thereof, or the full-length complementary strand of the foregoing; (c) a C4-dicarboxylic acid transporter encoded by a polynucleotide having at least 60% sequence identity to SEQ ID NO: 1, 3, or 5, the mature polypeptide coding sequence thereof, or the full-length complementary strand of the foregoing; (d) a C4-dicarboxylic acid transporter variant comprising a substitution, deletion, and/or insertion of one or more (e.g., two, several) amino acids of SEQ ID NO: 2, 4, or 6, or the mature polypeptide sequence thereof; and (e) a fragment of a polypeptide of (a), (b), (c), or (d) that has C4-dicarboxylic acid transporter activity;

(2) an optional heterologous second polynucleotide encoding a malate dehydrogenase, such as a malate dehydrogenase selected from: (a) a malate dehydrogenase having at least 60% sequence identity to SEQ ID NO: 12 or the mature polypeptide sequence thereof; (b) a malate dehydrogenase encoded by a polynucleotide that hybridizes under low stringency conditions with (i) SEQ ID NO: 11 or the mature polypeptide coding sequence thereof, (ii) the cDNA sequence of SEQ ID NO: 11 or the mature polypeptide coding sequence thereof, or (iii) the full-length complementary strand of (i) or (ii); (c) a malate dehydrogenase encoded by a polynucleotide having at least 60% sequence identity to (iv) SEQ ID NO: 11 or the mature polypeptide coding sequence thereof, (v) the cDNA sequence of SEQ ID NO: 11 or the mature polypeptide coding sequence thereof; or (vi) the full-length complementary strand of (iv) or (v); (d) a malate dehydrogenase variant comprising a substitution, deletion, and/or insertion of one or more (e.g., two, several) amino acids of SEQ ID NO: 12 or the mature polypeptide sequence thereof; and (e) a fragment of a polypeptide of (a), (b), (c), or (d) that has malate dehydrogenase activity; and (3) an optional heterologous third polynucleotide encoding a pyruvate carboxylase, such as a pyruvate carboxylase selected from: (a) a pyruvate carboxylase having at least 60% sequence identity to SEQ ID NO: 16 or the mature polypeptide sequence thereof; (b) a pyruvate carboxylase encoded by a polynucleotide that hybridizes under low stringency conditions with (i) SEQ ID NO: 15 or the mature polypeptide coding sequence thereof, (ii) the cDNA sequence of SEQ ID NO: 15 or the mature polypeptide coding sequence thereof, or (iii) the full-length complementary strand of (i) or (ii); (c) a pyruvate carboxylase encoded by a polynucleotide having at least 60% sequence identity to (iv) SEQ ID NO: 15 or the mature polypeptide coding sequence thereof, (v) the cDNA sequence of SEQ ID NO: 15 or the mature polypeptide coding sequence thereof; or (vi) the full-length complementary strand of (iv) or (v); (d) a pyruvate carboxylase variant comprising a substitution, deletion, and/or insertion of one or more (e.g., two, several) amino acids of SEQ ID NO: 16 or the mature polypeptide sequence thereof; and (e) a fragment of a polypeptide of (a), (b), (c), or (d) that has pyruvate carboxylase activity;

wherein the host cell produces (or is capable of producing) a greater amount of a C4-dicarboxylic acid (e.g., malic acid) compared to the host cell without the one or more polynucleotide(s) (e.g., without the heterologous polynucleotide encoding a C4-dicarboxylic acid transporter), when cultivated under the same conditions.

In one aspect, the host cell comprises a heterologous polynucleotide encoding a C4-dicarboxylic acid transporter described herein (e.g., SEQ ID NO: 1, 3, 5, or any described aspect thereof) and a heterologous polynucleotide encoding a malate dehydrogenase. In the present invention, the malate dehydrogenase can be any malate dehydrogenase that is suitable for practicing the present invention, as described supra. In another aspect, the host cell comprises a heterologous polynucleotide encoding a C4-dicarboxylic acid transporter described herein (e.g., SEQ ID NO: 1, 3, 5, or any described aspect thereof) and a heterologous polynucleotide encoding a pyruvate carboxylase. In the present invention, the pyruvate carboxylase can be any pyruvate carboxylase that is suitable for practicing the present invention, as described supra. In particular, the pyruvate carboxylase is preferably an enzyme that is present in the cytosol of the host cell. In one aspect, the host cell comprises a heterologous polynucleotide encoding a C4-dicarboxylic acid transporter described herein (e.g., SEQ ID NO: 1, 3, 5, or any described aspect thereof), a second heterologous polynucleotide encoding a malate dehydrogenase, and a third heterologous polynucleotide encoding a pyruvate carboxylase.

A construct or vector (or multiple constructs or vectors) comprising the one or more (e.g., two, several) polynucleotide(s) is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. The aspects described below apply to the host cells, per se, as well as methods using the host cells.

The host cell may be any cell capable of the recombinant production of a polypeptide of the present invention, e.g., a prokaryote or a eukaryote, and/or any cell (e.g., any filamentous fungal cell) capable of the recombinant production of a C4-dicarboxylic acid (e.g., malic acid).

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Tricho-*

*derma koningii, Trichoderma longibrachiatum, Trichoderma reesei,* or *Trichoderma viride* cell.

In one aspect, the host cell is an *Aspergillus* host cell. In another aspect, the host cell is *Aspergillus oryzae*.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In some aspects, the host cell comprises one or more (e.g., two, several) polynucleotide(s) described herein, wherein the host cell secretes (and/or is capable of secreting) an increased level of C4-dicarboxylic acid compared to the host cell without the one or more polynucleotide(s) when cultivated under the same conditions. In some aspects, the host cell secretes and/or is capable of secreting an increased level of C4-dicarboxylic acid (e.g., malic acid) of at least 5%, e.g., at least 10%, at least 15%, at least 20%, at least 25%, at least 50%, at least 100%, at least 150%, at least 200%, at least 300%, or at 500% compared to the host cell without the one or more polynucleotide(s) (e.g., without the heterologous polynucleotide encoding a C4-dicarboxylic acid transporter), when cultivated under the same conditions.

In any of the aspects of the recombinant host cells and methods described herein, the C4-dicarboxylic acid may be malic acid, succinic acid, oxaloacetic acid, malonic acid, or fumaric acid, or combinations thereof. In some aspects, the C4-dicarboxylic acid is malic acid, succinic acid, or fumaric acid, or combinations thereof. In some aspects, the C4-dicarboxylic acid is malic acid or fumaric acid, or a combination of malic acid and fumaric acid. In some aspects, the C4-dicarboxylic acid is malic acid.

In any of these aspects, the host cell produces (and/or is capable of producing) a C4-dicarboxylic acid at a yield of at least than 10%, e.g., at least than 20%, at least than 30%, at least than 40%, at least than 50%, at least than 60%, at least than 70%, at least than 80%, or at least than 90%, of theoretical.

In any of these aspects, the recombinant host has an C4-dicarboxylic acid volumetric productivity (e.g., malic acid volumetric productivity) greater than about 0.1 g/L per hour, e.g., greater than about 0.2 g/L per hour, 0.5 g/L per hour, 0.6 g/L per hour, 0.7 g/L per hour, 0.8 g/L per hour, 0.9 g/L per hour, 1.0 g/L per hour, 1.1 g/L per hour, 1.2 g/L per hour, 1.3 g/L per hour, 1.5 g/L per hour, 1.75 g/L per hour, 2.0 g/L per hour, 2.25 g/L per hour, 2.5 g/L per hour, or 3.0 g/L per hour; or between about 0.1 g/L per hour and about 2.0 g/L per hour, e.g., between about 0.3 g/L per hour and about 1.7 g/L per hour, about 0.5 g/L per hour and about 1.5 g/L per hour, about 0.7 g/L per hour and about 1.3 g/L per hour, about 0.8 g/L per hour and about 1.2 g/L per hour, or about 0.9 g/L per hour and about 1.1 g/L per hour.

The recombinant host cells may be cultivated in a nutrient medium suitable for production of the C4-dicarboxylic acid transporter, malate dehydrogenase, or pyruvate carboxylase using methods well known in the art, as described below.

The C4-dicarboxylic acid transporter, malate dehydrogenase, and pyruvate carboxylase, and activities thereof, can be detected using methods known in the art. These detection methods may include use of specific antibodies, formation of an enzyme product, or disappearance of an enzyme substrate. See, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999); and Hanai et al., *Appl. Environ. Microbiol.* 73:7814-7818 (2007)).

Methods of Production

The present invention also relates to methods of producing a polypeptide described herein (e.g., a polypeptide comprising or consisting of SEQ ID NO: 2, 4, 6, or any described aspect thereof), comprising: (a) cultivating a cell, which in its wild-type form produces the polypeptide, under conditions conducive for production of the polypeptide; and (b) recovering the polypeptide. In one aspect, the cell is of the genus *Aspergillus*. In another aspect, the cell is *Aspergillus aculeatus*. In a another aspect, the cell is *E. coli* NRRL B-50400, *E. coli* NRRL B-50388, or *E. coli* NRRL B-50401.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the C4-dicarboxylic acid transporter using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The C4-dicarboxylic acid transporter may be detected using methods known in the art that are specific for the polypeptides, as described supra. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (e.g., two, several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the $^{35}$S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, cotransformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Removal or Reduction of C4-Dicarboxylic Acid Transporter Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by introduction, substitution, or removal of one or more (e.g., two, several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In a particularly preferred aspect, the polynucleotide is disrupted with a selectable marker such as those described herein.

The present invention also relates to methods of inhibiting the expression of a polypeptide having C4-dicarboxylic acid transporter activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of SEQ ID NO: 1, 3, or 5, or the mature polypeptide coding sequence thereof for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for the expression of native and heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

Methods of C4-Dicarboxylic Acid Production

The present invention is also directed to methods of using the polypeptides having C4-dicarboxylic acid transporter activity, or polynucleotides encoding the polypeptides having C4-dicarboxylic acid transporter activity. The C4-dicarboxylic acid transporters described herein or polynucleotides encoding the same may be used in a host cell (e.g., a filamentous fungal host cell) to aid in the production, such as increasing production, of a C4-dicarboxylic acid (e.g., malic acid). For these methods, any of the polynucleotides or polypeptides of the present invention described herein (e.g., SEQ ID NO: 1, 2, 3, 4, 5, and/or 6, or any described aspect thereof) may be used, as exemplified in the aspects set forth below.

In one aspect, the present invention relates to methods of producing a C4-dicarboxylic acid (e.g., malic acid), comprising: (1) cultivating a host cell (e.g., filamentous fungal host cell) comprising a heterologous polynucleotide encoding a C4-dicarboxylic acid transporter described herein (e.g., SEQ ID NO: 1, 3, 5, or any described aspect thereof), wherein the host cell secretes increased levels of the C4-dicarboxylic acid compared to the host cell without the heterologous polynucleotide encoding a C4-dicarboxylic acid transporter; and (2) recovering the malic acid.

In another aspect, the present invention relates to methods for increasing C4-dicarboxylic acid production (e.g., malic acid production) relative to a parent host cell, comprising: (1) transforming into a host cell (e.g., a filamentous fungal host cell) a heterologous polynucleotide encoding a C4-dicarboxylic acid transporter described herein (e.g., SEQ ID NO: 1, 3, 5, or any described aspect thereof), wherein the host cell secretes an increased level of C4-dicarboxylic acid compared to the filamentous fungal host cell without the heterologous polynucleotide; (2) cultivating the transformed organism in a medium; and (3) recovering the C4-dicarboxylic acid.

In some of these aspects of the methods, the C4-dicarboxylic acid is malic acid, succinic acid, oxaloacetic acid, malonic acid, or fumaric acid, or combinations thereof. In some aspects, the C4-dicarboxylic acid is malic acid, succinic acid, or fumaric acid, or combinations thereof. In some aspects, the C4-dicarboxylic acid is malic acid or fumaric acid, or a combination of malic acid and fumaric acid. In some aspects, the C4-dicarboxylic acid is malic acid.

As described supra, the C4-dicarboxylic acid transporter may be any C4-dicarboxylic acid transporters described herein, e.g., a C4-dicarboxylic acid transporter selected from: (a) a polypeptide having at least 60% sequence identity to SEQ ID NO: 2, 4, or 6, or the mature polypeptide sequence thereof; (b) a polypeptide encoded by a polynucleotide that hybridizes under low stringency conditions with SEQ ID NO: 1, 3, or 5, the mature polypeptide coding sequence thereof, or a full-length complementary strand of the foregoing; (c) a polypeptide encoded by a polynucleotide having at least 65% sequence identity to SEQ ID NO: 1, 3, or 5, or the mature polypeptide coding sequence thereof; (d) a variant comprising a substitution, deletion, and/or insertion of one or more (e.g., two, several) amino acids of SEQ ID NO: 2, 4, or 6, the mature polypeptide thereof; and (e) a fragment of the polypeptide of (a), (b), (c), or (d).

For example, in one aspect, the present invention relates to a method of producing a C4-dicarboxylic acid (e.g., malic acid), comprising:

(1) cultivating a host cell (e.g., filamentous fungal host cell) comprising a heterologous polynucleotide encoding a C4-dicarboxylic acid transporter, wherein the C4-dicarboxylic acid transporter is selected from: (a) a polypeptide having at least 60% sequence identity to SEQ ID NO: 2, or the mature polypeptide thereof; (b) a polypeptide encoded by a polynucleotide that hybridizes under low stringency conditions with SEQ ID NO: 1, the mature polypeptide coding sequence thereof, or the full-length complementary strand of the foregoing; (c) a polypeptide encoded by a polynucleotide having at least 65% sequence identity to SEQ ID NO: 1, or the mature polypeptide coding sequence thereof; (d) a variant comprising a substitution, deletion, and/or insertion of one or more (e.g., two, several) amino acids of SEQ ID NO: 2 or the mature polypeptide sequence thereof; and (e) a fragment of the polypeptide of (a), (b), (c), or (d); wherein the host cell secretes increased levels of the C4-dicarboxylic acid compared to the host cell without the heterologous polynucleotide encoding a C4-dicarboxylic acid transporter; and (2) recovering the malic acid.

In another exemplary aspect, the present invention relates to a method of producing a C4-dicarboxylic acid (e.g., malic acid), comprising:

(1) cultivating a host cell (e.g., filamentous fungal host cell) comprising a heterologous polynucleotide encoding a C4-dicarboxylic acid transporter, wherein the C4-dicarboxylic acid transporter is selected from: (a) a polypeptide having at least 60% sequence identity to SEQ ID NO: 4 or the mature polypeptide thereof; (b) a polypeptide encoded by a polynucleotide that hybridizes under low stringency conditions with SEQ ID NO: 3 the mature polypeptide coding sequence thereof, or the full-length complementary strand of the foregoing; (c) a polypeptide encoded by a polynucleotide having at least 65% sequence identity to SEQ ID NO: 3 or the mature polypeptide coding sequence thereof; (d) a variant comprising a substitution, deletion, and/or insertion of one or more (e.g., two, several) amino acids of SEQ ID NO: 4 or the mature polypeptide sequence thereof; and (e) a fragment of the polypeptide of (a), (b), (c), or (d); wherein the host cell secretes increased levels of the C4-dicarboxylic acid compared to the host cell without the heterologous polynucleotide encoding a C4-dicarboxylic acid transporter; and (2) recovering the malic acid.

In another exemplary aspect, the present invention relates to a method of producing a C4-dicarboxylic acid (e.g., malic acid), comprising:

(1) cultivating a host cell (e.g., filamentous fungal host cell) comprising a heterologous polynucleotide encoding a C4-dicarboxylic acid transporter, wherein the C4-dicarboxylic acid transporter is selected from: (a) a polypeptide having at least 60% sequence identity to SEQ ID NO: 6 or the mature polypeptide thereof; (b) a polypeptide encoded by a polynucleotide that hybridizes under low stringency conditions with SEQ ID NO: 5, the mature polypeptide coding sequence thereof, or the full-length complementary strand of the foregoing; (c) a polypeptide encoded by a polynucleotide having at least 65% sequence identity to SEQ ID NO: 5 or the mature polypeptide coding sequence thereof; (d) a variant comprising a substitution, deletion, and/or insertion of one or more (e.g., two, several) amino acids of SEQ ID NO: 6 or the mature polypeptide thereof; and (e) a fragment of the polypeptide of (a), (b), (c), or (d); wherein the host cell secretes increased levels of the C4-dicarboxylic acid compared to the host cell without the heterologous polynucleotide encoding a C4-dicarboxylic acid transporter; and (2) recovering the malic acid.

Additional variations and embodiments of the polypeptides having C4-dicarboxylic acid transporter activity contemplated in the methods above are described throughout the present application.

In one aspect of the methods, the C4-dicarboxylic acid (e.g., malic acid) is produced or secreted at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 300 g/L, about 150 g/L and about 250 g/L, about 175 g/L and about 225 g/L, or about 190 g/L and about 210 g/L.

In any of the aspects of the methods, the level of the produced or secreted C4-dicarboxylic acid (e.g., malic acid) in the host cell is increased by at least 25%, e.g., at least 50%, at least 100%, at least 150%, at least 200%, at least 300%, or at 500% compared to the host cell without the polynucleotide encoding the heterologous polynucleotide when cultivated under the same conditions.

In any of these aspects of the methods, the heterologous polynucleotide may be operably linked to a promoter foreign to the polynucleotide.

In any of these aspects of the methods, the host cell may further comprise a heterologous second polynucleotide encoding a malate dehydrogenase (e.g., the mature polypeptide coding sequence of SEQ ID NO: 11, or any described aspect thereof) and/or a heterologous third polynucleotide encoding a pyruvate carboxylase (e.g., the mature polypeptide coding sequence of SEQ ID NO: 15, or any described aspect thereof), as described supra. In some aspects, the heterologous second and/or third polynucleotide is operably linked to a promoter foreign to the polynucleotide. Examples of malate dehydrogenases and pyruvate carboxylases that may be used with these methods can be found, for example, in PCT Application No. PCT/US10/47002, entitled "Methods for Improving Malic Acid Production in Filamentous Fungi" filed Aug. 27, 2010, the content of which is hereby incorporated by reference in its entirety, particularly with respect to the polynucleotides encoding malate dehydrogenase and pyruvate carboxylase polypeptides described therein.

In any of these aspects of the methods, the host cell may be any host cell described above, e.g., a filamentous fungal host cell, such as a host cell selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes*, and *Trichoderma*. For example, the host cell may be an *Aspergillus* host cell, such as an *Aspergillus oryzae* host cell.

In the methods of the present invention, the recombinant host cell is cultivated in a nutrient medium suitable for production of the C4-dicarboxylic acid transporter, using methods well known in the art, as described supra.

The recombinant C4-dicarboxylic acid can be optionally recovered from the fermentation medium using any procedure known in the art (see, for example, WO 1998/022611 and U.S. Pat. No. 7,601,865) including, but not limited to, chromatography (e.g., size exclusion chromatography, adsorption chromatography, ion exchange chromatography), electrophoretic procedures, differential solubility, osmosis, distillation, extraction (e.g., liquid-liquid extraction), pervaporation, extractive filtration, membrane filtration, membrane separation, reverse, or ultrafiltration. In one example, the C4-dicarboxylic acid is recovered from other material in the fermentation medium by filtration.

In some aspects of the methods, the recombinant C4-dicarboxylic acid before and/or after being optionally purified is substantially pure. With respect to the methods of producing a C4-dicarboxylic acid (or a specific C4-dicarboxylic acid thereof, such as malic acid), "substantially pure" intends a recovered preparation of the C4-dicarboxylic acid that contains no more than 15% impurity, wherein impurity intends compounds other than C4-dicarboxylic acids. In one variation, a preparation of substantially pure C4-dicarboxylic acid is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of C4-dicarboxylic acids for the methods of production and host cells described herein can be performed using methods known in the art. For example, the final C4-dicarboxylic acid product (e.g., malic acid), and other organic compounds, can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of C4-dicarboxylic acid in the fermentation broth can also be tested with the culture supernatant. Byproducts and residual sugar in the fermentation medium (e.g., glucose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

Signal Peptide

The present invention also relates to an isolated polynucleotide encoding a signal peptide. In one aspect, the signal peptide comprises or consists of amino acids 1 to 61 or 1 to 68 of SEQ ID NO: 2. In some aspects, the isolated polynucleotide encoding the signal peptide is nucleotides 1 to 183, or 1 to 204 of SEQ ID NO: 1. In another aspect, the signal peptide comprises or consists of amino acids 1 to 17 of SEQ ID NO: 4. In some aspects, the isolated polynucleotide encoding the signal peptide is nucleotides 1 to 51 of SEQ ID NO: 3. In another aspect, the signal peptide comprises or consists of amino acids 1 to 68 of SEQ ID NO: 6. In some aspects, the isolated polynucleotide encoding the signal peptide is nucleotides 1 to 204 of SEQ ID NO: 5.

The polynucleotides may further comprise a gene encoding a protein, which is operably linked to the signal peptide and/or propeptide. The protein is preferably foreign to the signal peptide and/or propeptide.

The present invention also relates to nucleic acid constructs, expression vectors and recombinant host cells comprising such polynucleotides.

The present invention also relates to methods of producing a protein, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Chemicals used as buffers and substrates were commercial products of at least reagent grade.

Fungal Strains

*Aspergillus aculeatus* was used as source of the C4-dicarboxylic acid transport protein genes c4t737, c4t521, and mat737. *Aspergillus oryzae* NRRL 3488 (or ATCC 56747) was used as a source of a pyruvate carboxylase gene, a malate dehydrogenase gene, and for production of the C4-dicarboxylic acids.

Media

YEG medium was composed of 20 g glucose, 5 g yeast extract, and deionized water to 1 liter.

COVE plates were composed of 1 M sucrose, 2% COVE salt solution, 10 mM acetamide, 15 mM CsCl, and 25 g/l Agar Noble.

COVE salt solution was composed of 26 g KCl, 26 g $MgSO_4.7H_2O$, 76 g $KH_2PO_4$, 50 ml of COVE trace elements solution, and deionized water to 1 liter.

COVE trace elements solution was composed of 0.04 g $Na_2B_4O_7.10H_2O$, 0.04 g $CuSO_4.5H_2O$, 1.2 g $FeSO_4.7H_2O$, 0.7 g $MnSO_4.H_2O$, 0.8 g $Na_2MoO_2.2H_2O$, 10 g $ZnSO_4.7H_2O$ and deionized water to 1 liter.

Seed medium was composed of 40 g glucose, 6 g Bacto-peptone, 750 mg $KH_2PO_4$, 750 mg $K_2HPO_4$, 100 mg $MgSO_4.7H_2O$, 100 mg $CaCl_2.H_2O$, 5 mg $FeSO_4.7H_2O$, 5 mg NaCl, and deionized water to 1 liter.

Seed medium B was composed of 30 g glucose, 3 g Bacto-peptone, 560 mg $KH_2PO_4$, 560 mg $K_2HPO_4$, 925 mg $NaH_2PO_4.H_2O$, 820 mg $Na_2HPO_4$, 75 mg $MgSO_4.7H_2O$, 75 mg $CaCl_2.H_2O$, 0.75 ml of 1000X Micronutrient Solution, and deionized water to 1 liter.

Acid production medium C was composed of 100 g glucose, 80 g $CaCO_3$, 6 g Bacto Peptone, 150 mg $KH_2PO_4$, 150 mg $K_2HPO_4$, 100 mg $MgSO_4.7H_2O$, 100 mg $CaCl_2.H_2O$, 1 ml 1000X Micronutrient Solution, and deionized water to 1 liter.

Fermentor batch medium was composed of 120 g glucose, 120 g $CaCO_3$, 9 g Bacto-peptone, 150 mg $KH_2PO_4$, 150 mg $K_2HPO_4$, 100 mg $MgSO.7H_2O$, 100 mg $CaCl_2-2H_2O$, 5 mg $FeSO_4.7H_2O$, 5 mg NaCl, 5 mL Pluronic L61, and deionized water to 1 liter.

1000X Micronutrient Solution was composed of 5 g NaCl, 5 g $FeSO_4 7H_2O$, 1 g citric acid, and deionized water to 1 liter.

PDA plates were composed of 39 g/l potato dextrose agar.

2XYT+amp plates were composed of 16 g tryptone, 10 g yeast extract, 5 g NaCl, 100 mg ampicillin, 15 g Bacto agar, and deionized water to 1 liter.

Example 1

Cloning of an *Aspergillus aculeatus* C4-Dicarboxylic Acid Transporter Gene and Construction of Expression Vector pSaMF35

Genomic DNA from *Aspergillus* aculeatus was isolated by inoculating 100 ml of YEG medium in a shake flask with $2 \times 10^6$ spores and incubating the flask at 34° C. overnight with shaking at 160 rpm. The mycelia were harvested by filtration using a MIRACLOTH®(Calbiochem, San Diego, Calif., USA) lined funnel and approximately 2 g of mycelia were recovered and frozen in liquid nitrogen. The frozen mycelia were disrupted by quickly smashing with a hammer while wrapped inside the MIRACLOTH®. The disrupted mycelia were then transferred to a 50 ml polypropylene conical centrifuge tube containing 10 ml of 1× lysis buffer (100 mM EDTA, 10 mM Tris pH 8.0, 1% Triton® X-100, 0.5 M Guanidine-HCl, 200 mM NaCl) and 3 µl of RNase A (QIAGEN Inc., Valencia, Calif., USA, 100 mg/ml). The tube was mixed by gentle vortexing, then incubated at room temperature for 5 minutes after which was added 150 µl Proteinase K (QIAGEN Inc., Valencia, Calif., USA; 20 mg/ml). The tube was mixed by inversion and incubated at 50° C. for 1 hour. The tube was then centrifuged at 7240×g for 20 minutes. The supernatant was then added to a pre-equilibrated QIAGEN-tip 100 (QIAGEN Inc., Valencia, Calif., USA) and the remaining DNA extraction steps were performed according to the manufacturer's instructions. The DNA was resuspended in 100 µl TE buffer (10 mM Tris Base, 1 mM EDTA, pH 8.0).

The 1194 bp C4-dicarboxylic acid transporter gene c4t737 was amplified from *Aspergillus aculeatus* genomic DNA using primers 069698 and 069699 shown below.

```
Primer 069698:
                                        (SEQ ID NO: 7)
5'-GTGATAGAACATCGTCCATAATGCTCGGGCAACACT-3'

Primer 069699:
                                        (SEQ ID NO: 8)
5'-GTGTCAGTCACCTCTAGTTATTACTCCGATACATCCTCGT-3'
```

The PCR reaction was composed of 5 μl 10× reaction buffer (Stratagene, La Jolla, Calif., USA), 1 μl *A. aculeatus* genomic DNA template (105 ng/μl), 1 μl primer 069698 (100 ng/μl), 1 μl primer 069699 (100 ng/μl), 1 μl dNTP mixture (10 mM), 40.5 μl deionized water, and 0.5 μl Herculase® Hot-Start DNA polymerase (Stratagene, La Jolla, Calif., USA). The amplification reaction was incubated in an EPPENDORF® MASTERCYCLER® (Eppendorf Scientific Inc. Westbury, N.Y., USA) programmed for 1 cycle at 95° C. for 2 minutes; 10 cycles each at 95° C. for 10 seconds, 60° C. for 30 seconds, and 72° C. for 1.5 minutes; and 20 cycles each at 95° C. for 10 seconds, 60° C. for 30 seconds, and 72° C. for 1.5 minutes plus 10 seconds per cycle. The PCR product was then purified using a MinElute® PCR Purification Kit (QIAGEN Inc., Valencia, Calif., USA).

Figure 2:
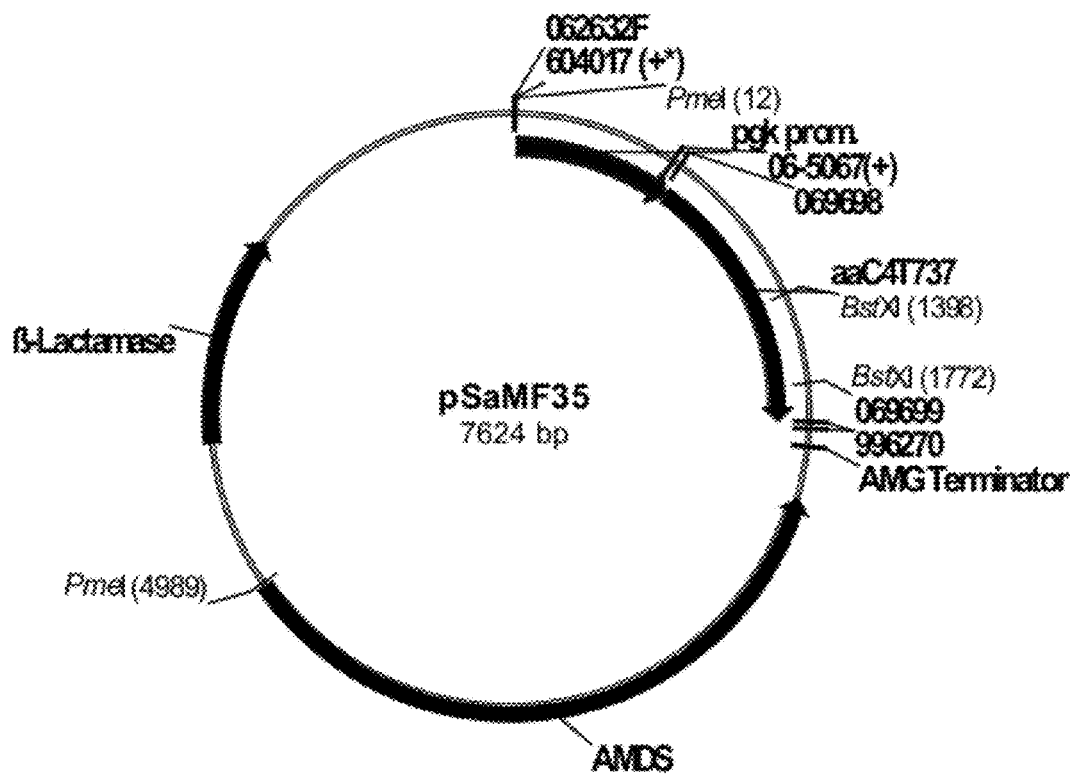
FIG. 2 shows a restriction map of pSaMF35.

Plasmid pShTh60 (FIG. 1; see also PCT Application No. PCT/US10/47002, filed Aug. 27, 2010) was digested with Sex AI and Pac I, separated by 0.8% agarose gel electrophoresis in TBE buffer (10.8 g/L Tris Base, 5.5 g/L Boric acid, 2 mM EDTA, pH 8.0) and purified using a QIAQUICK® Gel Extraction Kit (QIAGEN Inc., Valencia, Calif., USA). The purified PCR product above was then inserted into the digested pShTh60 fragment using an In-Fusion™ Advantage reaction kit (Clontech, Mountain View, Calif., USA) composed of 2 μl 5× buffer (Clontech, Mountain View, Calif., USA), 2.4 μl purified PCR product (33 ng/μl), 1.5 μl digested and gel-purified pShTh60 (132 ng/μl), 1 μl In-Fusion™ enzyme and 3.1 μl deionized water. The reaction was incubated at 37° C. for 15 minutes, 50° C. for 15 minutes, placed on ice for 5 minutes and diluted with 40 μl TE buffer (10 mM Tris Base, 1 mM EDTA, pH 8.0) resulting in pSaMF35 (FIG. 2).

A 2.5 μl aliquot of the ligation reaction above containing pSaMF35 was transformed into ONE SHOT® TOP10 chemically competent *E. coli* cells (Invitrogen, San Diego, Calif., USA) according to the manufacturer's instructions. Transformants were plated onto 2XYT+amp plates and incubated at 37° C. overnight. The resulting transformants were picked and subjected to DNA sequencing to confirm that the c4t737 gene was integrated into the vector.

Figure 3:
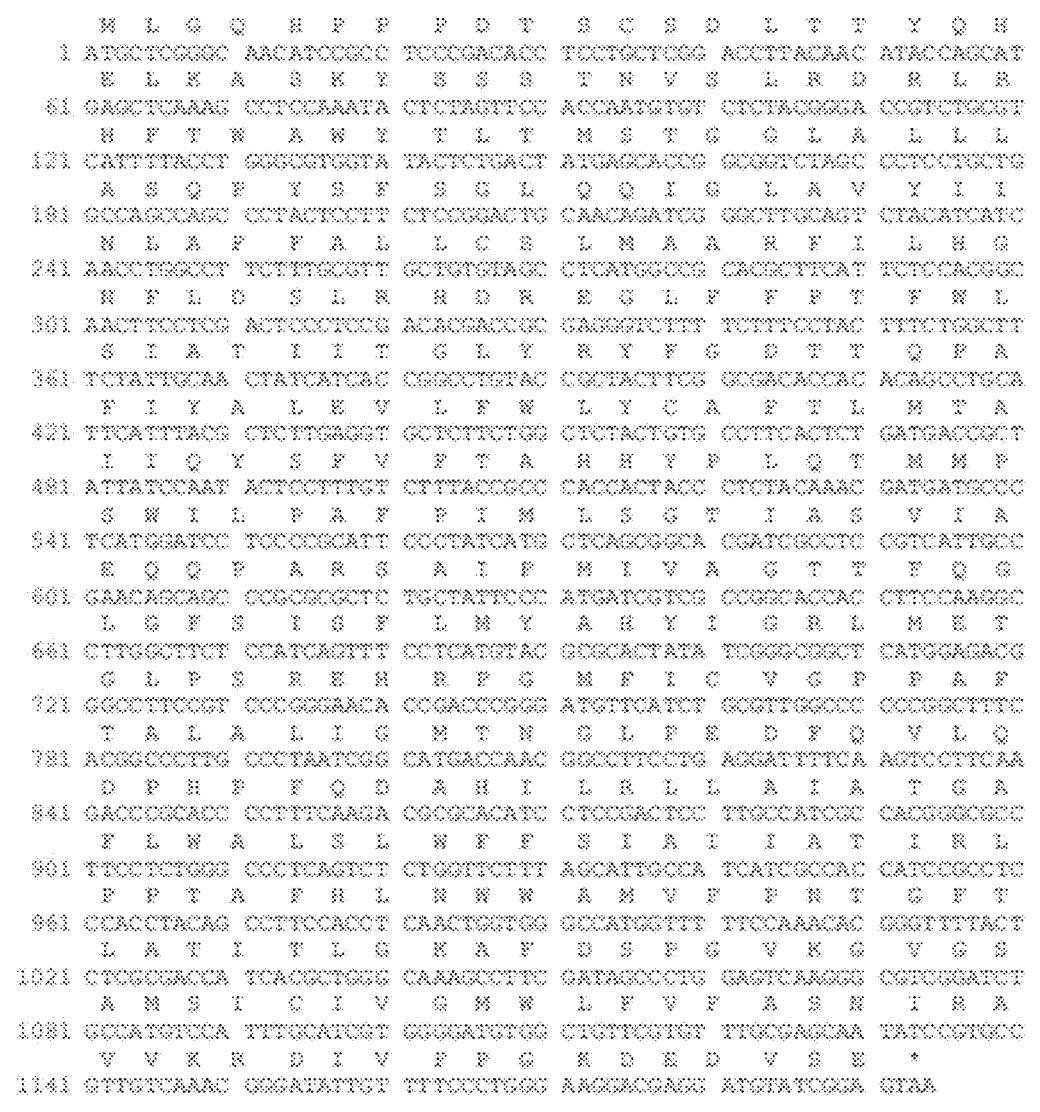

The nucleotide sequence (SEQ ID NO: 1) and deduced amino acid sequence (SEQ ID NO: 2) of the *Aspergillus aculeatus* c4t737 gene are shown in FIG. 3. The coding sequence is 1194 bp including the stop codon. The encoded predicted protein is 397 amino acids, with a predicted molecular mass of 44.3 kDa and an isoelectric pH of 6.93. The gene contains no introns. Using the SignalP program (Nielsen et al., 1997, *Protein Engineering* 10:1-6), a signal peptide of 61 residues was predicted. Based on this program, the predicted mature protein contains 336 amino acids with a predicted molecular mass of 37.3 kDa and an isoelectric pH of 6.52. Using the InterProScan program (The European Bioinformatics Institute), a signal peptide of 68 residues was predicted. Based on this program, the predicted mature protein contains 329 amino acids with a predicted molecular mass of 36.5 kDa and an isoelectric pH of 6.52.

Example 2

Transformation of an Expression Vector Fragment of pSaMF35 into *Aspergillus oryzae* NRRL 3488 (SaMF35)

Protoplast preparation and transformation of *Aspergillus oryzae* NRRL 3488 were performed by inoculating approximately $2 \times 10^7$ spores into 100 ml YEG medium and incubating the flask at 27° C. for 16-18 hours at 140 rpm. Mycelia were collected by pouring the culture through a sterile funnel lined with MIRACLOTH® (Calbiochem, San Diego, Calif., USA) and rinsing with 50 ml of 0.7 M KCl. The washed mycelia were resuspended in a 125 ml flask containing 20 ml of protoplasting solution composed of 5 mg GLUCANEX™ (Novozymes A/S, Bagsværd, Denmark) and 0.5 mg chitinase (Sigma Chemical Co., St. Louis, Mo., USA) per ml of 0.7 M KCl (filter sterilized) and incubated at 34° C. for 30 minutes with mixing at 80 rpm. The protoplasting solution was poured through a sterile funnel lined with MIRACLOTH® and rinsed with 50 ml of STC buffer (1 M sorbitol-10 mM Tris-HCl pH 6.5-10 mM $CaCl_2$). The flow-through was collected in two 50 ml polypropylene tubes. The tubes were centrifuged at 1300×g for 10 minutes at room temperature. The supernatant was discarded and the protoplast pellet was resuspended in 20 ml of STC buffer. The protoplasts were washed by two rounds of resuspending the pellet in 20 ml of STC buffer and centrifugation at 1300×g for 10 minutes at room temperature. The final pellet was resuspended in 2 ml of STC buffer. The protoplasts were counted by removing a 10 μl sample and counting them in a hemacytometer (VWR, West Chester, Pa., USA). The volume was adjusted with STC buffer to obtain a protoplast concentration of $2 \times 10^7$ per ml.

Plasmid pSaMF35 was prepared for transformation by restriction digestion with Pme I. The 4977 bp expression cassette was separated from the digested vector by 0.8% agarose gel electrophoresis in TBE buffer and purified using a QIAQUICK® Gel Extraction Kit. Two transformation reactions were prepared. For each reaction, a 100 μl solution of protoplast preparation was transferred to a 12 ml polypropylene tube, to which was added 5 μg of linearized pSaMF35, 250 μl PEG solution (60% w/v polyethylene glycol (PEG), 10 mM Tris 6.5, 10 mM CaCl) followed by gentle mixing and incubation at 37° C. for 30 minutes. Each transformation was diluted with 9 ml of STC buffer, followed by plating three separate 3 ml aliquots onto COVE plates. Each plate was then incubated at 34° C. for 7-10 days. Twenty SaMF35 transformants were transferred to individual COVE plates and incubated at 34° C. for 5 days. Spore stocks were prepared by collecting the spores in 0.1% TWEEN® 80. Cultures were stored by preparing a glycerol stock of each (800 μl spore stock, 200 μl 0.1% TWEEN® 80) and frozen at −80° C.

Example 3

Production of Malic Acid in Shake Flask Cultures of *Aspergillus oryzae* Transformants Containing an Expression Vector Fragment of pSaMF35 (SaMF35)

Spores from each pSaMF35 transformant described in Example 2 and *Aspergillus oryzae* NRRL 3488 as a control were plated onto individual PDA plates and allowed to sporulate at 34° C. for 5 to 7 days. Spores were collected in 0.1% TWEEN® 80 and counted using a hemacytometer. Seed cultures were prepared in 250 ml flasks containing 100 ml of seed medium B and inoculated with 300 μl of spore suspension. Seed cultures were grown for approximately 17 hours at 30° C. with shaking at 200 rpm. Acid production cultures were prepared in 250 ml unbaffled flasks containing 50 ml of acid production medium C and 3 ml of the 17 hour seed cultures. Cultures were incubated at 30° C. with shaking at 200 rpm for 2-10 days.

Quantitation of malic acid for the shake flask culture transformants was performed by Reverse Phase High Pressure Liquid Chromatography (RP-HPLC) using an 1200 Series Binary LC System and 1200 Series Diode Array Detector (DAD) (Agilent Technologies, Santa Clara, Calif. USA). Reverse phase separation was performed using an Aqua 5μ C18 125 Å 205×4.6 mm ID column and AQ C18 4×3.0 mm Security Guard Cartridge (Phenomenex, Inc., Torrance, Calif., USA). The mobile phase consisted of 10% methanol (HPLC grade) and 90% 145 mM phosphate pH 1.5 buffer.

Whole culture samples were removed and diluted 1:10 in HPLC Running Buffer composed of 850 ml of 64 mM phosphate buffer and 150 ml of methanol pH 1.65. The samples were then filtered through a 25 mm 0.45 micron polyethersulfone membrane (Whatman, Florham Park, N.J., USA) and 1.5 ml of the filtrates was placed into a HPLC vial for acid analysis. The remaining amount of the shake flask cultures were filtered through 3 layers of cheese cloth and rinsed three times with 10 volumes of double distilled sterile water to remove insoluble $CaCO_3$. Cell pellets were harvested from the cheese cloth, placed into a 15 ml culture tube and stored at −20° C.

RP-HPLC was performed using an injection volume of 10 μl at a flow rate of 0.7 ml/minute (isocratic) with a column temperature of 25° C. and run time of 11 minutes. Detection was set at 210 nm, 8 nm bandwidth, with the reference at 360 nm, 40 nm bandwidth. The void time was determined to be 3.8 minutes. The quantitative capabilities of the reverse phase method were determined for malic acid by performing replicate injections of serially diluted malic acid standards with concentrations ranging from 49.2-3.93 mM. The relative standard deviation for (RSD) for replicate injections was ≦5%. Malic acid shows $R^2 \geq 0.9999$.

*Aspergillus oryzae* transformant containing pSaMF35 showed an improvement in malic acid production of greater than 2-fold over the *Aspergillus oryzae* NRRL 3488 control strains after 3 days of shake flask growth.

Example 3B

Fermentation of *Aspergillus oryzae* Transformants Containing an Expression Vector Fragment of pSaMF35 (SaMF35)

*Aspergillus oryzae* pSaMF35 transformants described in Example 2 and control transformant *Aspergillus oryzae* ShTh1040 (see PCT Application No. PCT/US10/47002, filed Aug. 27, 2010) were prepared and fermented as described in Example 7 below.

Quantitation of malic acid in the fermentations was performed as described above. The relative malic acid titer of *Aspergillus oryzae* pSaMF35 transformants were comparable to the *Aspergillus oryzae* ShTh1040 transformants, indicating that the *Aspergillus oryzae* pSaMF35 transformants outperform the *Aspergillus oryzae* NRRL 3488 control (which lack the overexpressed C4-dicarboxylic acid transporter gene) based on ShTh1040 and NRRL 3488 comparisons previously described.

Example 4

Cloning of an *Aspergillus aculeatus* C4-Dicarboxylic Acid Transporter Gene and Construction of Expression Vector pSaMF36

The 1257 bp C4-dicarboxylic acid transporter gene c4t521 was amplified from isolated *Aspergillus aculeatus* genomic DNA (Example 1) using primers 069700 and 069701 shown below.

Primer 069700:
(SEQ ID NO: 9)
5'-TGTGATAGAACATCGTCCATAATGCACGACCACAGC-3'

Primer 069701:
(SEQ ID NO: 10)
5'-GTGTCAGTCACCTCTAGTTATCATTCGAACAACTCGGACA-3'

The PCR reaction was composed of 10 μl 5× reaction buffer, 1 μl *A. aculeatus* genomic DNA template (105 ng/μl), 1 μl primer 069700 (100 ng/μl), 1 μl primer 069701 (100 ng/μl), 1 μl dNTP mixture (10 mM), 35.5 μl deionized water, and 0.5 μl Phusion™ Hot Start High-Fidelity DNA polymerase (Finnzymes, Inc, Massachusetts, USA). The amplification reaction was incubated in an EPPENDORF® MASTERCYCLER® programmed for 1 cycle at 98° C. for 30 seconds; 30 cycles each at 98° C. for 10 seconds, 60° C. for 30 seconds, 72° C. for 1 minute; and one cycle at 72° C. for 10 minutes. The PCR product was digested with Dpn I for 1 hour to degrade any plasmid DNA template.

Figure 4:
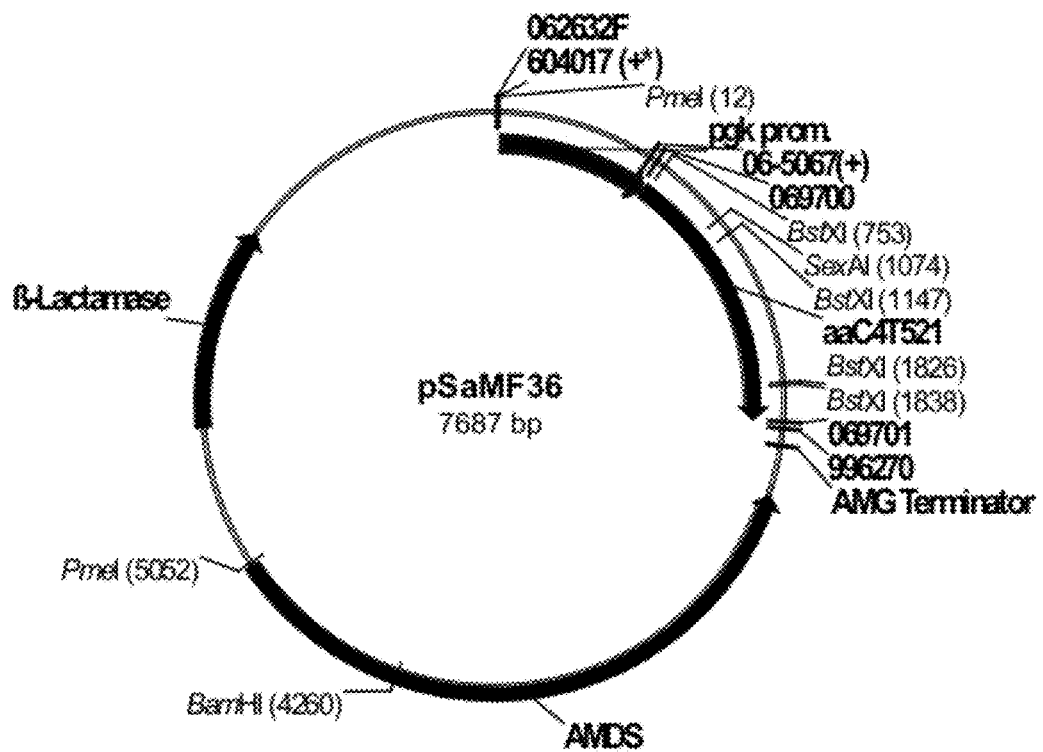
FIG. 4 shows a restriction map of pSaMF36.

Plasmid pShTh60 (FIG. 1) was digested with Sex AI and Pac I, separated by 0.8% agarose gel electrophoresis in TBE buffer, and purified using a QIAQUICK® Gel Extraction Kit. The purified PCR product above was then inserted into the digested pShTh60 fragment using an In-Fusion™ Advantage reaction kit composed of 2 μl 5× buffer, 3 μl purified PCR product (26 ng/μl), 1.5 μl gel-purified Sex AI and Pac I digested and gel-purified pShTh60 (132 ng/μl), 1 μl In-Fusion™ enzyme and 2.5 μl deionized water. The reaction was incubated at 37° C. for 15 minutes, 50° C. for 15 minutes, placed on ice for 5 minutes and diluted with 40 μl TE buffer resulting in pSaMF36 (FIG. 4).

A 2.5 μl aliquot of the ligation reaction above was transformed into ONE SHOT® TOP10 chemically competent *E. coli* cells according to the manufacturer's instructions. Transformants were plated onto 2XYT+amp plates and incubated at 37° C. overnight. The resulting transformants were picked and subjected to DNA sequencing to confirm that the mat521 gene was successfully integrated into the vector.

Figure 5:
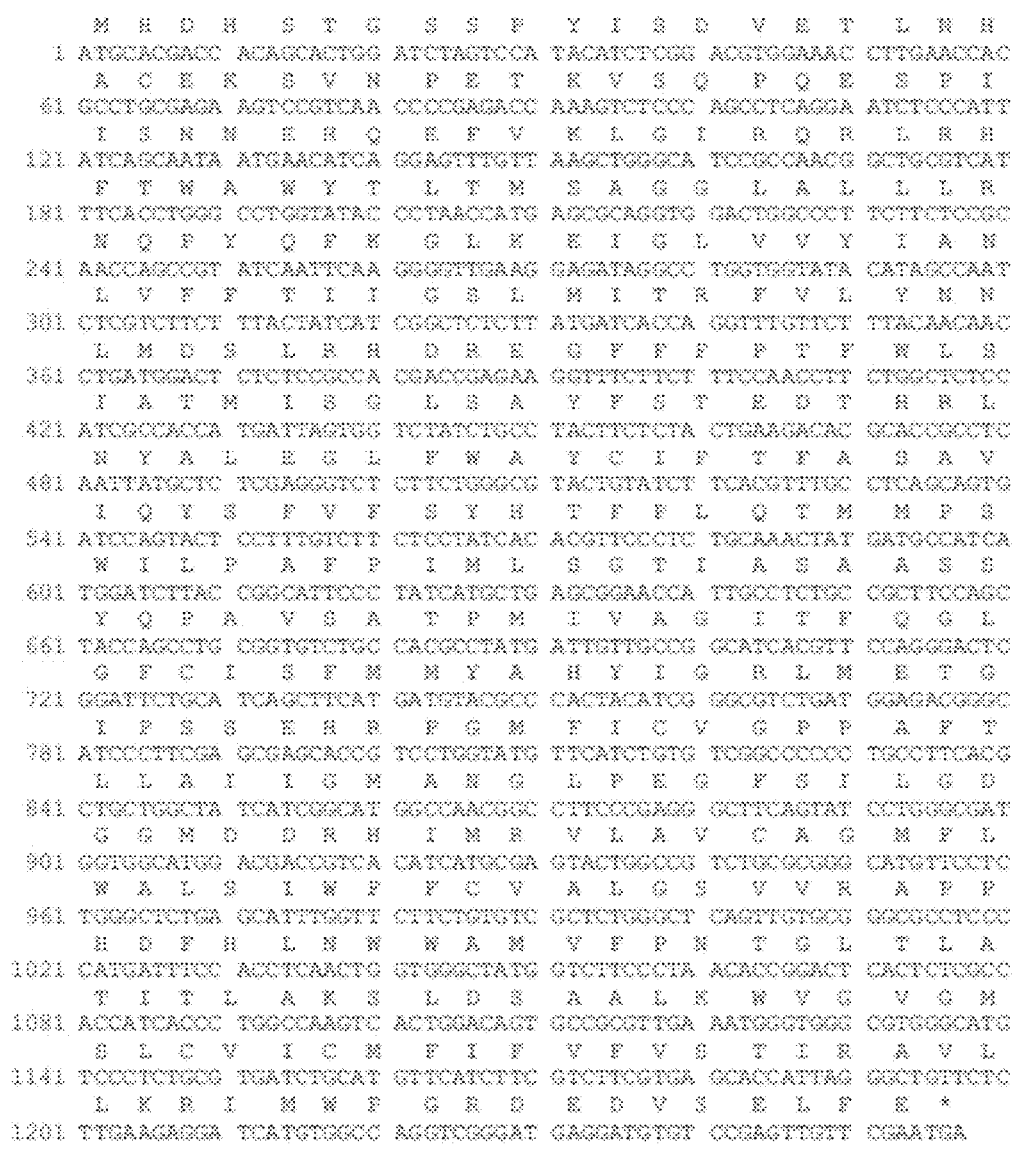

The nucleotide sequence (SEQ ID NO: 3) and deduced amino acid sequence (SEQ ID NO: 4) of the *Aspergillus aculeatus* c4t521 gene are shown in FIG. 5. The coding sequence is 1257 bp including the stop codon. The encoded predicted protein is 418 amino acids, with a predicted molecular mass of 46.8 kDa and an isoelectric pH of 6.36. The gene contains no introns. Using the SignalP program (Nielsen et al., 1997, *Protein Engineering* 10:1-6), a signal peptide of 17 residues was predicted. Based on this program, the predicted mature protein contains 401 amino acids with a predicted molecular mass of 44.9 kDa and an isoelectric pH of 6.89.

Example 5

Transformation of an Expression Vector Fragment of pSaMF36 into *Aspergillus oryzae* NRRL 3488 (SaMF36)

Protoplast preparation and transformation of *Aspergillus oryzae* NRRL 3488 were performed as described in Example 2.

Plasmid pSaMF36 was prepared for transformation by restriction digestion with Pme I. The 5040 bp expression cassette was separated from the digested vector by 0.8% agarose gel electrophoresis in TBE buffer and purified using a QIAQUICK® Gel Extraction Kit. Two transformation reactions were prepared. For each transformation reaction, 100 µl of protoplast preparation was transferred to a 12 ml polypropylene tube, to which was added 5 µg of linearized pSaMF36 and 250 µl PEG solution (60% w/v polyethylene glycol (PEG), 10 mM Tris 6.5, 10 mM CaCl) followed by gentle mixing and incubation at 37° C. for 30 minutes. Each transformation was diluted with 9 ml of STC buffer, followed by plating three separate 3 ml aliquots onto COVE plates. Each plate was then incubated at 34° C. for 7-10 days. Twenty SaMF36 transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 6

Production of Malic Acid in Shake Flask Cultures of *Aspergillus oryzae* Transformants Containing an Expression Vector Fragment of pSaMF36 (SaMF36)

Spores from each pSaMF36 transformant described in Example 5 and *Aspergillus oryzae* NRRL 3488 as a control were prepared as described in Example 3. Quantitation of malic acid for the shake flask culture transformants was performed as described in Example 3.

Table 1 shows the relative increase in malic acid titer of transformants *Aspergillus oryzae* SaMF36-3 and *Aspergillus oryzae* SaMF36-4 compared to malic acid production of *Aspergillus oryzae* NRRL 3488 as a control after 3 days of shake flask growth. *Aspergillus oryzae* SaMF36-3 and *Aspergillus oryzae* SaMF36-4 produced an increase in malic acid titer of 2.1-fold and 2.3-fold, respectively, compared to *Aspergillus oryzae* NRRL 3488.

TABLE 1

| Strain | Relative titer of malic acid | % CV |
|---|---|---|
| NRRL 3488 | 1 | 0.7% |
| SaMF36-3 | 2.1 | 4.8% |
| SaMF36-4 | 2.3 | 0.2% |

Example 7

Fermentation of *Aspergillus oryzae* Transformants Containing an Expression Vector Fragment of pSaMF36 (SaMF36)

*Aspergillus oryzae* pSaMF36 transformants described in Example 5 and control transformant *Aspergillus oryzae* ShTh1040 (see PCT Application No. PCT/US10/47002, filed Aug. 27, 2010) were grown for approximately 7 days at 34° C. on PDA plates. A 5-6 ml volume of sterile 50 mM sodium phosphate buffer (pH 6.8) containing 0.2% TWEEN® 80 was added to each plate and spores were suspended by scraping with an inoculating loop. Each suspension was transferred by pipette to a 50 ml conical tube. For each tube, 25 ml of sterile sodium phosphate buffer (50 mM, pH 6.8) was added to a 500 ml unbaffled flask containing 75 ml of seed medium, which was then inoculated with 2 ml of spore suspension. The flasks were then incubated at 34° C. and 180 rpm for about 24 hours. The seed flasks were combined to supply the 144 ml inoculum required per tank.

Three-liter fermentors containing 1.8 liters of fermentor batch medium were individually inoculated by introducing 144 ml (8%) of the seed culture broth from the combined seed flasks of either an *Aspergillus oryzae* pSaMF36 transformant or an *Aspergillus oryzae* ShTh1040 transformant. For this example only, the glucose concentration in the fermentor batch medium was reduced to 60 g/L and the feed start was delayed by one day. The fermentors were equilibrated at 34° C.±0.1° C. and stirred at 500 rpm. Inlet air flow was maintained at 1 v/v/m. A 20% glucose stream was administered at a rate of approximately 7.3 g/hr beginning at about 43 hours of fermentation. Sterile $CaCO_3$ (about 100 g) was added around day 5 or 6 to keep the fermentation pH in the range of 6 to 7. Samples were withdrawn daily and analyzed for malic acid production as described in Example 3. Fermentation was completed after 7 or 8 days.

Quantitation of malic acid in the fermentations was performed as described in Example 3. The relative malic acid titer of *Aspergillus oryzae* pSaMF36 transformants was comparable to *Aspergillus oryzae* ShTh1040, indicating that the *Aspergillus oryzae* pSaMF36 transformants outperform the *Aspergillus oryzae* NRRL 3488 (which lack the overexpressed C4-dicarboxylic acid transporter gene) in malic acid production based on ShTh1040 and NRRL 3488 comparisons previously described.

Example 8

Cloning of an *Aspergillus oryzae* Malate Dehydrogenase Gene and Construction of Expression Vector pSaMF21

Figure 6:
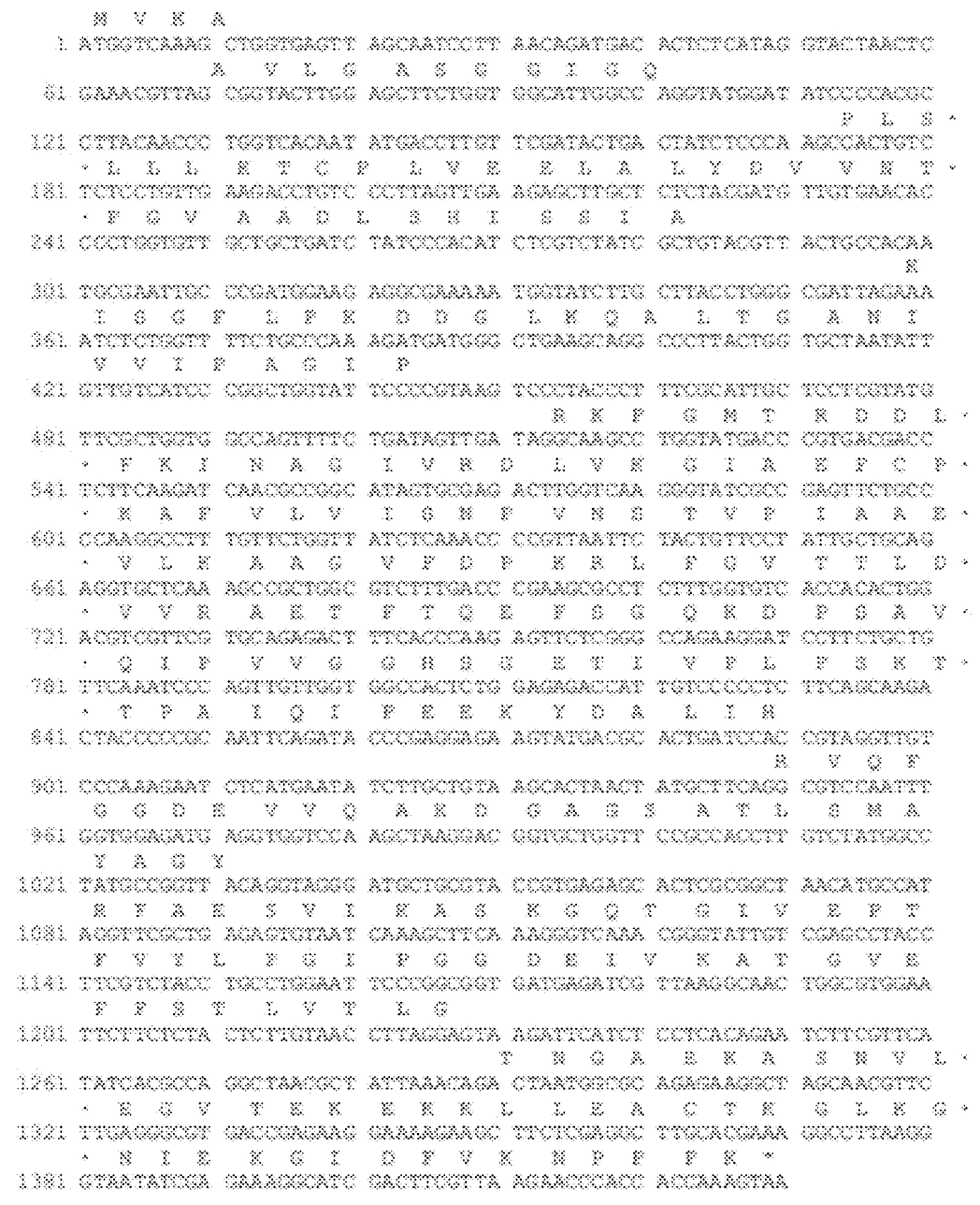

Plasmid pSaMF21 was constructed to contain the NAD-dependent malate dehydrogenase (mdh3) gene sequence (DOGAN: A0090701000013), a 1430 bp fragment from *Aspergillus oryzae* as described in PCT Application No. PCT/US10/47002, filed Aug. 27, 2010. The nucleotide sequence (SEQ ID NO: 11) and deduced amino acid sequence (SEQ ID NO: 12) of the *Aspergillus oryzae* NRRL 3488 malate dehydrogenase mdh3 gene are shown in FIG. 6. The genomic coding sequence of 1430 bp (including stop codon) encodes a polypeptide of 330 amino acids with a predicted mass of 35 kDa. The coding sequence is interrupted by 7 introns of 57 bp (14-70 bp), 70 bp (103-172 bp), 74 bp (284-357 bp), 68 bp (446-513 bp), 58 bp (892-949 bp), 48 bp (1035-1082 bp), and 62 bp (1228-1289 bp). The G+C content of the coding region of the mdh3 gene is 50.3%.

Briefly, the plasmid was constructed by linearizing pShTh60 (FIG. 1) by restriction digestion with Sex AI and Pac I. The digested vector was separated by 0.8% agarose gel electrophoresis in TBE buffer and purified using a QIAQUICK® Gel Extraction Kit. The mdh3 gene was amplified from pShTh71 (PCT Application No. PCT/US10/47002, filed Aug. 27, 2010) using primers 067522 and 067525.

Primer 067522:
(SEQ ID NO: 13)
5'-AGAACATCGTCCATAATGGTCAAAGCTGGTGAGTTA-3'

Primer 067525:
(SEQ ID NO: 14)
5'-GTGTCAGTCACCTCTAGTTATTACTTTGGTGGTGGGTTCT-3'

Figure 7:
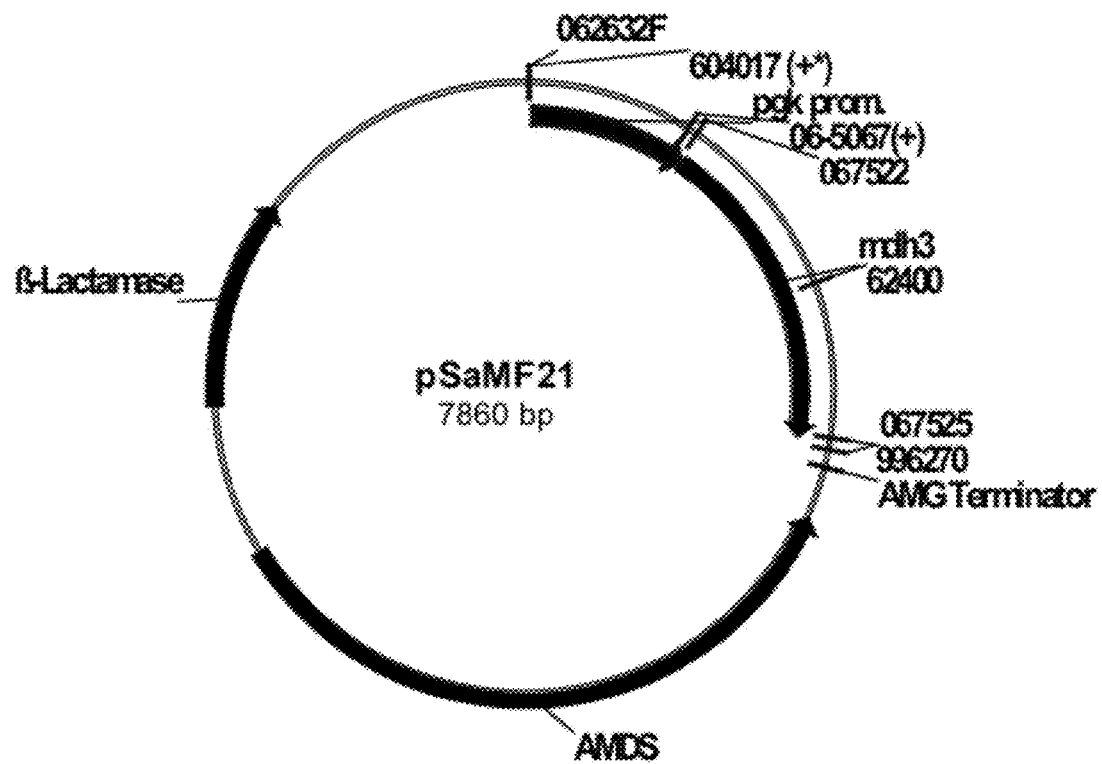
FIG. 7 shows a restriction map of pSaMF21.

The PCR reaction was composed of 5 µl 10× reaction buffer, 1 µl pShTh71 template (87 ng/µl), 1 µl primer 067522 (100 ng/µl), 1 µl primer 067525 (100 ng/µl), 1 µl dNTP mixture (10 mM), 45.5 µl deionized water, and 0.5 µl Herculase® HotStart DNA polymerase (Stratagene, La Jolla, Calif., USA). The amplification reaction was incubated in an EPPENDORF® MASTERCYCLER® programmed for 1 cycle at 95° C. for 2 minutes; 10 cycles each at 95° C. for 10 seconds, 58° C. for 30 seconds, and 72° C. for 1.5 minutes; 20 cycles each at 95° C. for 10 seconds, 50° C. for 30 seconds, and 72° C. for 1.5 minutes plus 10 seconds per cycle. The PCR reaction was subjected to a restriction digest with Dpn I for 1 hour to degrade any plasmid DNA template. The PCR product was then purified using the MinElute® PCR Purification Kit (QIAGEN Inc., Valencia, Calif., USA). The purified PCR product was inserted into the vector using an In-Fusion™ Advantage reaction composed of 2 µl 5× buffer, 0.5 µl purified PCR product (110 ng/µl), 1.7 µl gel-purified Sex AI and Pac I restriction digested pShTh60 (FIG. 1; 78 ng/µl), 1 µl In-Fusion™ enzyme and 4.8 µl deionized water. The reaction was incubated at 37° C. for 15 minutes followed by 50° C. for 15 minutes after which it was placed on ice for 5 minutes and diluted with 40 µl TE buffer resulting in pSaMF21 (FIG. 7). A 2 µl aliquot of the ligation reaction was transformed into ONE SHOT® TOP10 chemically competent *E. coli* cells (Invitrogen, San Diego, Calif., USA) according to the manufacturer's instructions. Transformants were plated onto 2XYT+amp plates and incubated at 37° C. overnight. The resulting transformants were picked and subjected to DNA sequencing to confirm that the mdh3 gene was successfully integrated into the vector.

Example 9

Cloning of an *Aspergillus oryzae* Pyruvate Carboxylase Gene and Construction of Expression Vector pRyan1

Figure 8A:
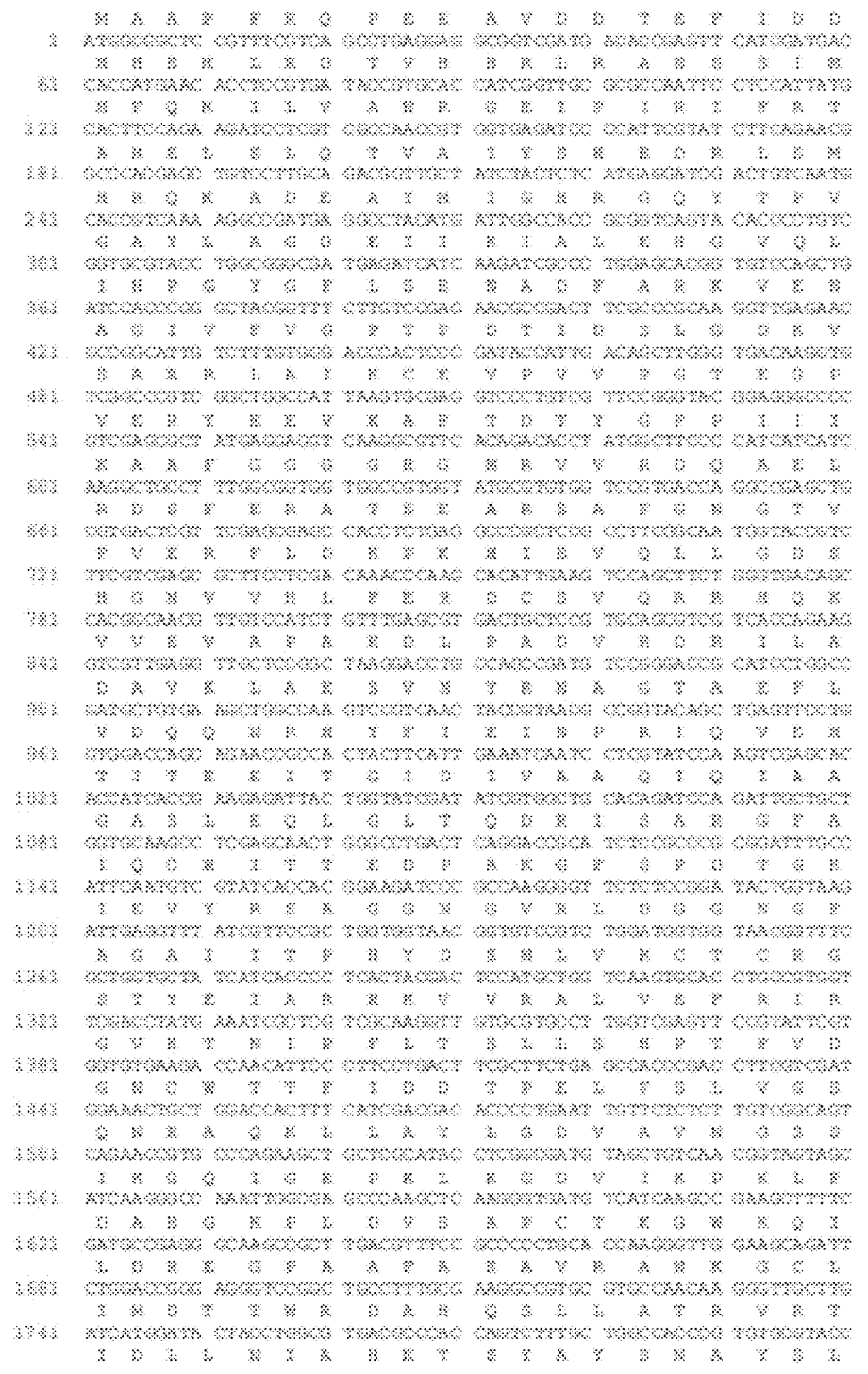
Figure 8B:
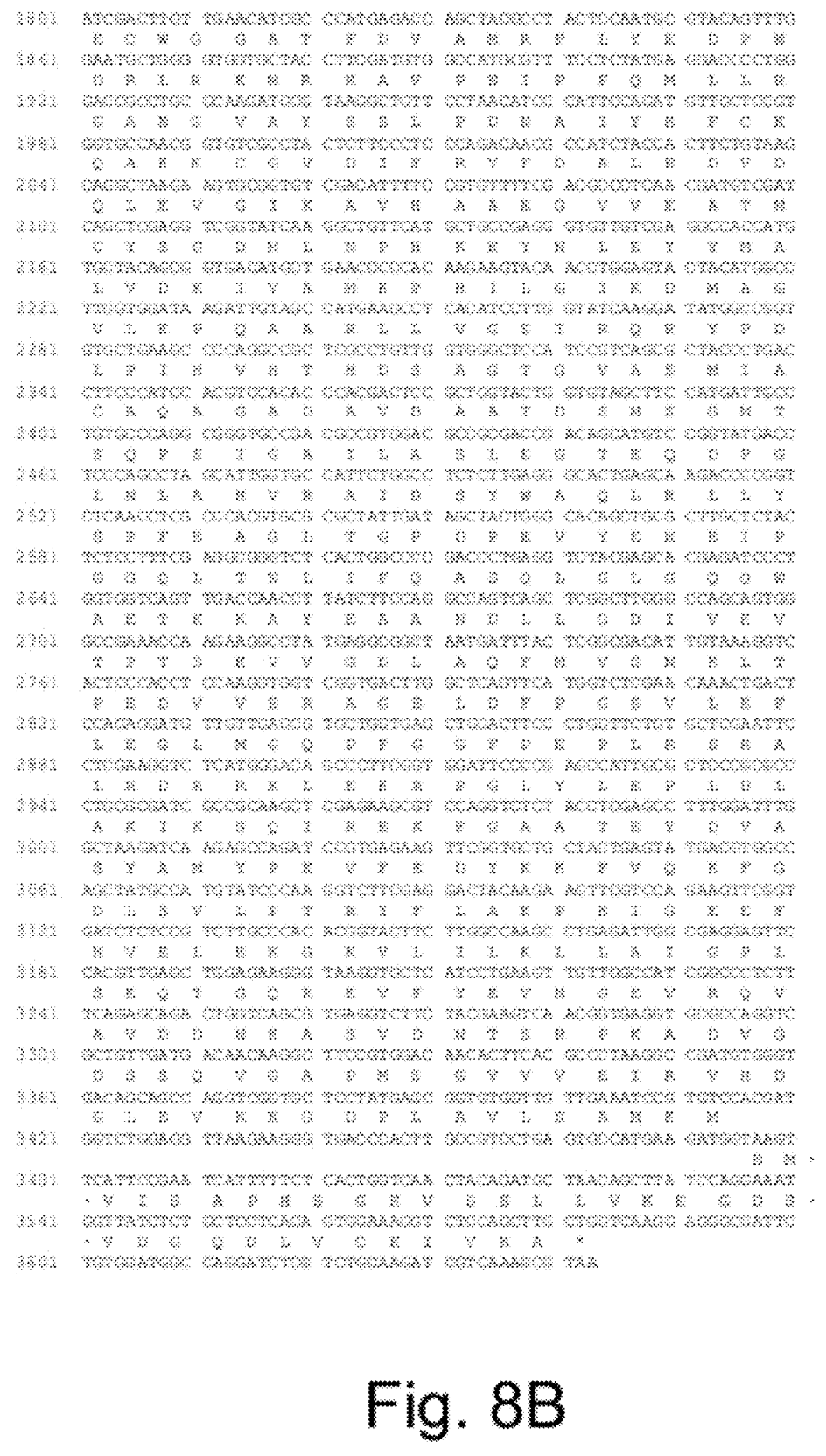

Plasmid pRyan1 was constructed to contain the pyruvate carboxylase (pyc) gene sequence (DOGAN: A0090023000801), a 3646 bp fragment from *Aspergillus oryzae* (including two stop codons) as described in PCT Application No. PCT/US10/47002, filed Aug. 27, 2010. The nucleotide sequence (SEQ ID NO: 15) and deduced amino acid sequence (SEQ ID NO: 16) of the *Aspergillus oryzae* pyruvate carboxylase genes are shown in FIGS. 8A and 8B. Both the *Aspergillus oryzae* NRRL 3488 and ATCC 56747 pyruvate carboxylase genes have the same nucleotide sequence. The genomic coding sequence of 3643 bp (including one stop codon) encodes a polypeptide of 1193 amino acids with a predicted mass of 131 kDa. The coding sequence is interrupted by 1 intron of 61 bp (3475-3535 bp). The G+C content of the coding region of the gene is 57.1%.

Briefly, the plasmid was constructed by linearizing pShTh60 (FIG. 1) by restriction digestion with Sex AI and Pac I. The digested vector was separated by 0.8% agarose gel electrophoresis in TBE buffer and purified using a QIAQUICK® Gel Extraction Kit. The pyc gene was amplified from *Aspergillus oryzae* NRRL 3488 genomic DNA using primers 066549 and 067388 shown below.

Primer 066549:
(SEQ ID NO: 17)
5'-TAGAACATCGTCCATAATGGCGGCTCCGTTTCGTCA-3'

Primer 067388:
(SEQ ID NO: 18)
5'-GTGTCAGTCACCTCTAGTTATTATTACGCTTTGACGATCT-3'

The PCR reaction was composed of 5 µl 10× reaction buffer, 1 µl *Aspergillus oryzae* NRRL3488 genomic DNA (110 ng/µl), 1 µl primer 066549 (100 ng/µl), 1 µl primer 067388 (100 ng/µl), 1 µl dNTP mixture (10 mM), 45.5 µl deionized water, and 0.5 µl Herculase® HotStart DNA polymerase. The amplification reaction was incubated in an EPPENDORF® MASTERCYCLER® programmed for 1 cycle at 95° C. for 2 minutes; 10 cycles each at 95° C. for 10 seconds, 58° C. for 30 seconds, and 72° C. for 3.5 minutes; 20 cycles each at 95° C. for 10 seconds, 58° C. for 30 seconds, and 72° C. for 3.5 minutes plus 10 seconds per cycle. The PCR product was then purified using a MinElute® PCR Purification Kit.

Figure 9:
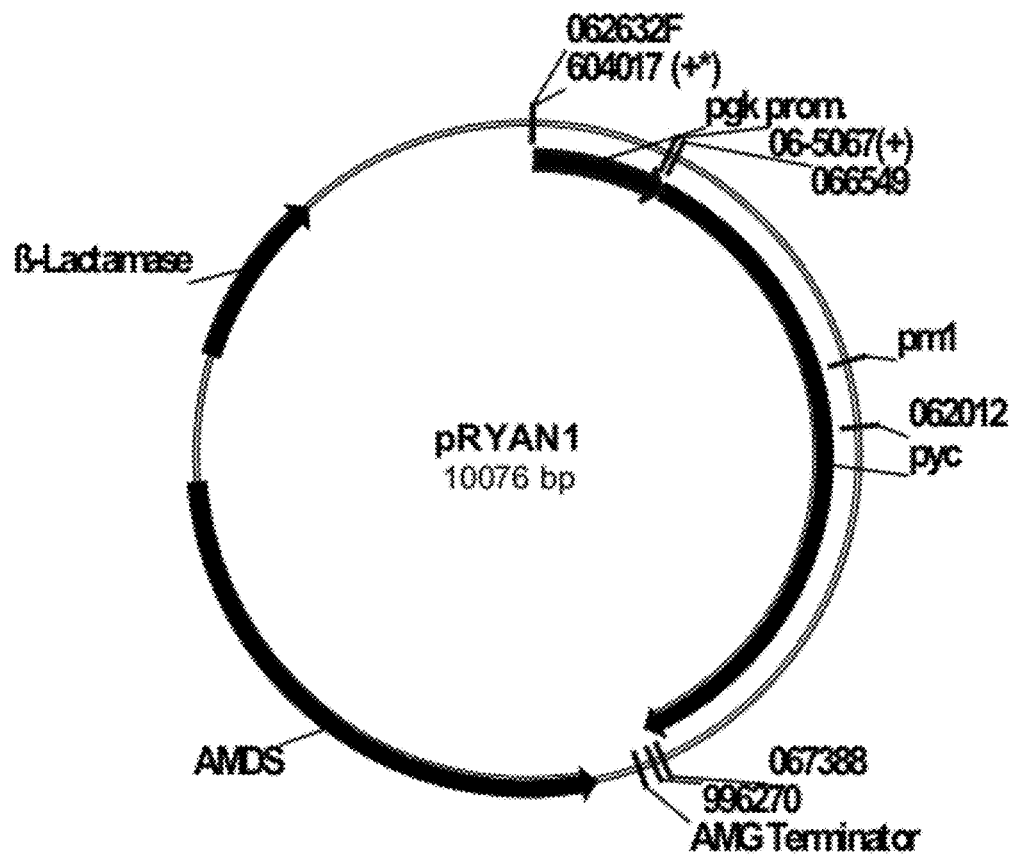
FIG. 9 shows a restriction map of pRYAN1.

The purified PCR product was inserted into the vector using an In-Fusion™ Advantage reaction composed of 2 µl 5× buffer, 1 µl purified PCR product (144 ng/µl), 2 µl gel purified Sex AI and Pac I restriction digested pShTh60 (FIG. 1; 78 ng/µl), 1 µl In-Fusion™ enzyme and 4 µl deionized water. The reaction was incubated at 37° C. for 15 minutes followed by 50° C. for 15 minutes after which it was placed on ice for 5 minutes and diluted with 40 µl TE buffer resulting in pRYAN1 (FIG. 9). A 2 µl aliquot of the ligation reaction was transformed into ONE SHOT® TOP10 chemically competent *E. coli* cells according to the manufacturer's instructions. Transformants were plated onto 2XYT+amp plates and incubated at 37° C. overnight. The resulting transformants were picked and subjected to DNA sequencing to confirm that the pyc gene was successfully integrated into the vector. Nucleotide 1308 was changed from C to T, but did not affect the protein sequence.

Example 10

Transformation of Expression Vector Fragments of pSaMF36, pSaMF21 and pRyan1 into *Aspergillus oryzae* NRRL 3488 (SaMF3603)

The vectors pSaMF36 (Example 4), pSaMF21 (Example 8) and pRyan1 (Example 9) were prepared for transformation by digestion with Pme I for 4 hours at 37° C. The digested vectors were separated on a 0.8% agarose TBE gel, a 5040 bp band was cut out for pSaMF36, a 5213 bp band was cut out for pSaMF21 and a 7429 bp band was cut out for pRyan1. The bands containing the expression cassettes were each purified using the Macherey-Nagel Nucleospin® Extract II Kit (Düren, Germany) according to manufacturer's instructions.

Three transformation reactions were prepared. For each transformation reaction, 100 µl of protoplast preparation (Example 2) were transferred to a 12 ml polypropylene tube. To this was added a total of five micrograms of amp marker free, linearized pShTh104, pSaMF21 and pRyan1 in equimolar quantities and 250 µl of polyethylene glycol (PEG) solution (60% w/v polyethylene glycol (PEG), 10 mM Tris 6.5, 10 mM CaCl) followed by gentle mixing and incubation at 37° C. for 30 minutes. Each transformation was diluted with 9 ml of STC buffer, followed by plating three separate 3 ml aliquots onto COVE plates. Each plate was then incubated at 34° C. for 7-10 days. The resulting transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 11

Production of Malic Acid in Shake Flask Cultures of *Aspergillus oryzae* Transformants Containing Expression Vector Fragments of pSaMF36, pSaMF21 and pRyan1 (SaMF3603)

Spores from each *Aspergillus oryzae* triple transformant SaMF3603 described in Example 10 and *Aspergillus oryzae* NRRL 3488 as a control were prepared as described in Example 3. Quantitation of malic acid for the shake flask culture transformants was performed as described in Example 3.

*Aspergillus oryzae* transformants SaMF3603 containing pSaMF36, pSaMF21 and pRyan1 showed an improvement in malic acid production of greater than 2.55-fold over the *Aspergillus oryzae* NRRL 3488 control strains.

Example 12

Fermentation of *Aspergillus oryzae* Transformants Containing Expression Vector Fragments of pSaMF36, pSaMF21 and pRyan1 (SaMF3603)

*Aspergillus oryzae* triple transformant SaMF3603 described in Example 10 and control transformant *Aspergillus oryzae* SaMF2103 (see PCT Application No. PCT/US10/47002, filed Aug. 27, 2010) were prepared and fermented as described in Example 7.

Quantitation of malic acid in the fermentations was performed as described in Example 3. The relative malic acid titer of *Aspergillus oryzae* triple transformants SaMF3603 were comparable to the *Aspergillus oryzae* transformants SaMF2103, indicating that the *Aspergillus oryzae* triple transformants SaMF3603 outperform both the *Aspergillus oryzae* pSaMF36 single transformants and the *Aspergillus oryzae* NRRL 3488 control based on comparisons previously described.

Example 13

Cloning of an *Aspergillus* Aculeatus C4-Dicarboxylic Acid Transporter Gene and Construction of Expression Vector pSaMF38

Figure 10:
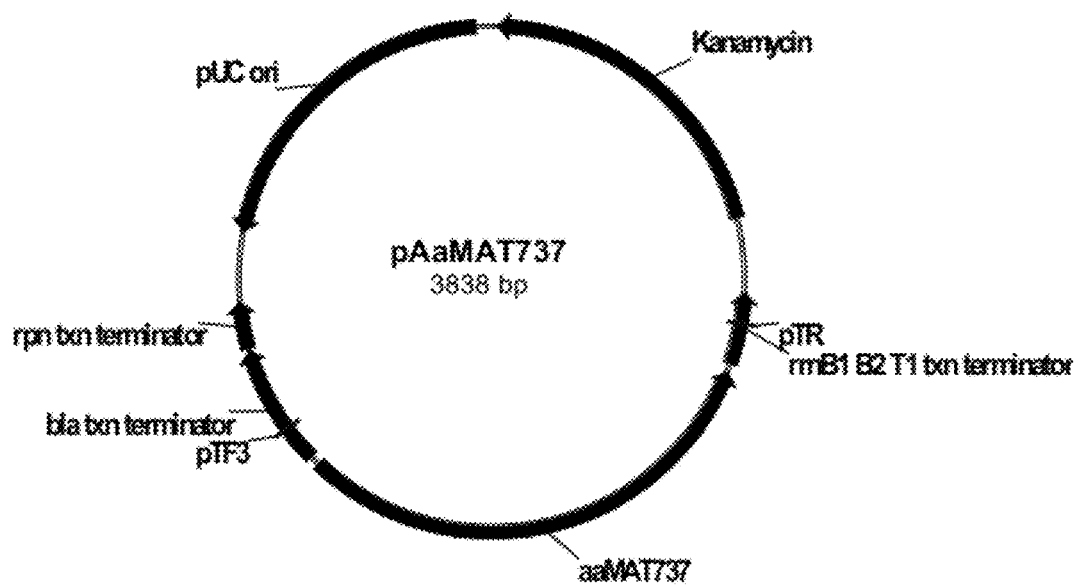
FIG. 10 shows a restriction map of pAaMAT737.

The 1194 bp C4-dicarboxylic acid transporter gene mat737 was synthetically constructed into pAaMAT737 (FIG. 10; DNA2.0, Menlo Park, Calif., USA). The mat737 gene was amplified from pAaMAT737 using primers 069698 and 069699 (Example 1).

The PCR reaction was composed of 10 µl 5× reaction buffer, 1 µl pAaMAT737 template (20 ng/µl), 1 µl primer 069698 (100 ng/µl), 1 µl primer 069699 (100 ng/µl), 1 µl dNTP mixture (10 mM), 35.5 µl deionized water, and 0.5 µl Phusion® Hot Start High-Fidelity DNA polymerase. The amplification reaction was incubated in an EPPENDORF® MASTERCYCLER® programmed for 1 cycle at 98° C. for 30 seconds; 30 cycles each at 98° C. for 10 seconds, 65° C. for 30 seconds, and 72° C. for 1 minute; 1 cycle at 72° C. for 10 minutes. The PCR reaction was digested with Dpn I for 1 hour to degrade any plasmid DNA template and the PCR product was purified using the MinElute® PCR Purification Kit.

Figure 11:
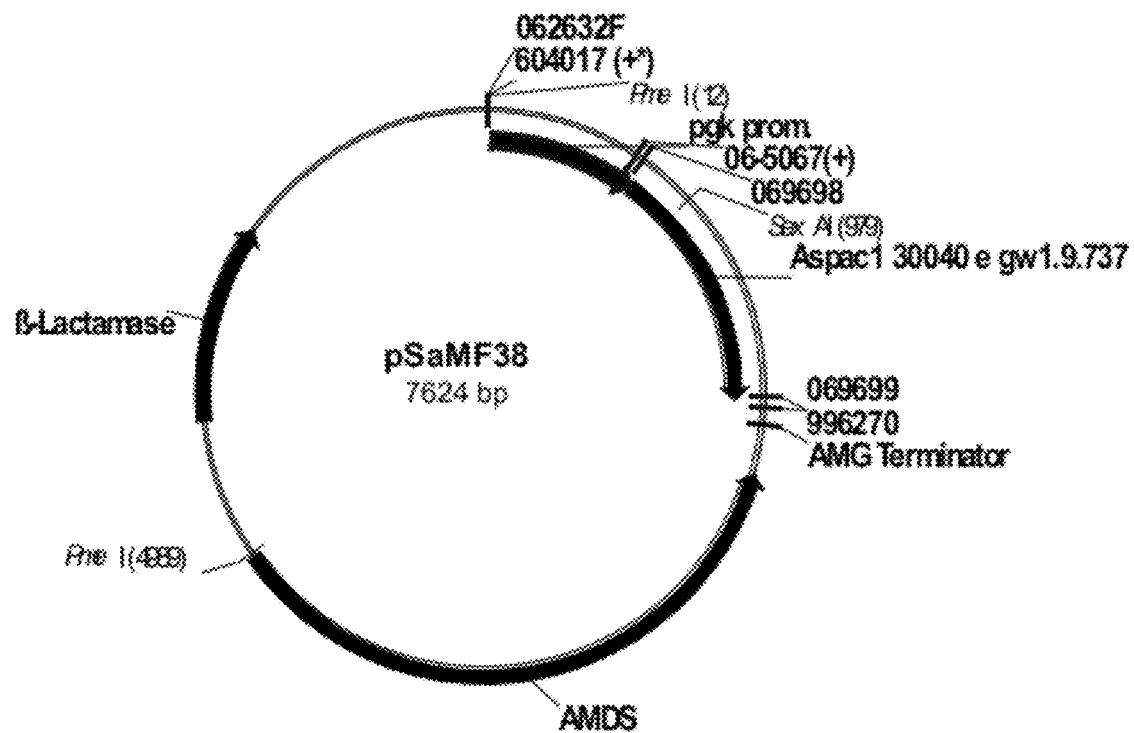
FIG. 11 shows a restriction map of pSaMF38.

Plasmid pShTh60 (FIG. 1) was digested with Sex AI and Pac I, separated by 0.8% agarose gel electrophoresis in TBE buffer (10.8 g/L Tris Base, 5.5 g/L Boric acid, 2 mM EDTA, pH 8.0) and purified using a QIAQUICK® Gel Extraction Kit. The purified PCR product above was then inserted into the digested pShTh60 fragment using an In-Fusion™ Advantage reaction kit composed of 2 µl 5× buffer, 0.5 µl purified PCR product (187 ng/µl), 1.5 µl digested and gel-purified pShTh60 (132 ng/µl), 1 µl In-Fusion™ enzyme and 5 µl deionized water. The reaction was incubated at 37° C. for 15 minutes, 50° C. for 15 minutes, placed on ice for 5 minutes and diluted with 40 µl TE buffer (10 mM Tris Base, 1 mM EDTA, pH 8.0) resulting in pSaMF38 (FIG. 11).

A 2.5 µl aliquot of the ligation reaction above containing pSaMF38 was transformed into ONE SHOT® TOP10 chemically competent *E. coli* cells according to the manufacturer's instructions. Transformants were plated onto 2XYT+amp plates and incubated at 37° C. overnight. The resulting transformants were picked and subjected to DNA sequencing to confirm that the mat737 gene was integrated into the vector.

Figure 12:
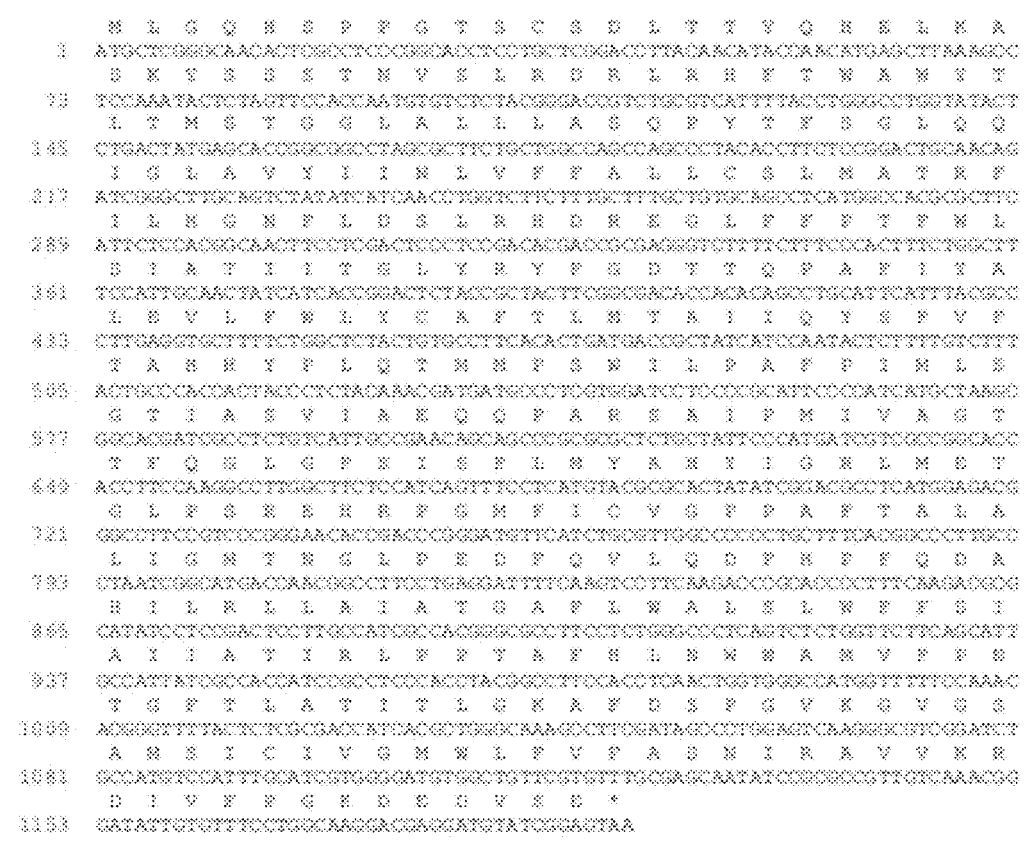

The nucleotide sequence (SEQ ID NO: 5) and deduced amino acid sequence (SEQ ID NO: 6) of the mat737 gene are shown in FIG. 12. The coding sequence is 1194 bp including the stop codon. The encoded predicted protein is 397 amino acids, with a predicted molecular mass of 44.3 kDa and an isoelectric pH of 7.32. The gene contains no introns. Using the InterProScan program (The European Bioinformatics Institute), a signal peptide of 68 residues was predicted. Based on this program, the predicted mature protein contains 329 amino acids with a predicted molecular mass of 36.6 kDa and an isoelectric pH of 6.52.

Example 14

Transformation of an Expression Vector Fragment pSaMF38 into *Aspergillus oryzae* NRRL 3488 (SaMF38)

Protoplast preparation and transformation of *Aspergillus oryzae* NRRL 3488 were performed as described in Example 2.

Plasmid pSaMF38 was prepared for transformation by restriction digestion with Pme I. The 4977 bp expression cassette was separated from the digested vector by 0.8% agarose gel electrophoresis in TBE buffer and purified using a Macherey-Nagel Nucleospin Extract II Kit. Two transformation reactions were prepared. For each transformation reaction, 100 µl of protoplast preparation was transferred to a 12 ml polypropylene tube, to which was added 5 µg of linearized pSaMF38 and 250 µl PEG solution (60% w/v polyethylene glycol (PEG), 10 mM Tris 6.5, 10 mM CaCl) followed by gentle mixing and incubation at 37° C. for 30 minutes. Each transformation was diluted with 9 ml of STC buffer, followed by plating three separate 3 ml aliquots onto COVE plates. Each plate was then incubated at 34° C. for 7-10 days. Twenty SaMF38 transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 15

Production of Malic Acid in Shake Flask Cultures of *Aspergillus oryzae* Transformants Containing an Expression Vector Fragment of pSaMF38 (SaMF38)

Spores from *Aspergillus oryzae* pSaMF38 transformants described in Example 14 and *Aspergillus oryzae* NRRL 3488 as a control were prepared as described in Example 3. Quantitation of malic acid for the shake flask culture transformants was performed as described in Example 3.

*Aspergillus oryzae* pSaMF38 transformant showed an improvement in malic acid production of greater than 1.8-fold over the *Aspergillus oryzae* NRRL 3488 control strains.

Example 16

Cloning of an *Aspergillus aculeatus* C4-Dicarboxylic Acid Transporter Gene and Construction of Expression Vector pSaMF41 Under Control of an Alternative Promoter The following examples demonstrate that an *Aspergillus aculeatus* C4-dicarboxylic acid transporter gene can be driven by using an alternative gpd promoter.

The 1257 bp C4-dicarboxylic acid transporter gene c4t521 was amplified from pSaMF36 (supra) using primers 0611384 and 069701 shown below.

```
Primer 0611384:
                                  (SEQ ID NO: 21)
5'-CCAACAGACACATCTAAACAATGCACGACCACAGCA-3'

Primer 069701:
                                  (SEQ ID NO: 22)
5'-GTGTCAGTCACCTCTAGTTATCATTCGAACAACTCGGACA-3'
```

The PCR reaction was composed of 5 µl 10× reaction buffer, 1 µl pSaMF36 template (50 ng/µl), 1 µl primer 0611384 (100 ng/µl), 1 µl primer 069701 (100 ng/µl), 1 µl dNTP mixture (10 mM), 40.5 µl deionized water, and 0.5 µl Herculase® HotStart DNA polymerase (Stratagene, La Jolla, Calif., USA). The amplification reaction was incubated in an EPPENDORF® MASTERCYCLER® programmed for 1 cycle at 95° C. for 2 minutes; 10 cycles each at 95° C. for 10 seconds, 60° C. for 30 seconds, and 72° C. for 1.5 minutes; 20 cycles each at 95° C. for 10 seconds, 60° C. for 30 seconds, and 72° C. for 1.5 minutes plus 10 seconds per cycle. The PCR reaction was subjected to restriction digestion with DpnI for 1 hour to degrade any plasmid DNA template. The PCR product was then purified using the MinElute® PCR Purification Kit (QIAGEN Inc.).

The purified PCR product was then inserted into a vector containing the gpd promoter (pShTh108) using an In-Fusion™ Advantage reaction composed of 2 µl 5× buffer, 0.6 µl purified PCR product (127 ng/µl), 1.75 µl gel-purified Hind III and Pac I restriction digested pShTh108 (114 ng/µl), 1 µl In-Fusion™ enzyme and 4.65 µl deionized water. The reaction was incubated at 37° C. for 15 minutes then 50° C. for 15 minutes, and then placed on ice for 5 minutes and diluted with 40 µl TE buffer resulting in pSaMF41.

A 2.5 µl aliquot of the ligation reaction was transformed into ONE SHOT® TOP10 chemically competent *E. coli* cells (Invitrogen) according to the manufacturer's instructions. Transformants were plated onto 2XYT+amp plates and incubated at 37° C. overnight. The resulting transformants were picked and subjected to DNA sequencing to confirm that the c4t521 gene was successfully integrated into the vector.

The nucleotide sequence (SEQ ID NO: 3) and deduced amino acid sequence (SEQ ID NO: 4) of the *Aspergillus aculeatus* c4t521 gene are shown in FIG. 5. The coding sequence is 1257 bp including the stop codon and is driven by the gpd promoter compared to the pgk promoter of Example 4.

Example 17

Transformation of an Expression Vector Fragment pSaMF41 into *Aspergillus oryzae* NRRL 3488 (SaMF41)

Protoplast preparation and transformation of *Aspergillus oryzae* 3488 were performed as described in Example 2.

Plasmid pSaMF41 was prepared for transformation by linearizing by restriction digestion with Pme I. The 5025 bp expression cassette was separated from the digested vector by 0.8% agarose gel electrophoresis in TBE buffer and purified using a Macherey-Nagel Nucleospin® Extract II Kit for gel isolation according to manufacturer's instructions. Two transformation reactions were prepared. For each transformation reaction, 100 µl of protoplast preparation was transferred to a 12 ml polypropylene tube. To this was added 5 µg of linearized pSaMF41 and 250 µl PEG solution (60% w/v polyethylene glycol (PEG), 10 mM Tris 6.5, 10 mM CaCl) followed by gentle mixing and incubation at 37° C. for 30 minutes. Each transformation was diluted with 9 ml of STC buffer, followed by plating three separate 3 ml aliquots onto COVE plates. Each plate was then incubated at 34° C. for 7-10 days. SaMF41 transformants were transferred to individual COVE plates and incubated at 34° C. for 5 days. Spore stocks were prepared by collecting the spores in 0.1% TWEEN® 80. Cultures were stored by preparing a glycerol stock of each (800 µl spore stock, 200 µl 0.1% TWEEN® 80) and frozen at −80° C.

Example 18

Production of Malic Acid in Shake Flask Cultures of *Aspergillus oryzae* Transformants Containing an Expression Vector Fragment of pSaMF41 (SaMF41)

Spores from each pSaMF41 transformant (SaMF41) described in Example 17, pSaMF36 transformant (SaMF36) described in Example 5, and *Aspergillus oryzae* NRRL 3488 as a control were prepared as described in Example 3. Quantitation of malic acid for the shake flask culture transformants was performed as described in Example 3.

*Aspergillus oryzae* SaMF41 transformants containing *Aspergillus aculeatus* c4t521 gene (SEQ ID NO: 3) driven by the gpd promoter showed comparable malic acid production to *Aspergillus oryzae* SaMF36 transformants containing *Aspergillus aculeatus* c4t521 gene (SEQ ID NO: 3) driven by the pgk promoter, and an increase in malic acid titer of about 2-fold compared to *Aspergillus oryzae* NRRL 3488 control lacking the c4t521 gene.

Example 19

Fermentation of *Aspergillus oryzae* Transformants Containing an Expression Vector Fragment of pSaMF41 (SaMF41)

*Aspergillus oryzae* pSaMF41 transformants described in Example 18 and control transformant *Aspergillus oryzae*

ShTh1040 (see PCT Application No. PCT/US10/47002, filed Aug. 27, 2010) were prepared and fermented as described in Example 7.

Quantitation of malic acid in the fermentations was performed as described above. The relative malic acid titer of *Aspergillus oryzae* pSaMF41 transformants were comparable to the *Aspergillus oryzae* ShTh1040 transformants, indicating that the *Aspergillus oryzae* pSaMF41 transformants outperform the *Aspergillus oryzae* NRRL 3488 control (which lack the overexpressed C4-dicarboxylic acid transporter gene) based on ShTh1040 and NRRL 3488 comparisons previously described.

Deposit of Biological Material

The following biological material has been deposited under the terms of the Budapest Treaty with the Agricultural Research Service Patent Culture Collection (NRRL), Northern Regional Research Center, 1815 University Street, Peoria, Ill., USA, and given the following accession number:

| Deposit | Accession Number | Date of Deposit |
|---|---|---|
| *Escherichia coli* pAaC4T737 | NRRL B-50400 | Jun. 17, 2010 |
| *Escherichia coli* pAaC4T521 | NRRL B-50388 | Jun. 4, 2010 |
| *Escherichia coli* pAaMAT737 | NRRL B-50401 | Jun. 17, 2010 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The present invention may be further described by the following numbered paragraphs:

[1] An isolated polypeptide having C4-dicarboxylic acid transporter activity, selected from:

(a) a polypeptide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2, 4, or 6, or the mature polypeptide sequence thereof;

(b) a polypeptide encoded by a polynucleotide that hybridizes under low stringency conditions, medium stringency conditions, medium-high stringency conditions, high stringency conditions, or very high stringency conditions with SEQ ID NO: 1, 3, or 5, the mature polypeptide coding sequence thereof, or the full-length complementary strand of the foregoing;

(c) a polypeptide encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1, 3, or 5, the mature polypeptide coding sequence thereof;

(d) a variant comprising a substitution, deletion, and/or insertion of one or more (e.g., two, several) amino acids of SEQ ID NO: 2, 4, or 6, or the mature polypeptide sequence thereof; and (e) a fragment of a polypeptide of (a), (b), (c), or (d) that has C4-dicarboxylic acid transporter activity.

[2] An isolated polypeptide having C4-dicarboxylic acid transporter activity, selected from:

(a) a polypeptide having at least 75%, e.g., at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 2 or the mature polypeptide sequence thereof;

(b) a polypeptide encoded by a polynucleotide that hybridizes under low stringency conditions, medium stringency conditions, medium-high stringency conditions, high stringency conditions, or very high stringency conditions with SEQ ID NO: 1, the mature polypeptide coding sequence thereof, or the full-length complementary strand of the foregoing;

(c) a polypeptide encoded by a polynucleotide having at least 75%, e.g., at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 1 or the mature polypeptide coding sequence thereof;

(d) a variant comprising a substitution, deletion, and/or insertion of one or more (e.g., two, several) amino acids of SEQ ID NO: 2 or the mature polypeptide sequence thereof; and (e) a fragment of a polypeptide of (a), (b), (c), or (d) that has C4-dicarboxylic acid transporter activity.

[3] An isolated polypeptide having C4-dicarboxylic acid transporter activity, selected from:

(a) a polypeptide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 4 or the mature polypeptide sequence thereof;

(b) a polypeptide encoded by a polynucleotide that hybridizes under low stringency conditions, medium stringency conditions, medium-high stringency conditions, high stringency conditions, or very high stringency conditions with SEQ ID NO: 3, the mature polypeptide coding sequence thereof, or the full-length complementary strand of the foregoing;

(c) a polypeptide encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 3 or the mature polypeptide coding sequence thereof;

(d) a variant comprising a substitution, deletion, and/or insertion of one or more (e.g., two, several) amino acids of SEQ ID NO: 4 or the mature polypeptide sequence thereof; and (e) a fragment of a polypeptide of (a), (b), (c), or (d) that has C4-dicarboxylic acid transporter activity.

[4] An isolated polypeptide having C4-dicarboxylic acid transporter activity, selected from:

(a) a polypeptide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 6 or the mature polypeptide sequence thereof;

(b) a polypeptide encoded by a polynucleotide that hybridizes under low stringency conditions, medium stringency conditions, medium-high stringency conditions, high stringency conditions, or very high stringency conditions with SEQ ID NO: 5, the mature polypeptide coding sequence thereof, or the full-length complementary strand of the foregoing;

(c) a polypeptide encoded by a polynucleotide having at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity to SEQ ID NO: 5 or the mature polypeptide coding sequence thereof;

(d) a variant comprising a substitution, deletion, and/or insertion of one or more (e.g., two, several) amino acids of SEQ ID NO: 6 or the mature polypeptide sequence thereof; and (e) a fragment of a polypeptide of (a), (b), (c), or (d) that has C4-dicarboxylic acid transporter activity.

[5] The polypeptide of any one of paragraphs [1]-[4], having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2, 4, or 6, or the mature polypeptide sequence thereof.

[6] The polypeptide of any one of paragraphs [1]-[5], which is encoded by a polynucleotide that hybridizes under low stringency conditions, low-medium stringency conditions, medium stringency conditions, medium-high stringency conditions, high stringency conditions, or very high stringency conditions with SEQ ID NO: 1, 3, or 5, the mature polypeptide coding sequence thereof, or the full-length complementary strand thereof.

[7] The polypeptide of any one of paragraphs [1]-[6], which is encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 1, 3, or 5, or the mature polypeptide coding sequence thereof.

[8] The polypeptide of any one of paragraphs [1]-[7], comprising or consisting of SEQ ID NO: 2, 4, or 6.

[9] The polypeptide of any one of paragraphs [1]-[7], comprising or consisting of the mature polypeptide of SEQ ID NO: 2, 4, or 6.

[10] The polypeptide of paragraph [9], wherein the mature polypeptide of SEQ ID NO: 2 is amino acids 62 to 397 or 69 to 397 of SEQ ID NO: 2.

[11] The polypeptide of paragraph [9], wherein the mature polypeptide of SEQ ID NO: 4 is amino acids 18 to 418 of SEQ ID NO: 4.

[12] The polypeptide of paragraph [9], wherein the mature polypeptide of SEQ ID NO: 6 is amino acids 69 to 397 of SEQ ID NO: 6.

[13] The polypeptide of any one of paragraphs [1]-[7], which is a fragment of SEQ ID NO: 2, 4, or 6, wherein the fragment has C4-dicarboxylic acid transporter activity.

[14] The polypeptide of any one of paragraphs [1]-[7], which is a variant comprising a substitution, deletion, and/or insertion of one or more (e.g., two, several) amino acids of SEQ ID NO: 2, 4, or 6, or the mature polypeptide sequence thereof.

[15] The polypeptide of any one of paragraphs [1]-[13], which is encoded by the polynucleotide contained in plasmid pAaC4T737 which is contained in *E. coli* NRRL B-50400.

[16] The polypeptide of any one of paragraphs [1]-[13] which is encoded by the polynucleotide contained in plasmid pAaC4t521 which is contained in *E. coli* NRRL B-50388.

[17] The polypeptide of any one of paragraphs [1]-[13], which is encoded by the polynucleotide contained in plasmid pAaMAT737 which is contained in *E. coli* NRRL B-50401.

[18] A composition comprising the polypeptide of any one of paragraphs [1]-[17].

[19] An isolated polynucleotide encoding the polypeptide of any one of paragraphs [1]-[17].

[20] A nucleic acid construct or expression vector comprising the polynucleotide of paragraph [19] operably linked to one or more (e.g., two, several) control sequences that direct the production of the polypeptide in an expression host.

[21] A recombinant host cell comprising the polynucleotide of paragraph [19] operably linked to one or more control sequences that direct the production of the polypeptide.

[22] A method of producing the polypeptide of any one of paragraphs [1]-[17], comprising:
(a) cultivating a cell, which in its wild-type form produces the polypeptide, under conditions conducive for production of the polypeptide; and
(b) recovering the polypeptide.

[23] A method of producing the polypeptide of any one of paragraphs [1]-[17], comprising:
(a) cultivating the recombinant host cell of paragraph [21] under conditions conducive for production of the polypeptide; and
(b) recovering the polypeptide.

[24] A transgenic plant, plant part or plant cell transformed with a polynucleotide encoding the polypeptide of any one of paragraphs [1]-[17].

[25] A method of producing the polypeptide of any one of paragraphs [1]-[17], comprising:
(a) cultivating the transgenic plant or the plant cell of paragraph [24] under conditions conducive for production of the polypeptide; and
(b) recovering the polypeptide.

[26] A method of producing a mutant of a parent cell, comprising inactivating a polynucleotide encoding the polypeptide of any one of paragraphs [1]-[17], which results in the mutant producing less of the polypeptide than the parent cell.

[27] A mutant cell produced by the method of paragraph [26].

[28] The mutant cell of paragraph [27], further comprising a gene encoding a native or heterologous protein.

[29] A method of producing a protein, comprising:
(a) cultivating the mutant cell of paragraph [27] or [28] under conditions conducive for production of the protein; and
(b) recovering the protein.

[30] A double-stranded inhibitory RNA (dsRNA) molecule comprising a subsequence of the polynucleotide of paragraph [19], wherein the dsRNA is optionally an siRNA or an miRNA molecule.

[31] The double-stranded inhibitory RNA (dsRNA) molecule of paragraph [30], which is about 15, 16, 17, 18, 19, 20, 21, 22, 23, 24, 25 or more duplex nucleotides in length.

[32] A method of inhibiting the expression of a polypeptide having C4-dicarboxylic acid transporter activity in a cell, comprising administering to the cell or expressing in the cell the double-stranded RNA (dsRNA) molecule of paragraph [30] or [31].

[33] A cell produced by the method of paragraph [31] or [32].

[34] The cell of paragraph [33], further comprising a gene encoding a native or heterologous protein.

[35] A method of producing a protein, comprising:
(a) cultivating the cell of paragraph [33] or [34] under conditions conducive for production of the protein; and
(b) recovering the protein.

[36] An isolated polynucleotide encoding a signal peptide comprising or consisting of amino acids 1 to 61 or 1 to 68 of SEQ ID NO: 2.

[37] An isolated polynucleotide encoding a signal peptide comprising or consisting of amino acids 1 to 17 of SEQ ID NO: 4.

[38] An isolated polynucleotide encoding a signal peptide comprising or consisting of amino acids 1 to 68 of SEQ ID NO: 6.

[39] A nucleic acid construct or expression vector comprising a gene encoding a protein operably linked to the polynucleotide of any of paragraphs [36]-[38], wherein the gene is foreign to the polynucleotide encoding the signal peptide.

[40] A recombinant host cell comprising the nucleic acid construct or expression vector of paragraph [39].

[41] A method of producing a protein, comprising:
(a) cultivating a recombinant host cell of paragraph [40] under conditions conducive for production of the protein; and
(b) recovering the protein.

[42] A method of producing a C4-dicarboxylic acid, comprising:
(a) cultivating a host cell comprising a heterologous polynucleotide encoding the polypeptide of any one of paragraphs [1]-[17] in a medium; and
(b) recovering the C4-dicarboxylic acid.

[43] A method for increasing C4-dicarboxylic acid production, comprising:
(a) transforming into a host cell a heterologous polynucleotide encoding the polypeptide of any one of paragraphs [1]-[17];
(b) cultivating the transformed organism in a medium; and
(c) recovering the C4-dicarboxylic acid.

[44] The method of paragraph [42] or [43], wherein the heterologous polynucleotide is operably linked to a promoter foreign to the polynucleotide.

[45] The method of any one of paragraphs [42]-[44], wherein the host cell further comprises a heterologous second polynucleotide encoding a malate dehydrogenase (e.g., the mature polypeptide coding sequence of SEQ ID NO: 11, or any described aspect thereof).

[46] The method of paragraph [45], wherein the heterologous second polynucleotide is operably linked to a promoter foreign to the polynucleotide.

[47] The method of any one of paragraphs [42]-[46], wherein the host cell further comprises a heterologous third polynucleotide encoding a pyruvate carboxylase (e.g., the mature polypeptide coding sequence of SEQ ID NO: 15, or any described aspect thereof).

[48] The method of paragraph [47], wherein the heterologous third polynucleotide is operably linked to a promoter foreign to the polynucleotide.

[49] The method of any one of paragraphs [42]-[48], wherein the host cell is a filamentous fungal host cell.

[50] The method of paragraph [49], wherein the filamentous fungal host cell is selected from an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Rhizopus*, *Schizophyllum*, *Talaromyces*, *Thermoascus*, *Thielavia*, *Tolypocladium*, *Trametes*, and *Trichoderma*.

[51] The method of paragraph [50], wherein the host cell is an *Aspergillus* host cell.

[52] The method of paragraph [50], wherein the host cell is an *Aspergillus oryzae* host cell.

[53] The method of any one of paragraphs [42]-[52], wherein the medium is a fermentable medium.

[54] The method of any one of paragraphs [42]-[53], wherein the C4-dicarboxylic acid is at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 300 g/L, about 150 g/L and about 250 g/L, about 175 g/L and about 225 g/L, or about 190 g/L and about 210 g/L.

[55] The method of any one of paragraphs [42]-[54], wherein the level of the C4-dicarboxylic acid is increased by at least 25%, e.g., at least 50%, at least 100%, at least 150%, at least 200%, at least 300%, or at 500% compared to the host cell without the polynucleotide encoding the C4-dicarboxylic acid transporter when cultivated under the same conditions.

[56] The method of any one of paragraphs [42]-[55], wherein the C4-dicarboxylic acid is selected from malic acid, succinic acid, oxaloacetic acid, malonic acid, and fumaric acid.

[57] The method of paragraph [56], wherein the C4-dicarboxylic acid is malic acid.

[58] A host cell comprising a heterologous polynucleotide encoding the polypeptide of any one of paragraphs [1]-[17]; wherein the host cell is capable of secreting an increased level of C4-dicarboxylic acid compared to the host cell without the heterologous polynucleotide when cultivated under the same conditions.

[59] The host cell of paragraph [58], wherein the heterologous polynucleotide is operably linked to a promoter foreign to the polynucleotide.

[60] The host cell of paragraph [57] or [58], further comprising a heterologous second polynucleotide encoding a malate dehydrogenase (e.g., the mature polypeptide coding sequence of SEQ ID NO: 11, or any described aspect thereof).

[61] The host cell of paragraph [60], wherein the heterologous second polynucleotide is operably linked to a promoter foreign to the polynucleotide.

[62] The host cell of any one of paragraphs [58]-[61], further comprising a heterologous third polynucleotide encoding a pyruvate carboxylase (e.g., the mature polypeptide coding sequence of SEQ ID NO: 15, or any described aspect thereof).

[62] The host cell of paragraph [62], wherein the heterologous third polynucleotide is operably linked to a promoter foreign to the polynucleotide.

[63] The host cell of any one of paragraphs [58]-[62], wherein the host cell is a filamentous fungal host cell.

[64] The filamentous fungal host cell of paragraph [63], wherein the host cell is selected from an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Rhizopus*, *Schizophyllum*, *Talaromyces*, *Thermoascus*, *Thielavia*, *Tolypocladium*, *Trametes*, and *Trichoderma*.

[65] The filamentous fungal host cell of paragraph [64], wherein the host cell is an *Aspergillus* host cell.

[66] The filamentous fungal host cell of paragraph [64], wherein the host cell is an *Aspergillus oryzae* host cell.

[67] The host cell of any one of paragraphs [58]-[66], wherein the cell is capable of C4-dicarboxylic acid volumetric productivity greater than about 0.1 g/L per hour, e.g., greater than about 0.2 g/L per hour, 0.5 g/L per hour, 0.6 g/L per hour, 0.7 g/L per hour, 0.8 g/L per hour, 0.9 g/L per hour, 1.0 g/L per hour, 1.1 g/L per hour, 1.2 g/L per hour, 1.3 g/L per hour, 1.5 g/L per hour, 1.75 g/L per hour, 2.0 g/L per hour, 2.25 g/L per hour, 2.5 g/L per hour, or 3.0 g/L per hour; or between about 0.1 g/L per hour and about 2.0 g/L per hour, e.g., between about 0.3 g/L per hour and about 1.7 g/L per hour, about 0.5 g/L per hour and about 1.5 g/L per hour, about 0.7 g/L per hour and about 1.3 g/L per hour, about 0.8 g/L per hour and about 1.2 g/L per hour, or about 0.9 g/L per hour and about 1.1 g/L per hour.

[68] The host cell of any one of paragraphs [58]-[67], wherein the host cell is capable of secreting an increased level of the C4-dicarboxylic acid of at least 25%, e.g., at least 50%, at least 100%, at least 150%, at least 200%, at least 300%, or at 500% compared to the host cell without the polynucleotide encoding the heterologous first polynucleotide when cultivated under the same conditions.

[69] The host cell of any one of paragraphs [58]-[68], wherein the C4-dicarboxylic acid is selected from malic acid, succinic acid, oxaloacetic acid, malonic acid, and fumaric acid.

[70] The host cell of paragraph [69], wherein the C4-dicarboxylic acid is malic acid.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A host cell comprising a heterologous polynucleotide that encodes a C4-dicarboxylic acid transporter, wherein the heterologous polynucleotide:
   (a) encodes a C4-dicarboxylic acid transporter having at least 95% sequence identity to SEQ ID NO: 4, or the mature polypeptide sequence thereof;
   (b) hybridizes under high stringency conditions with the full-length complementary strand of SEQ ID NO: 3; or
   (c) has at least 95% sequence identity to SEQ ID NO: 3, or the mature polypeptide coding sequence thereof;
   wherein the host cell is capable of producing a greater amount of C4 dicarboxylic acid compared to the host cell without the heterologous polynucleotide when cultivated under the same conditions.

2. The host cell of claim 1, wherein the heterologous polynucleotide encodes a C4-dicarboxylic acid transporter having at least 95% sequence identity to SEQ ID NO: 4, or the mature polypeptide sequence thereof.

3. The host cell of claim 1, wherein the heterologous polynucleotide encodes a C4-dicarboxylic acid transporter having at least 95% sequence identity to amino acids 18 to 418 of SEQ ID NO: 4.

4. The host cell of claim 1, wherein the heterologous polynucleotide encodes a C4-dicarboxylic acid transporter having at least 97% sequence identity to amino acids 18 to 418 of SEQ ID NO: 4.

5. The host cell of claim 1, wherein the heterologous polynucleotide encodes a C4-dicarboxylic acid transporter having at least 98% sequence identity to amino acids 18 to 418 of SEQ ID NO: 4.

6. The host cell of claim 1, wherein the heterologous polynucleotide encodes a C4-dicarboxylic acid transporter having at least 99% sequence identity to amino acids 18 to 418 of SEQ ID NO: 4.

7. The host cell of claim 1, wherein the heterologous polynucleotide encodes a C4-dicarboxylic acid transporter comprising or consisting of SEQ ID NO: 4, or the mature polypeptide sequence thereof.

8. The host cell of claim 1, wherein the heterologous polynucleotide encodes a C4-dicarboxylic acid transporter comprising or consisting of amino acids 18 to 418 of SEQ ID NO: 4.

9. The host cell of claim 1, wherein the C4-dicarboxylic acid transporter comprises the same sequence as the polypeptide encoded by the polynucleotide contained in plasmid pAaC4t521 which is contained in *E. coli* NRRL B-50388.

10. The host cell of claim 1, wherein the heterologous polynucleotide hybridizes under high stringency conditions with the full-length complementary strand of SEQ ID NO: 3.

11. The host cell of claim 1, wherein the heterologous polynucleotide hybridizes under very high stringency conditions with the full-length complementary strand of SEQ ID NO: 3.

12. The host cell of claim 1, wherein the heterologous polynucleotide has at least 95% sequence identity to SEQ ID NO: 3, or the mature polypeptide coding sequence thereof.

13. The host cell of claim 1, wherein the heterologous polynucleotide has at least 95% sequence identity to nucleotides 52 to 1257 of SEQ ID NO: 3.

14. The host cell of claim 1, wherein the heterologous polynucleotide has at least 97% sequence identity to nucleotides 52 to 1257 of SEQ ID NO: 3.

15. The host cell of claim 1, wherein the heterologous polynucleotide has at least 98% sequence identity to nucleotides 52 to 1257 of SEQ ID NO: 3.

16. The host cell of claim 1, wherein the heterologous polynucleotide has at least 99% sequence identity to nucleotides 52 to 1257 of SEQ ID NO: 3.

17. The host cell of claim 1, wherein the heterologous polynucleotide comprises or consists of SEQ ID NO: 3, or the mature polypeptide coding sequence thereof.

18. The host cell of claim 1, wherein the heterologous polynucleotide comprises or consists of nucleotides 52 to 1257 of SEQ ID NO: 3.

19. The host cell of claim 1, wherein the heterologous polynucleotide is operably linked to a promoter foreign to the polynucleotide.

20. The host cell of claim 1, further comprising a heterologous polynucleotide encoding a malate dehydrogenase.

21. The host cell of claim 1, further comprising a heterologous polynucleotide encoding a pyruvate carboxylase.

22. The host cell of claim 1, wherein the host cell is a filamentous fungal host cell.

23. The filamentous fungal host cell of claim 22, wherein the host cell is an *Aspergillus* host cell.

24. The filamentous fungal host cell of claim 23, wherein the host cell is an *Aspergillus oryzae* host cell.

25. The filamentous fungal host cell of claim 23, wherein the host cell is an *Aspergillus niger* host cell.

26. The host cell of claim 1, wherein the host cell is a yeast host cell.

27. The host cell of claim 1, wherein the host cell is a bacterial host cell.

28. The host cell of claim 1, wherein the C4-dicarboxylic acid is malic acid.

29. The host cell of claim 1, wherein the cell is capable of C4-dicarboxylic acid volumetric productivity greater than 1.5 g/L per hour.

30. A filamentous fungal host cell comprising a heterologous polynucleotide that encodes a C4-dicarboxylic acid transporter, wherein:

the heterologous polynucleotide is operably linked to a promoter foreign to the polynucleotide;

the heterologous polynucleotide encodes a C4-dicarboxylic acid transporter having at least 95% sequence identity to amino acids 18 to 418 of SEQ ID NO: 4; and the host cell is capable of producing a greater amount of malic acid compared to the host cell without the heterologous polynucleotide when cultivated under the same conditions.

31. A method of producing a C4-dicarboxylic acid, comprising:

(a) cultivating the host cell of claim 1 in a medium under suitable conditions to produce a C4-dicarboxylic acid; and (b) recovering the C4-dicarboxylic acid.

32. The method of claim 31, wherein the heterologous polynucleotide encodes a C4-dicarboxylic acid transporter having at least 95% sequence identity to amino acids 18 to 418 of SEQ ID NO: 4.

33. The method of claim 31, wherein the C4 dicarboxylic acid is malic acid.

* * * * *

SEQUENCE LISTING

```
<160> NUMBER OF SEQ ID NOS: 22

<210> SEQ ID NO 1
<211> LENGTH: 1194
<212> TYPE: DNA
<213> ORGANISM: Aspergillus aculeatus

<400> SEQUENCE: 1
atgctcgggc aacatccgcc tcccgacacc tcctgctcgg accttacaac ataccagcat    60
gagctcaaag cctccaaata ctctagttcc accaatgtgt ctctacggga ccgtctgcgt   120
cattttacct gggcgtggta tactctgact atgagcaccg gcggtctagc cctcctgctg   180
gccagccagc cctactcctt ctccggactg caacagatcg ggcttgcagt ctacatcatc   240
aacctggcct tctttgcgtt gctgtgtagc ctcatggccc acgcttcat tctccacggc    300 aacttcctcg actccctccg acacgaccgc gagggtcttt tctttcctac tttctggctt   360
tctattgcaa ctatcatcac cggcctgtac cgctacttcg gcgacaccac acagcctgca   420
ttcatttacg ctcttgaggt gctcttctgg ctctactgtg ccttcactct gatgaccgct   480
attatccaat actcctttgt cttaccgcc caccactacc ctctacaaac gatgatgccc   540
tcatggatcc tccccgcatt ccctatcatg ctcagcggca cgatcgcctc cgtcattgcc   600
gaacagcagc ccgcgcgctc tgctattccc atgatcgtcg ccggcaccac cttccaaggc   660
cttggcttct ccatcagttt cctcatgtac gcgcactata tcgggcggct catggagacg   720
ggccttccgt cccgggaaca ccgacccggg atgttcatct gcgttggccc cccggctttc   780
acggcccttg ccctaatcgg catgaccaac ggccttcctg aggattttca agtccttcaa   840
gacccgcacc cctttcaaga cgcgcacatc ctccgactcc ttgccatcgc cacgggcgcc   900
ttcctctggg ccctcagtct ctggttcttt agcattgcca tcatcgccac catccgcctc   960
ccacctacag ccttccacct caactggtgg gccatggttt ttccaaacac gggttttact  1020
ctcgcgacca tcacgctggg caaagccttc gatagccctg gagtcaaggg cgtcggatct  1080
gccatgtcca tttgcatcgt ggggatgtgg ctgttcgtgt ttgcgagcaa tatccgtgcc  1140
gttgtcaaac gggatattgt tttccctggg aaggacgagg atgtatcgga gtaa         1194

<210> SEQ ID NO 2
<211> LENGTH: 397
<212> TYPE: PRT
<213> ORGANISM: Aspergillus aculeatus

<400> SEQUENCE: 2
```

Met Leu Gly Gln His Pro Pro Asp Thr Ser Cys Ser Asp Leu Thr
1               5                   10                  15

Thr Tyr Gln His Glu Leu Lys Ala Ser Lys Tyr Ser Ser Ser Thr Asn
            20                  25                  30

Val Ser Leu Arg Asp Arg Leu Arg His Phe Thr Trp Ala Trp Tyr Thr
        35                  40                  45

Leu Thr Met Ser Thr Gly Gly Leu Ala Leu Leu Ala Ser Gln Pro
    50                  55                  60

Tyr Ser Phe Ser Gly Leu Gln Gln Ile Gly Leu Ala Val Tyr Ile Ile
65                  70                  75                  80

Asn Leu Ala Phe Phe Ala Leu Leu Cys Ser Leu Met Ala Ala Arg Phe
                85                  90                  95

Ile Leu His Gly Asn Phe Leu Asp Ser Leu Arg His Asp Arg Glu Gly
            100                 105                 110

Leu Phe Phe Pro Thr Phe Trp Leu Ser Ile Ala Thr Ile Ile Thr Gly
        115                 120                 125

Leu Tyr Arg Tyr Phe Gly Asp Thr Thr Gln Pro Ala Phe Ile Tyr Ala
    130                 135                 140

Leu Glu Val Leu Phe Trp Leu Tyr Cys Ala Phe Thr Leu Met Thr Ala
145                 150                 155                 160

Ile Ile Gln Tyr Ser Phe Val Phe Thr Ala His His Tyr Pro Leu Gln
                165                 170                 175

Thr Met Met Pro Ser Trp Ile Leu Pro Ala Phe Pro Ile Met Leu Ser
            180                 185                 190

Gly Thr Ile Ala Ser Val Ile Ala Glu Gln Gln Pro Ala Arg Ser Ala
        195                 200                 205

Ile Pro Met Ile Val Ala Gly Thr Thr Phe Gln Gly Leu Gly Phe Ser
    210                 215                 220

Ile Ser Phe Leu Met Tyr Ala His Tyr Ile Gly Arg Leu Met Glu Thr
225                 230                 235                 240

Gly Leu Pro Ser Arg Glu His Arg Pro Gly Met Phe Ile Cys Val Gly
                245                 250                 255

Pro Pro Ala Phe Thr Ala Leu Ala Leu Ile Gly Met Thr Asn Gly Leu
            260                 265                 270

Pro Glu Asp Phe Gln Val Leu Gln Asp Pro His Pro Phe Gln Asp Ala
        275                 280                 285

His Ile Leu Arg Leu Leu Ala Ile Ala Thr Gly Ala Phe Leu Trp Ala
    290                 295                 300

Leu Ser Leu Trp Phe Phe Ser Ile Ala Ile Ala Thr Ile Arg Leu
305                 310                 315                 320

Pro Pro Thr Ala Phe His Leu Asn Trp Trp Ala Met Val Phe Pro Asn
                325                 330                 335

Thr Gly Phe Thr Leu Ala Thr Ile Thr Leu Gly Lys Ala Phe Asp Ser
            340                 345                 350

Pro Gly Val Lys Gly Val Gly Ser Ala Met Ser Ile Cys Ile Val Gly
        355                 360                 365

Met Trp Leu Phe Val Phe Ala Ser Asn Ile Arg Ala Val Val Lys Arg
    370                 375                 380

Asp Ile Val Phe Pro Gly Lys Asp Glu Asp Val Ser Glu
385                 390                 395

<210> SEQ ID NO 3
<211> LENGTH: 1257
<212> TYPE: DNA

<213> ORGANISM: Aspergillus aculeatus

<400> SEQUENCE: 3

```
atgcacgacc acagcactgg atctagtcca tacatctcgg acgtggaaac cttgaaccac      60
gcctgcgaga agtccgtcaa ccccgagacc aaagtctccc agcctcagga atctcccatt     120
atcagcaata atgaacatca ggagtttgtt aagctgggca tccgccaacg gctgcgtcat     180
ttcacctggg cctggtatac cctaaccatg agcgcaggtg gactggccct tcttctccgc     240
aaccagccgt atcaattcaa ggggttgaag gagataggcc tggtggtata catagccaat     300
ctcgtcttct ttactatcat cggctctctt atgatcacca ggtttgttct ttacaacaac     360
ctgatggact ctctccgcca cgaccgagaa ggtttcttct ttccaacctt ctggctctcc     420
atcgccacca tgattagtgg tctatctgcc tacttctcta ctgaagacac gcaccgcctc     480
aattatgctc tcgagggtct cttctgggcg tactgtatct tcacgtttgc ctcagcagtg     540
atccagtact cctttgtctt ctcctatcac acgttccctc tgcaaactat gatgccatca     600
tggatcttac cggcattccc tatcatgctg agcggaacca ttgcctctgc cgcttccagc     660
taccagcctg cggtgtctgc cacgcctatg attgttgccg catcacgtt ccagggactc      720
ggattctgca tcagcttcat gatgtacgcc cactacatcg ggcgtctgat ggagacgggc     780
atcccttcga gcgagcaccg tcctggtatg ttcatctgtg tcggccccc tgccttcacg      840
ctgctggcta tcatcggcat ggccaacggc cttcccgagg cttcagtat cctgggcgat      900
ggtggcatgg acgaccgtca catcatgcga gtactggccg tctgcgcggg catgttcctc     960
tgggctctga gcatttggtt cttctgtgtc gctctgggct cagttgtgcg ggcgcctccc    1020
catgatttcc acctcaactg gtgggctatg gtcttcccta caccggact cactctcgcc     1080
accatcaccc tggccaagtc actggacagt gccgcgttga atgggtggg cgtgggcatg     1140
tccctctgcg tgatctgcat gttcatcttc gtcttcgtga gcaccattag gctgttctc     1200
ttgaagagga tcatgtggcc aggtcgggat gaggatgtgt ccgagttgtt cgaatga      1257
```

<210> SEQ ID NO 4
<211> LENGTH: 418
<212> TYPE: PRT
<213> ORGANISM: Aspergillus aculeatus

<400> SEQUENCE: 4

```
Met His Asp His Ser Thr Gly Ser Ser Pro Tyr Ile Ser Asp Val Glu
1               5                   10                  15

Thr Leu Asn His Ala Cys Glu Lys Ser Val Asn Pro Glu Thr Lys Val
            20                  25                  30

Ser Gln Pro Gln Glu Ser Pro Ile Ile Ser Asn Asn Glu His Gln Glu
        35                  40                  45

Phe Val Lys Leu Gly Ile Arg Gln Arg Leu Arg His Phe Thr Trp Ala
    50                  55                  60

Trp Tyr Thr Leu Thr Met Ser Ala Gly Gly Leu Ala Leu Leu Leu Arg
65                  70                  75                  80

Asn Gln Pro Tyr Gln Phe Lys Gly Leu Lys Glu Ile Gly Leu Val Val
                85                  90                  95

Tyr Ile Ala Asn Leu Val Phe Phe Thr Ile Ile Gly Ser Leu Met Ile
            100                 105                 110

Thr Arg Phe Val Leu Tyr Asn Asn Leu Met Asp Ser Leu Arg His Asp
        115                 120                 125

Arg Glu Gly Phe Phe Phe Pro Thr Phe Trp Leu Ser Ile Ala Thr Met
    130                 135                 140
```

```
Ile Ser Gly Leu Ser Ala Tyr Phe Ser Thr Glu Asp Thr His Arg Leu
145                 150                 155                 160

Asn Tyr Ala Leu Glu Gly Leu Phe Trp Ala Tyr Cys Ile Phe Thr Phe
                165                 170                 175

Ala Ser Ala Val Ile Gln Tyr Ser Phe Val Phe Ser Tyr His Thr Phe
            180                 185                 190

Pro Leu Gln Thr Met Met Pro Ser Trp Ile Leu Pro Ala Phe Pro Ile
        195                 200                 205

Met Leu Ser Gly Thr Ile Ala Ser Ala Ala Ser Ser Tyr Gln Pro Ala
    210                 215                 220

Val Ser Ala Thr Pro Met Ile Val Ala Gly Ile Thr Phe Gln Gly Leu
225                 230                 235                 240

Gly Phe Cys Ile Ser Phe Met Met Tyr Ala His Tyr Ile Gly Arg Leu
                245                 250                 255

Met Glu Thr Gly Ile Pro Ser Ser Glu His Arg Pro Gly Met Phe Ile
                260                 265                 270

Cys Val Gly Pro Pro Ala Phe Thr Leu Leu Ala Ile Ile Gly Met Ala
            275                 280                 285

Asn Gly Leu Pro Glu Gly Phe Ser Ile Leu Gly Asp Gly Gly Met Asp
        290                 295                 300

Asp Arg His Ile Met Arg Val Leu Ala Val Cys Ala Gly Met Phe Leu
305                 310                 315                 320

Trp Ala Leu Ser Ile Trp Phe Phe Cys Val Ala Leu Gly Ser Val Val
                325                 330                 335

Arg Ala Pro Pro His Asp Phe His Leu Asn Trp Trp Ala Met Val Phe
                340                 345                 350

Pro Asn Thr Gly Leu Thr Leu Ala Thr Ile Thr Leu Ala Lys Ser Leu
            355                 360                 365

Asp Ser Ala Ala Leu Lys Trp Val Gly Val Gly Met Ser Leu Cys Val
370                 375                 380

Ile Cys Met Phe Ile Phe Val Phe Val Ser Thr Ile Arg Ala Val Leu
385                 390                 395                 400

Leu Lys Arg Ile Met Trp Pro Gly Arg Asp Glu Asp Val Ser Glu Leu
                405                 410                 415

Phe Glu

<210> SEQ ID NO 5
<211> LENGTH: 1194
<212> TYPE: DNA
<213> ORGANISM: Aspergillus aculeatus

<400> SEQUENCE: 5
atgctcgggc aacactcgcc tcccggcacc tcctgctcgg accttacaac ataccaacat      60
gagcttaaag cctccaaata ctctagttcc accaatgtgt ctctacggga ccgtctgcgt     120
cattttacct gggcctggta tactctgact atgagcaccg gcggcctagc gcttctgctg     180
gccagccagc cctacacctt ctccggactg caacagatcg gcttgcagt  ctatatcatc     240 aacctggtct tctttgcttt gctgtgcagc ctcatggcca cgcgcttcat tctccacggc     300
aacttcctcg actccctccg acacgaccgc gagggtcttt tctttcccac tttctggctt     360
tccattgcaa ctatcatcac cggactctac cgctacttcg gcgacaccac acagcctgca     420
ttcatttacg cccttgaggt gctttttctgg ctctactgtg ccttcacact gatgaccgct     480
atcatccaat actcttttgt ctttactgcc caccactacc ctctacaaac gatgatgccc     540
```

```
tcgtggatcc tccccgcatt ccccatcatg ctaagcggca cgatcgcctc tgtcattgcc    600
gaacagcagc cgcgcgctc tgctattccc atgatcgtcg ccggcaccac cttccaaggc    660
cttggcttct ccatcagttt cctcatgtac gcgcactata tcggacgcct catggagacg    720
ggccttccgt cccgggaaca ccgacccggg atgttcatct gcgttggccc ccctgctttc    780
acggcccttg ccctaatcgg catgaccaac ggccttcctg aggattttca agtccttcaa    840
gacccgcacc cctttcaaga cgcgcatatc ctccgactcc ttgccatcgc acgggcgcc    900 ttcctctggg ccctcagtct ctggttcttc agcattgcca ttatcgccac catccgcctc    960
ccacctacgg ccttccacct caactggtgg gccatggttt ttccaaacac gggttttact   1020
ctcgcgacca tcacgctggg caaagccttc gatagccctg gagtcaaggg cgtcggatct   1080
gccatgtcca tttgcatcgt ggggatgtgg ctgttcgtgt ttgcgagcaa tatccgcgcc   1140
gttgtcaaac gggatattgt gtttcctggc aaggacgagg atgtatcgga gtaa         1194
```

<210> SEQ ID NO 6
<211> LENGTH: 397
<212> TYPE: PRT
<213> ORGANISM: Aspergillus aculeatus

<400> SEQUENCE: 6

```
Met Leu Gly Gln His Ser Pro Pro Gly Thr Ser Cys Ser Asp Leu Thr
1               5                   10                  15

Thr Tyr Gln His Glu Leu Lys Ala Ser Lys Tyr Ser Ser Ser Thr Asn
            20                  25                  30

Val Ser Leu Arg Asp Arg Leu Arg His Phe Thr Trp Ala Trp Tyr Thr
        35                  40                  45

Leu Thr Met Ser Thr Gly Gly Leu Ala Leu Leu Ala Ser Gln Pro
    50                  55                  60

Tyr Thr Phe Ser Gly Leu Gln Gln Ile Gly Leu Ala Val Tyr Ile Ile
65                  70                  75                  80

Asn Leu Val Phe Phe Ala Leu Leu Cys Ser Leu Met Ala Thr Arg Phe
                85                  90                  95

Ile Leu His Gly Asn Phe Leu Asp Ser Leu Arg His Asp Arg Glu Gly
            100                 105                 110

Leu Phe Phe Pro Thr Phe Trp Leu Ser Ile Ala Thr Ile Ile Thr Gly
        115                 120                 125

Leu Tyr Arg Tyr Phe Gly Asp Thr Thr Gln Pro Ala Phe Ile Tyr Ala
    130                 135                 140

Leu Glu Val Leu Phe Trp Leu Tyr Cys Ala Phe Thr Leu Met Thr Ala
145                 150                 155                 160

Ile Ile Gln Tyr Ser Phe Val Phe Thr Ala His His Tyr Pro Leu Gln
                165                 170                 175

Thr Met Met Pro Ser Trp Ile Leu Pro Ala Phe Pro Ile Met Leu Ser
            180                 185                 190

Gly Thr Ile Ala Ser Val Ile Ala Glu Gln Gln Pro Ala Arg Ser Ala
        195                 200                 205

Ile Pro Met Ile Val Ala Gly Thr Thr Phe Gln Gly Leu Gly Phe Ser
    210                 215                 220

Ile Ser Phe Leu Met Tyr Ala His Tyr Ile Gly Arg Leu Met Glu Thr
225                 230                 235                 240

Gly Leu Pro Ser Arg Glu His Arg Pro Gly Met Phe Ile Cys Val Gly
                245                 250                 255

Pro Pro Ala Phe Thr Ala Leu Ala Leu Ile Gly Met Thr Asn Gly Leu
            260                 265                 270
```

```
Pro Glu Asp Phe Gln Val Leu Gln Asp Pro His Pro Phe Gln Asp Ala
    275                 280                 285

His Ile Leu Arg Leu Leu Ala Ile Ala Thr Gly Ala Phe Leu Trp Ala
    290                 295                 300

Leu Ser Leu Trp Phe Phe Ser Ile Ala Ile Ile Ala Thr Ile Arg Leu
305                 310                 315                 320

Pro Pro Thr Ala Phe His Leu Asn Trp Trp Ala Met Val Phe Pro Asn
                325                 330                 335

Thr Gly Phe Thr Leu Ala Thr Ile Thr Leu Gly Lys Ala Phe Asp Ser
            340                 345                 350

Pro Gly Val Lys Gly Val Gly Ser Ala Met Ser Ile Cys Ile Val Gly
        355                 360                 365

Met Trp Leu Phe Val Phe Ala Ser Asn Ile Arg Ala Val Val Lys Arg
    370                 375                 380

Asp Ile Val Phe Pro Gly Lys Asp Glu Asp Val Ser Glu
385                 390                 395

<210> SEQ ID NO 7
<211> LENGTH: 36
<212> TYPE: DNA
<213> ORGANISM: Aspergillus aculeatus

<400> SEQUENCE: 7
gtgatagaac atcgtccata atgctcgggc aacact                       36

<210> SEQ ID NO 8
<211> LENGTH: 40
<212> TYPE: DNA
<213> ORGANISM: Aspergillus aculeatus

<400> SEQUENCE: 8
gtgtcagtca cctctagtta ttactccgat acatcctcgt                   40

<210> SEQ ID NO 9
<211> LENGTH: 36
<212> TYPE: DNA
<213> ORGANISM: Aspergillus aculeatus

<400> SEQUENCE: 9
tgtgatagaa catcgtccat aatgcacgac cacagc                       36

<210> SEQ ID NO 10
<211> LENGTH: 40
<212> TYPE: DNA
<213> ORGANISM: Aspergillus aculeatus

<400> SEQUENCE: 10
gtgtcagtca cctctagtta tcattcgaac aactcggaca                   40

<210> SEQ ID NO 11
<211> LENGTH: 1430
<212> TYPE: DNA
<213> ORGANISM: Aspergillus oryzae

<400> SEQUENCE: 11
atggtcaaag ctggtgagtt agcaatcctt aacagatgac actctcatag gtactaactc    60
gaaacgttag cggtacttgg agcttctggt ggcattggcc aggtatggat atccccacgc   120
cttacaaccc tggtcacaat atgaccttgt tcgatactga ctatctccca agccactgtc   180
tctcctgttg aagacctgtc ccttagttga agagcttgct ctctacgatg ttgtgaacac   240
```

-continued

```
ccctggtgtt gctgctgatc tatcccacat ctcgtctatc gctgtacgtt actgccacaa    300
tgcgaattgc ccgatggaag aggcgaaaaa tggtatcttg cttacctggg cgattagaaa    360
atctctggtt ttctgcccaa agatgatggg ctgaagcagg cccttactgg tgctaatatt    420
gttgtcatcc cggctggtat tccccgtaag tccctaccct ttcgcattgc tcctcgtatg    480
ttcgctggtg gccagttttc tgatagttga taggcaagcc tggtatgacc cgtgacgacc    540
tcttcaagat caacgccggc atagtgcgag acttggtcaa gggtatcgcc gagttctgcc    600
ccaaggcctt tgttctggtt atctcaaacc ccgttaattc tactgttcct attgctgcag    660
aggtgctcaa agccgctggc gtctttgacc cgaagcgcct ctttggtgtc accacactgg    720
acgtcgttcg tgcagagact ttcacccaag agttctcggg ccagaaggat ccttctgctg    780
ttcaaatccc agttgttggt ggccactctg gagagaccat tgtcccccctc ttcagcaaga    840 ctacccccgc aattcagata cccgaggaga agtatgacgc actgatccac cgtaggttgt    900
cccaaagaat ctcatgaata tcttgctgta agcactaact atgcttcagg cgtccaattt    960
ggtggagatg aggtggtcca agctaaggac ggtgctggtt ccgccacctt gtctatggcc   1020
tatgccggtt acaggtaggg atgctgcgta ccgtgagagc actcgcggct aacatgccat   1080
aggttcgctg agagtgtaat caaagcttca aagggtcaaa cgggtattgt cgagcctacc   1140
ttcgtctacc tgcctggaat tcccggcggt gatgagatcg ttaaggcaac tggcgtggaa   1200
ttcttctcta ctcttgtaac cttaggagta agattcatct cctcacagaa tcttcgttca   1260
tatcacgcca ggctaacgct attaaacaga ctaatggcgc agagaaggct agcaacgttc   1320
ttgagggcgt gaccgagaag gaaaagaagc ttctcgaggc ttgcacgaaa ggccttaagg   1380
gtaatatcga gaaaggcatc gacttcgtta agaacccacc accaaagtaa              1430
```

<210> SEQ ID NO 12
<211> LENGTH: 330
<212> TYPE: PRT
<213> ORGANISM: Aspergillus oryzae

<400> SEQUENCE: 12

```
Met Val Lys Ala Ala Val Leu Gly Ala Ser Gly Gly Ile Gly Gln Pro
1               5                   10                  15

Leu Ser Leu Leu Leu Lys Thr Cys Pro Leu Val Glu Glu Leu Ala Leu
            20                  25                  30

Tyr Asp Val Val Asn Thr Pro Gly Val Ala Ala Asp Leu Ser His Ile
        35                  40                  45

Ser Ser Ile Ala Lys Ile Ser Gly Phe Leu Pro Lys Asp Asp Gly Leu
    50                  55                  60

Lys Gln Ala Leu Thr Gly Ala Asn Ile Val Val Ile Pro Ala Gly Ile
65                  70                  75                  80

Pro Arg Lys Pro Gly Met Thr Arg Asp Asp Leu Phe Lys Ile Asn Ala
                85                  90                  95

Gly Ile Val Arg Asp Leu Val Lys Gly Ile Ala Glu Phe Cys Pro Lys
            100                 105                 110

Ala Phe Val Leu Val Ile Ser Asn Pro Val Asn Ser Thr Val Pro Ile
        115                 120                 125

Ala Ala Glu Val Leu Lys Ala Ala Gly Val Phe Asp Pro Lys Arg Leu
    130                 135                 140

Phe Gly Val Thr Thr Leu Asp Val Val Arg Ala Glu Thr Phe Thr Gln
145                 150                 155                 160

Glu Phe Ser Gly Gln Lys Asp Pro Ser Ala Val Gln Ile Pro Val Val
```

```
                    165                 170                 175
Gly Gly His Ser Gly Glu Thr Ile Val Pro Leu Phe Ser Lys Thr Thr
                180                 185                 190
Pro Ala Ile Gln Ile Pro Glu Glu Lys Tyr Asp Ala Leu Ile His Arg
            195                 200                 205
Val Gln Phe Gly Gly Asp Glu Val Gln Ala Lys Asp Gly Ala Gly
        210                 215                 220
Ser Ala Thr Leu Ser Met Ala Tyr Ala Gly Tyr Arg Phe Ala Glu Ser
225                 230                 235                 240
Val Ile Lys Ala Ser Lys Gly Gln Thr Gly Ile Val Glu Pro Thr Phe
                245                 250                 255
Val Tyr Leu Pro Gly Ile Pro Gly Gly Asp Glu Ile Val Lys Ala Thr
            260                 265                 270
Gly Val Glu Phe Phe Ser Thr Leu Val Thr Leu Gly Thr Asn Gly Ala
        275                 280                 285
Glu Lys Ala Ser Asn Val Leu Glu Gly Val Thr Glu Lys Glu Lys Lys
        290                 295                 300
Leu Leu Glu Ala Cys Thr Lys Gly Leu Lys Gly Asn Ile Glu Lys Gly
305                 310                 315                 320
Ile Asp Phe Val Lys Asn Pro Pro Lys
                325                 330

<210> SEQ ID NO 13
<211> LENGTH: 36
<212> TYPE: DNA
<213> ORGANISM: Aspergillus oryzae

<400> SEQUENCE: 13
agaacatcgt ccataatggt caaagctggt gagtta                              36

<210> SEQ ID NO 14
<211> LENGTH: 40
<212> TYPE: DNA
<213> ORGANISM: Aspergillus oryzae

<400> SEQUENCE: 14
gtgtcagtca cctctagtta ttactttggt ggtgggttct                          40

<210> SEQ ID NO 15
<211> LENGTH: 3643
<212> TYPE: DNA
<213> ORGANISM: Aspergillus oryzae

<400> SEQUENCE: 15
atggcggctc cgtttcgtca gcctgaggag gcggtcgatg acaccgagtt catcgatgac    60
caccatgaac acctccgtga taccgtgcac atcggttgc gcgccaattc ctccattatg    120
cacttccaga gatcctcgt cgccaaccgt ggtgagatcc ccattcgtat cttcagaacg    180
gcccacgagc tgtccttgca gacggttgct atctactctc atgaggatcg actgtcaatg    240
caccgtcaaa aggccgatga ggcctacatg attggccacc gcggtcagta caccctgtc     300 ggtgcgtacc tggcgggcga tgagatcatc aagatcgccc tggagcacgg tgtccagctg    360 atccaccgg gctacggttt cttgtccgag aacgccgact cgcccgcaa ggttgagaac      420 gccggcattg tctttgtggg acccactccc gataccattg acagcttggg tgacaaggtg    480
tcggcccgtc ggctggccat taagtgcgag gtccctgtcg ttccgggtac ggagggcccc    540
gtcgagcgct atgaggaggt caaggcgttc acagacacct atggcttccc catcatcatc    600
```

| | |
|---|---|
| aaggctgcct ttggcggtgg tggccgtggt atgcgtgtgg tccgtgacca ggccgagctg | 660 |
| cgtgactcgt tcgagcgagc cacctctgag gcccgctccg ccttcggcaa tggtaccgtc | 720 |
| ttcgtcgagc gcttcctcga caaacccaag cacattgaag tccagcttct gggtgacagc | 780 |
| cacggcaacg ttgtccatct gtttgagcgt gactgctccg tgcagcgtcg tcaccagaag | 840 |
| gtcgttgagg ttgctccggc taaggacctg ccagccgatg tccgggaccg catcctggcc | 900 |
| gatgctgtga agctggccaa gtccgtcaac taccgtaacg ccggtacagc tgagttcctg | 960 |
| gtggaccagc agaaccgcca ctacttcatt gaaatcaatc ctcgtatcca gtcgagcac | 1020 |
| accatcaccg aagagattac tggtatcgat atcgtggctg cacagatcca gattgctgct | 1080 |
| ggtgcaagcc tcgagcaact gggcctgact caggaccgca tctccgcccg cggatttgcc | 1140 |
| attcaatgtc gtatcaccac ggaagatccc gccaaggggt tctctccgga tactggtaag | 1200 |
| attgaggttt atcgttccgc tggtggtaac ggtgtccgtc tggatggtgg taacggtttc | 1260 |
| gctggtgcta tcatcacccc tcactacgac tccatgctgg tcaagtgcac ctgccgtggt | 1320 |
| tcgacctatg aaatcgctcg tcgcaaggtt gtgcgtgcct tggtcgagtt ccgtattcgt | 1380 |
| ggtgtgaaga ccaacattcc cttcctgact tcgcttctga gccacccgac cttcgtcgat | 1440 |
| ggaaactgct ggaccacttt catcgacgac acccctgaat tgttctctct tgtcggcagt | 1500 |
| cagaaccgtg cccagaagct gctcgcatac ctcggcgatg tagctgtcaa cggtagtagc | 1560 |
| atcaagggcc aaattggcga gcccaagctc aagggtgatg tcatcaagcc gaagcttttc | 1620 |
| gatgccgagg gcaagccgct tgacgtttcc gcccctgca ccaagggttg gaagcagatt | 1680 |
| ctggaccggg agggtccggc tgcctttgcg aaggccgtgc gtgccaacaa gggttgcttg | 1740 |
| atcatggata ctacctggcg tgacgcccac cagtctttgc tggccacccg tgtgcgtacc | 1800 |
| atcgacttgt tgaacatcgc ccatgagacc agctacgcct actccaatgc gtacagtttg | 1860 |
| gaatgctggg gtggtgctac cttcgatgtg ccatgcgtt tcctctatga ggaccctgg | 1920 |
| gaccgcctgc gcaagatgcg taaggctgtt cctaacatcc cattccagat gttgctccgt | 1980 |
| ggtgccaacg gtgtcgccta ctcttccctc ccagacaacg ccatctacca cttctgtaag | 2040 |
| caggctaaga agtgcggtgt cgacattttc cgtgttttcg acgccctcaa cgatgtcgat | 2100 |
| cagctcgagg tcggtatcaa ggctgttcat gctgccgagg gtgttgtcga ggccaccatg | 2160 |
| tgctacagcg gtgacatgct gaaccccac aagaagtaca acctggagta ctacatggcc | 2220 |
| ttggtggata agattgtagc catgaagcct cacatccttg gtatcaagga tatggccggt | 2280 |
| gtgctgaagc ccaggccgc tcgcctgttg gtgggctcca tccgtcagcg ctaccctgac | 2340 |
| cttcccatcc acgtccacac ccacgactcc gctggtactg gtgtagcttc catgattgcc | 2400 |
| tgtgcccagg cgggtgccga cgccgtggac gccgcgaccg acagcatgtc cggtatgacc | 2460 |
| tcccagccta gcattggtgc cattctggcc tctcttgagg gcactgagca agacccggt | 2520 |
| ctcaacctcg cccacgtgcg cgctattgat agctactggg cacagctgcg cttgctctac | 2580 |
| tctcctttcg aggcgggtct cactggcccc gaccctgagg tctacgagca cgagatccct | 2640 |
| ggtggtcagt tgaccaacct tatcttccag gccagtcagc tcggcttggg ccagcagtgg | 2700 |
| gccgaaacca agaaggccta tgaggcggct aatgatttac tcggcgacat tgtaaaggtc | 2760 |
| actcccacct ccaaggtggt cggtgacttg gctcagttca tggtctcgaa caaactgact | 2820 |
| ccagaggatg ttgttgagcg tgctggtgag ctggacttcc ctggttctgt gctcgaattc | 2880 |
| ctcgaaggtc tcatgggaca gcccttcggt ggattcccg agccattgcg ctcccgcgcc | 2940 |
| ctgcgcgatc gccgcaagct cgagaagcgt ccaggtctct acctcgagcc tttggatttg | 3000 |

-continued

```
gctaagatca agagccagat ccgtgagaag ttcggtgctg ctactgagta tgacgtggcc    3060
agctatgcca tgtatcccaa ggtcttcgag gactacaaga agttcgtcca gaagttcggt    3120
gatctctccg tcttgcccac acggtacttc ttggccaagc ctgagattgg cgaggagttc    3180
cacgttgagc tggagaaggg taaggtgctc atcctgaagt tgttggccat cggccctctt    3240
tcagagcaga ctggtcagcg tgaggtcttc tacgaagtca acggtgaggt gcgccaggtc    3300
gctgttgatg acaacaaggc ttccgtggac aacacttcac gccctaaggc cgatgtgggt    3360
gacagcagcc aggtcggtgc tcctatgagc ggtgtggttg ttgaaatccg tgtccacgat    3420
ggtctggagg ttaagaaggg tgacccactt gccgtcctga gtgccatgaa gatggtaagt    3480
tcattccgaa tcattttctc cactggtcaa ctacagatgc taacagctta ccaggaaat    3540 ggttatctct gctcctcaca gtggaaaggt ctccagcttg ctggtcaagg agggcgattc    3600
tgtggatggc caggatctcg tctgcaagat cgtcaaagcg taa                      3643
```

<210> SEQ ID NO 16
<211> LENGTH: 1193
<212> TYPE: PRT
<213> ORGANISM: Aspergillus oryzae

<400> SEQUENCE: 16

```
Met Ala Ala Pro Phe Arg Gln Pro Glu Glu Ala Val Asp Asp Thr Glu
1               5                   10                  15

Phe Ile Asp Asp His His Glu His Leu Arg Asp Thr Val His His Arg
                20                  25                  30

Leu Arg Ala Asn Ser Ser Ile Met His Phe Gln Lys Ile Leu Val Ala
            35                  40                  45

Asn Arg Gly Glu Ile Pro Ile Arg Ile Phe Arg Thr Ala His Glu Leu
        50                  55                  60

Ser Leu Gln Thr Val Ala Ile Tyr Ser His Glu Asp Arg Leu Ser Met
65                  70                  75                  80

His Arg Gln Lys Ala Asp Glu Ala Tyr Met Ile Gly His Arg Gly Gln
                85                  90                  95

Tyr Thr Pro Val Gly Ala Tyr Leu Ala Gly Asp Glu Ile Ile Lys Ile
                100                 105                 110

Ala Leu Glu His Gly Val Gln Leu Ile His Pro Gly Tyr Gly Phe Leu
            115                 120                 125

Ser Glu Asn Ala Asp Phe Ala Arg Lys Val Glu Asn Ala Gly Ile Val
        130                 135                 140

Phe Val Gly Pro Thr Pro Asp Thr Ile Asp Ser Leu Gly Asp Lys Val
145                 150                 155                 160

Ser Ala Arg Arg Leu Ala Ile Lys Cys Glu Val Pro Val Pro Gly
                165                 170                 175

Thr Glu Gly Pro Val Glu Arg Tyr Glu Glu Val Lys Ala Phe Thr Asp
                180                 185                 190

Thr Tyr Gly Phe Pro Ile Ile Ile Lys Ala Ala Phe Gly Gly Gly Gly
            195                 200                 205

Arg Gly Met Arg Val Val Arg Asp Gln Ala Glu Leu Arg Asp Ser Phe
        210                 215                 220

Glu Arg Ala Thr Ser Glu Ala Arg Ser Ala Phe Gly Asn Gly Thr Val
225                 230                 235                 240

Phe Val Glu Arg Phe Leu Asp Lys Pro Lys His Ile Glu Val Gln Leu
                245                 250                 255

Leu Gly Asp Ser His Gly Asn Val Val His Leu Phe Glu Arg Asp Cys
                260                 265                 270
```

```
Ser Val Gln Arg Arg His Gln Lys Val Glu Val Ala Pro Ala Lys
            275                 280                 285
Asp Leu Pro Ala Asp Val Arg Asp Arg Ile Leu Ala Asp Ala Val Lys
        290                 295                 300
Leu Ala Lys Ser Val Asn Tyr Arg Asn Ala Gly Thr Ala Glu Phe Leu
305                 310                 315                 320
Val Asp Gln Gln Asn Arg His Tyr Phe Ile Glu Ile Asn Pro Arg Ile
                325                 330                 335
Gln Val Glu His Thr Ile Thr Glu Glu Ile Thr Gly Ile Asp Ile Val
            340                 345                 350
Ala Ala Gln Ile Gln Ile Ala Ala Gly Ala Ser Leu Glu Gln Leu Gly
        355                 360                 365
Leu Thr Gln Asp Arg Ile Ser Ala Arg Gly Phe Ala Ile Gln Cys Arg
    370                 375                 380
Ile Thr Thr Glu Asp Pro Ala Lys Gly Phe Ser Pro Asp Thr Gly Lys
385                 390                 395                 400
Ile Glu Val Tyr Arg Ser Ala Gly Gly Asn Gly Val Arg Leu Asp Gly
                405                 410                 415
Gly Asn Gly Phe Ala Gly Ala Ile Ile Thr Pro His Tyr Asp Ser Met
            420                 425                 430
Leu Val Lys Cys Thr Cys Arg Gly Ser Thr Tyr Glu Ile Ala Arg Arg
        435                 440                 445
Lys Val Val Arg Ala Leu Val Glu Phe Arg Ile Arg Gly Val Lys Thr
    450                 455                 460
Asn Ile Pro Phe Leu Thr Ser Leu Leu Ser His Pro Thr Phe Val Asp
465                 470                 475                 480
Gly Asn Cys Trp Thr Thr Phe Ile Asp Asp Thr Pro Glu Leu Phe Ser
                485                 490                 495
Leu Val Gly Ser Gln Asn Arg Ala Gln Lys Leu Leu Ala Tyr Leu Gly
            500                 505                 510
Asp Val Ala Val Asn Gly Ser Ser Ile Lys Gly Gln Ile Gly Glu Pro
        515                 520                 525
Lys Leu Lys Gly Asp Val Ile Lys Pro Lys Leu Phe Asp Ala Glu Gly
    530                 535                 540
Lys Pro Leu Asp Val Ser Ala Pro Cys Thr Lys Gly Trp Lys Gln Ile
545                 550                 555                 560
Leu Asp Arg Glu Gly Pro Ala Ala Phe Ala Lys Ala Val Arg Ala Asn
                565                 570                 575
Lys Gly Cys Leu Ile Met Asp Thr Thr Trp Arg Asp Ala His Gln Ser
            580                 585                 590
Leu Leu Ala Thr Arg Val Arg Thr Ile Asp Leu Leu Asn Ile Ala His
        595                 600                 605
Glu Thr Ser Tyr Ala Tyr Ser Asn Ala Tyr Ser Leu Glu Cys Trp Gly
    610                 615                 620
Gly Ala Thr Phe Asp Val Ala Met Arg Phe Leu Tyr Glu Asp Pro Trp
625                 630                 635                 640
Asp Arg Leu Arg Lys Met Arg Lys Ala Val Pro Asn Ile Pro Phe Gln
                645                 650                 655
Met Leu Leu Arg Gly Ala Asn Gly Val Ala Tyr Ser Ser Leu Pro Asp
            660                 665                 670
Asn Ala Ile Tyr His Phe Cys Lys Gln Ala Lys Lys Cys Gly Val Asp
        675                 680                 685
Ile Phe Arg Val Phe Asp Ala Leu Asn Asp Val Asp Gln Leu Glu Val
```

```
                690              695              700
Gly Ile Lys Ala Val His Ala Glu Gly Val Glu Ala Thr Met
705                  710                  715              720

Cys Tyr Ser Gly Asp Met Leu Asn Pro His Lys Tyr Asn Leu Glu
            725                  730                  735

Tyr Tyr Met Ala Leu Val Asp Lys Ile Val Ala Met Lys Pro His Ile
                740                  745                  750

Leu Gly Ile Lys Asp Met Ala Gly Val Leu Lys Pro Gln Ala Ala Arg
                755                  760                  765

Leu Leu Val Gly Ser Ile Arg Gln Arg Tyr Pro Asp Leu Pro Ile His
        770                  775                  780

Val His Thr His Asp Ser Ala Gly Thr Gly Val Ala Ser Met Ile Ala
785                  790                  795                  800

Cys Ala Gln Ala Gly Ala Asp Ala Val Asp Ala Ala Thr Asp Ser Met
                805                  810                  815

Ser Gly Met Thr Ser Gln Pro Ser Ile Gly Ala Ile Leu Ala Ser Leu
            820                  825                  830

Glu Gly Thr Glu Gln Asp Pro Gly Leu Asn Leu Ala His Val Arg Ala
            835                  840                  845

Ile Asp Ser Tyr Trp Ala Gln Leu Arg Leu Leu Tyr Ser Pro Phe Glu
850                  855                  860

Ala Gly Leu Thr Gly Pro Asp Pro Glu Val Tyr Glu His Glu Ile Pro
865                  870                  875                  880

Gly Gly Gln Leu Thr Asn Leu Ile Phe Gln Ala Ser Gln Leu Gly Leu
                885                  890                  895

Gly Gln Gln Trp Ala Glu Thr Lys Lys Ala Tyr Glu Ala Ala Asn Asp
            900                  905                  910

Leu Leu Gly Asp Ile Val Lys Val Thr Pro Thr Ser Lys Val Val Gly
            915                  920                  925

Asp Leu Ala Gln Phe Met Val Ser Asn Lys Leu Thr Pro Glu Asp Val
        930                  935                  940

Val Glu Arg Ala Gly Glu Leu Asp Phe Pro Gly Ser Val Leu Glu Phe
945                  950                  955                  960

Leu Glu Gly Leu Met Gly Gln Pro Phe Gly Gly Phe Pro Glu Pro Leu
                965                  970                  975

Arg Ser Arg Ala Leu Arg Asp Arg Arg Lys Leu Glu Lys Pro Gly
            980                  985                  990

Leu Tyr Leu Glu Pro Leu Asp Leu Ala Lys Ile Lys Ser Gln Ile Arg
        995                  1000                 1005

Glu Lys Phe Gly Ala Ala Thr Glu Tyr Asp Val Ala Ser Tyr Ala
    1010                 1015                 1020

Met Tyr Pro Lys Val Phe Glu Asp Tyr Lys Lys Phe Val Gln Lys
    1025                 1030                 1035

Phe Gly Asp Leu Ser Val Leu Pro Thr Arg Tyr Phe Leu Ala Lys
    1040                 1045                 1050

Pro Glu Ile Gly Glu Glu Phe His Val Glu Leu Glu Lys Gly Lys
    1055                 1060                 1065

Val Leu Ile Leu Lys Leu Leu Ala Ile Gly Pro Leu Ser Glu Gln
    1070                 1075                 1080

Thr Gly Gln Arg Glu Val Phe Tyr Glu Val Asn Gly Glu Val Arg
    1085                 1090                 1095

Gln Val Ala Val Asp Asp Asn Lys Ala Ser Val Asp Asn Thr Ser
    1100                 1105                 1110
```

```
Arg Pro Lys Ala Asp Val Gly Asp Ser Ser Gln Val   Gly Ala Pro
    1115                1120                1125

Met Ser Gly Val Val Val Glu Ile Arg Val His Asp   Gly Leu Glu
    1130                1135                1140

Val Lys Lys Gly Asp Pro Leu Ala Val Leu Ser Ala   Met Lys Met
    1145                1150                1155

Glu Met Val Ile Ser Ala Pro His Ser Gly Lys Val   Ser Ser Leu
    1160                1165                1170

Leu Val Lys Glu Gly Asp Ser Val Asp Gly Gln Asp   Leu Val Cys
    1175                1180                1185

Lys Ile Val Lys Ala
    1190

<210> SEQ ID NO 17
<211> LENGTH: 36
<212> TYPE: DNA
<213> ORGANISM: Aspergillus oryzae

<400> SEQUENCE: 17
tagaacatcg tccataatgg cggctccgtt tcgtca                              36

<210> SEQ ID NO 18
<211> LENGTH: 40
<212> TYPE: DNA
<213> ORGANISM: Aspergillus oryzae

<400> SEQUENCE: 18
gtgtcagtca cctctagtta ttattacgct ttgacgatct                          40

<210> SEQ ID NO 19
<211> LENGTH: 1294
<212> TYPE: DNA
<213> ORGANISM: Aspergillus oryzae

<400> SEQUENCE: 19
atgttcgctg ctcgccagtc tttcaaccct ctccagaagc gcgccttctc cgcctctgcc     60
agccaggtgt gtgattgaat ggatccattg gacctcggag ctagtctgc aacatcaaca    120 aaactaacat actaacttat cttcttcata ggcttccaag gttgccgttc ttggtgccgc    180
tggtggcatt ggccagcctc tctcccttct cctcaagctc aaccccgtg tttctgagct    240 tgccctctac gatatccgcg gtggccctgg tatgttttg cacagcttgc aacatctccg    300
acttcggtga ttcaagacag ggctaacata aggatacaat aggtgttgcc gctgacctga    360
gccacatcaa caccaacagc accgtctctg gctacgaggc taccccctct ggcctccgtg    420
atgctctcaa gggctccgag atcgtcctca tccctgccgg tgttcctcgc aagcccggca    480
tgacccgtga cggtatgaac cgttaacttg tcaatggcac tgggaattga atactaatta    540
taatatcgcc agacctgttc aacaccaacg cctccattgt ccgcgacctt gctaaggccg    600
ccgccgaggc ttccccgag gccaacatcc tcgtcatctc caaccctgta tgacgctttc    660
cacccactgc taccagttat ctcgcgctaa ttgcaatcag gtcaactcca ccgtcccat    720 cgtctctgag gtcttcaagt ccaagggtgt ctacaacccc aagcgtctct tcggtgtcac    780 taccccttgac gttgtccgtg cctctcgctt catctcccag gtccagaaga ccgacccctc    840
caacgaggcc gtcactgtcg tcggtggtca ctccggtgtg accattgtcc ctcttctctc    900
ccagtccagc cacccagca ttgagggtaa gacccgcgat gagctcgtca accgcatcca    960
gttcggtggt gatgaggttg tcaaggccaa ggatggtgct ggctctgcca ccctctccat   1020
```

```
ggccatggct ggtgctcgca tggctgagtc cctcctgaag gccgcccagg gtgagaaggg    1080
tgtcgttgag cccactttcg tcgacagccc tctctacaag gaccagggtg ttgacttctt    1140
cgcctccaag gtcgagctcg gccccaacgg tgttgagaag atcctccccg ttggccaggt    1200
caacgcctac gaggagaagc tcctcgaggc ctgccttggt gacctcaaga gaacatcca    1260 gaagggtatt gacttcgtca aggccaaccc ttaa                               1294
```

<210> SEQ ID NO 20
<211> LENGTH: 340
<212> TYPE: PRT
<213> ORGANISM: Aspergillus oryzae

<400> SEQUENCE: 20

```
Met Phe Ala Ala Arg Gln Ser Phe Asn Leu Leu Gln Lys Arg Ala Phe
  1               5                  10                  15

Ser Ala Ser Ala Ser Gln Ala Ser Lys Val Ala Val Leu Gly Ala Ala
                 20                  25                  30

Gly Gly Ile Gly Gln Pro Leu Ser Leu Leu Lys Leu Asn Pro Arg
             35                  40                  45

Val Ser Glu Leu Ala Leu Tyr Asp Ile Arg Gly Pro Gly Val Ala
 50                  55                  60

Ala Asp Leu Ser His Ile Asn Thr Asn Ser Thr Val Ser Gly Tyr Glu
 65                  70                  75                  80

Ala Thr Pro Ser Gly Leu Arg Asp Ala Leu Lys Gly Ser Glu Ile Val
                 85                  90                  95

Leu Ile Pro Ala Gly Val Pro Arg Lys Pro Gly Met Thr Arg Asp Asp
            100                 105                 110

Leu Phe Asn Thr Asn Ala Ser Ile Val Arg Asp Leu Ala Lys Ala Ala
            115                 120                 125

Ala Glu Ala Ser Pro Glu Ala Asn Ile Leu Val Ile Ser Asn Pro Val
130                 135                 140

Asn Ser Thr Val Pro Ile Val Ser Glu Val Phe Lys Ser Lys Gly Val
145                 150                 155                 160

Tyr Asn Pro Lys Arg Leu Phe Gly Val Thr Thr Leu Asp Val Val Arg
                165                 170                 175

Ala Ser Arg Phe Ile Ser Gln Val Gln Lys Thr Asp Pro Ser Asn Glu
            180                 185                 190

Ala Val Thr Val Val Gly Gly His Ser Gly Val Thr Ile Val Pro Leu
            195                 200                 205

Leu Ser Gln Ser Ser His Pro Ser Ile Glu Gly Lys Thr Arg Asp Glu
            210                 215                 220

Leu Val Asn Arg Ile Gln Phe Gly Gly Asp Glu Val Val Lys Ala Lys
225                 230                 235                 240

Asp Gly Ala Gly Ser Ala Thr Leu Ser Met Ala Met Ala Gly Ala Arg
                245                 250                 255

Met Ala Glu Ser Leu Leu Lys Ala Ala Gln Gly Glu Lys Gly Val Val
            260                 265                 270

Glu Pro Thr Phe Val Asp Ser Pro Leu Tyr Lys Asp Gln Gly Val Asp
            275                 280                 285

Phe Phe Ala Ser Lys Val Glu Leu Gly Pro Asn Gly Val Glu Lys Ile
            290                 295                 300

Leu Pro Val Gly Gln Val Asn Ala Tyr Glu Glu Lys Leu Leu Glu Ala
305                 310                 315                 320

Cys Leu Gly Asp Leu Lys Lys Asn Ile Gln Lys Gly Ile Asp Phe Val
                325                 330                 335
```

```
Lys Ala Asn Pro
            340

<210> SEQ ID NO 21
<211> LENGTH: 36
<212> TYPE: DNA
<213> ORGANISM: Aspergillus aculeatus

<400> SEQUENCE: 21
ccaacagaca catctaaaca atgcacgacc acagca                                    36

<210> SEQ ID NO 22
<211> LENGTH: 40
<212> TYPE: DNA
<213> ORGANISM: Aspergillus aculeatus

<400> SEQUENCE: 22
gtgtcagtca cctctagtta tcattcgaac aactcggaca                                40
```